US012037401B2

(12) United States Patent
Croll et al.

(10) Patent No.: US 12,037,401 B2
(45) Date of Patent: Jul. 16, 2024

(54) ANTI-TrkB MONOCLONAL ANTIBODIES AND METHODS OF USE

(71) Applicant: REGENERON PHARMACEUTICALS, INC., Tarrytown, NY (US)

(72) Inventors: Susan Croll, Putnam Valley, NY (US); Min Gao, Montvale, NJ (US); Ying Hu, Scarsdale, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 226 days.

(21) Appl. No.: 17/342,749

(22) Filed: Jun. 9, 2021

(65) Prior Publication Data
US 2022/0411515 A1 Dec. 29, 2022

Related U.S. Application Data

(62) Division of application No. 16/202,881, filed on Nov. 28, 2018, now Pat. No. 11,066,474.

(60) Provisional application No. 62/592,657, filed on Nov. 30, 2017.

(51) Int. Cl.
C07K 16/28 (2006.01)
A61K 9/00 (2006.01)
A61K 39/00 (2006.01)
A61P 25/00 (2006.01)

(52) U.S. Cl.
CPC ........ *C07K 16/2863* (2013.01); *A61K 9/0019* (2013.01); *A61P 25/00* (2018.01); *A61K 2039/505* (2013.01); *C07K 2317/21* (2013.01); *C07K 2317/56* (2013.01); *C07K 2317/565* (2013.01); *C07K 2317/75* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 6,225,282 | B1 | 5/2001 | Gao |
| 7,750,122 | B2 | 7/2010 | Cho et al. |
| 7,935,342 | B2 | 5/2011 | Lin et al. |
| 8,642,035 | B2 | 2/2014 | Luehrsen |
| 9,028,820 | B2 | 5/2015 | Hofbauer et al. |
| 9,914,781 | B1 | 3/2018 | Bhinder et al. |
| 10,392,438 | B2 | 8/2019 | Bennett et al. |
| 10,941,203 | B2 * | 3/2021 | Lu .......................... A61P 31/00 |
| 10,975,152 | B2 * | 4/2021 | Lerner .................... A61P 27/06 |
| 2007/0059304 | A1 | 3/2007 | Cho et al. |
| 2010/0086997 | A1 | 4/2010 | Lin et al. |
| 2010/0150914 | A1 | 6/2010 | Wang et al. |
| 2010/0196390 | A1 | 8/2010 | Lin et al. |
| 2011/0150893 | A1 | 6/2011 | Cho et al. |
| 2016/0354465 | A1 | 12/2016 | Mi |
| 2017/0029511 | A1 | 2/2017 | Saragovi et al. |
| 2020/0017590 | A1 * | 1/2020 | Lu .......................... C07K 16/00 |
| 2020/0165345 | A1 * | 5/2020 | Bhinder .................. A61P 25/02 |

FOREIGN PATENT DOCUMENTS

| WO | WO 2006/133164 A2 | 12/2006 |
| WO | WO 2010/086828 | 8/2010 |
| WO | WO 2011/103667 | 9/2011 |
| WO | WO 2015/173756 | 11/2015 |
| WO | WO 2017/085035 | 5/2017 |
| WO | WO 2017/192538 | 11/2017 |
| WO | WO 2018/166495 | 9/2018 |

OTHER PUBLICATIONS

Chen et al., "Neuroprotetive effect of anti-human TrkB agonist antibody in humanized TrkB rat" Poster ARVO2018 V4 Regeneron Pharmaceuticals, Inc. (Apr. 19, 2018).
M. D. Qian et al., "Novel Agonist Monoclonal Antibodies Activate TrkB Receptors and Demonstrate Potent Neurotrophic Activities", The Journal of Neuroscience, vol. 26, No. 37, Sep. 13, 2006 (Sep. 13, 2006), pp. 9394-9403.
Gab Seok Kim et al. "TrkB Agonist Antibody Pretreatment Enhances Neuronal Survival and Long-Term Sensory Motor Function Following Hypoxic Ischemic Injury in Neonatal Rats", PLOS ONE, vol. 9, No. 2, Feb. 14, 2014 (Feb. 140, 2014, p. e88962.
Bai et al., "An Agonistic TrkB mAb Causes Sustained TrkB Activation, Delays RGC Death, and Protects the Retinal Structure in Optic Nerve Axotomy and in Glaucoma" Investigative Ophthalmology & Visual Science (Sep. 2010) 51(9):4722-4731.
Hu et al., "Neurotrophic Effect of a Novel TrkB Agonist on Retinal Ganglion Cells" Investigative Ophthalmology & Visual Science (Mar. 2010) 51(3):1747-1754.
Mysona et al., "Role of BDNF/TrkB pathway in the visual system: Therapeutic implications for glaucoma" Expert Rev. Ophthalmol. (2017) 12(1):69-81.

(Continued)

Primary Examiner — Ruixiang Li
(74) Attorney, Agent, or Firm — Brian E. Davy; Bozicevic, Field & Francis LLP

(57) ABSTRACT

The present invention provides antibodies that bind specifically to TrkB and methods of using the same. According to certain embodiments, the antibodies of the invention are agonist antibodies that are neuroprotective, as shown by their effect on enhancing the survival of retinal ganglion cells in vitro. As such, these agonist antibodies may be used to treat diseases or disorders of the eye, such as, but not limited to glaucoma. In addition, other neuronal diseases or disorders may benefit from treatment with these agonist antibodies, including any disease or disorder characterized in part by neuronal damage. In certain embodiments, the invention includes antibodies that bind TrkB and mediate cell signaling. The antibodies of the invention may be fully human, non-naturally occurring antibodies.

12 Claims, 5 Drawing Sheets
Specification includes a Sequence Listing.

(56) References Cited

OTHER PUBLICATIONS

Osborne et al., "Design of a Novel Gene Therapy Construct to Achieve Sustained Brain-Derived Neurotrophic Factor Signaling in Neurons" Human Gene Therapy (Feb. 2018) 29(7):828-841.
Osborne et al., "Neuroprotection of retinal ganglion cells by a novel gene therapy construct that achieves sustained enhancement of brain-derived neurotrophic factor/tropomyosin-related kinase receptor-B signaling" Cell Death and Disease (2018) 9:1007:1-18.
Paul, William "Fundamental Immunology," 3$^{rd}$ Edition, Raven Press, New York (1993) 292-295.
Ratucan et al., "Progress in Gene Therapy to Prevent Retinal Ganglion Cell Loss in Glaucoma and Leber's Hereditary Optic Neuropathy" Neural Plasticity (2018) pp. 1-11.
Vajdos et al., "Comprehensive functional maps of the antigen-binding site of an anti-ErbB2 antibody obtained with shotgun scanning mutagenesis" J. Mol. Biol., 320:415-428 (2002).

\* cited by examiner

SEQUENCE LISTING

<160> NUMBER OF SEQ ID NOS: 104

<210> SEQ ID NO 1
<211> LENGTH: 354
<212> TYPE: DNA
<213> ORGANISM: Artificial Sequence
<220> FEATURE:
<223> OTHER INFORMATION: synthetic

<400> SEQUENCE: 1

```
caggtgcagc tggtggagtc tgggggaggc gtggtccagc ctgggaggtc cctgagactc      60
tcctgtgcag cctctggatt cagcttcagt agctttggca tgcactgggt ccgccaggct     120
ccaggcaagg gactggagtg ggtgtcagtt atatcatatg atggaattaa tacatactat     180
acagactccg tgaagggccg attcaccatc tccagagaca attccaagaa cacgctgtat     240
ctgcaaatga acggcctgag agctgaggac acggctcttt attactgtgt gcaagggtca     300
attggaaccg tttttgaata ctggggccag ggaaccctgg tcaccgtctc ctca           354
```

<210> SEQ ID NO 2
<211> LENGTH: 118
<212> TYPE: PRT
<213> ORGANISM: Artificial Sequence
<220> FEATURE:
<223> OTHER INFORMATION: synthetic

<400> SEQUENCE: 2

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Phe
            20                  25                  30

Gly Met His Trp Val Arg Gln Ala Pro Gly Lys Gly Leu Glu Trp Val
        35                  40                  45

Ser Val Ile Ser Tyr Asp Gly Ile Asn Thr Tyr Tyr Thr Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Gly Leu Arg Ala Glu Asp Thr Ala Leu Tyr Tyr Cys
                85                  90                  95

Val Gln Gly Ser Ile Gly Thr Val Phe Glu Tyr Trp Gly Gln Gly Thr
            100                 105                 110

Leu Val Thr Val Ser Ser
        115

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
ggattcagct tcagtagctt tggc                                          24

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Gly Phe Ser Phe Ser Ser Phe Gly
1               5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
atatcatatg atggaattaa taca                                          24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Ser Tyr Asp Gly Ile Asn Thr
1               5

<210> SEQ ID NO 7
<211> LENGTH: 33
<212> TYPE: DNA
<213> ORGANISM: Artificial Sequence
<220> FEATURE:
<223> OTHER INFORMATION: synthetic

<400> SEQUENCE: 7
gtgcaagggt caattggaac cgtttttgaa tac                                33

<210> SEQ ID NO 8
<211> LENGTH: 11
<212> TYPE: PRT
<213> ORGANISM: Artificial Sequence
<220> FEATURE:
<223> OTHER INFORMATION: synthetic

<400> SEQUENCE: 8

Val Gln Gly Ser Ile Gly Thr Val Phe Glu Tyr
1               5                   10

<210> SEQ ID NO 9
<211> LENGTH: 321
<212> TYPE: DNA
<213> ORGANISM: Artificial Sequence
<220> FEATURE:
<223> OTHER INFORMATION: synthetic

<400> SEQUENCE: 9
gacatccaga tgacccagtc tccatcctcc ctgtctgcat ctgtaggaga cagagtcacc    60
atcacttgcc gggcgagtca gggcattagc aattatttag cctggtatca gcagaaacca   120
gggaaagttc ctaaactcct gatctatgct gcatccactt tacaatcagg ggtcccatct   180
cggttcggtg cagtggatc tgggacagat ttcactctca ccatcagcag cctgcagcct   240
gaagatgttg caacttatta ctgtcaaaag tataccagtg ccccattcac tttcggccct   300
gggaccaaag tggatatcaa a                                              321

<210> SEQ ID NO 10
<211> LENGTH: 107
<212> TYPE: PRT
<213> ORGANISM: Artificial Sequence
<220> FEATURE:
<223> OTHER INFORMATION: synthetic

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Gly Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Thr Ser Ala Pro Phe
                85                  90                  95

Thr Phe Gly Pro Gly Thr Lys Val Asp Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
cagggcatta gcaattat                                                   18

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

Gln Gly Ile Ser Asn Tyr
1               5

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 gctgcatcc                                                                 9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Ala Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15
caaaagtata ccagtgcccc attcact                                            27

<210> SEQ ID NO 16
<211> LENGTH: 9
<212> TYPE: PRT
<213> ORGANISM: Artificial Sequence
<220> FEATURE:
<223> OTHER INFORMATION: synthetic

<400> SEQUENCE: 16

Gln Lys Tyr Thr Ser Ala Pro Phe Thr
1               5

<210> SEQ ID NO 17
<211> LENGTH: 366
<212> TYPE: DNA
<213> ORGANISM: Artificial Sequence
<220> FEATURE:
<223> OTHER INFORMATION: synthetic

<400> SEQUENCE: 17
gaggtgcagc tggtggagtc tgggggaggc ttggtccagc ctggggggtc cctaaaactc        60
tcctgtacag cctctgggtt caccttcagt ggctctgtta ttcactgggt ccgccaggct       120
tccgggaaag gctggagtg gattggccgt attagaaaca aggctaacag ttacgcgaca        180
gcatatggtg cgtcggtgac aggcaggttc accatctcca gagatgattc aaagaacacg       240
gcgtatctgc aaatgaacag cctgaaaacc gaggacacgg ccgtttatta ctgtactttc       300
ccgggtgtag tgggacgagg aggttttgac tactggggcc agggcaccct ggtcaccgtc       360
tcctca                                                                  366

<210> SEQ ID NO 18
<211> LENGTH: 122
<212> TYPE: PRT
<213> ORGANISM: Artificial Sequence
<220> FEATURE:
<223> OTHER INFORMATION: synthetic

<400> SEQUENCE: 18

```
Glu Val Gln Leu Val Glu Ser Gly Gly Gly Leu Val Gln Pro Gly Gly
1               5                   10                  15

Ser Leu Lys Leu Ser Cys Thr Ala Ser Gly Phe Thr Phe Ser Gly Ser
            20                  25                  30

Val Ile His Trp Val Arg Gln Ala Ser Gly Lys Gly Leu Glu Trp Ile
        35                  40                  45

Gly Arg Ile Arg Asn Lys Ala Asn Ser Tyr Ala Thr Ala Tyr Gly Ala
    50                  55                  60

Ser Val Thr Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Phe Pro Gly Val Val Gly Arg Gly Gly Phe Asp Tyr Trp
            100                 105                 110

Gly Gln Gly Thr Leu Val Thr Val Ser Ser
        115                 120
```

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
gggttcacct tcagtggctc tgtt                                          24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

```
Gly Phe Thr Phe Ser Gly Ser Val
1               5
```

<210> SEQ ID NO 21
<211> LENGTH: 30
<212> TYPE: DNA
<213> ORGANISM: Artificial Sequence
<220> FEATURE:
<223> OTHER INFORMATION: synthetic

<400> SEQUENCE: 21
attagaaaca aggctaacag ttacgcgaca                                    30

<210> SEQ ID NO 22
<211> LENGTH: 10
<212> TYPE: PRT
<213> ORGANISM: Artificial Sequence
<220> FEATURE:
<223> OTHER INFORMATION: synthetic

```
<400> SEQUENCE: 22

Ile Arg Asn Lys Ala Asn Ser Tyr Ala Thr
1               5                   10

<210> SEQ ID NO 23
<211> LENGTH: 39
<212> TYPE: DNA
<213> ORGANISM: Artificial Sequence
<220> FEATURE:
<223> OTHER INFORMATION: synthetic

<400> SEQUENCE: 23
actttcccgg gtgtagtggg acgaggaggt tttgactac                              39

<210> SEQ ID NO 24
<211> LENGTH: 13
<212> TYPE: PRT
<213> ORGANISM: Artificial Sequence
<220> FEATURE:
<223> OTHER INFORMATION: synthetic

<400> SEQUENCE: 24

Thr Phe Pro Gly Val Val Gly Arg Gly Gly Phe Asp Tyr
1               5                   10

<210> SEQ ID NO 25
<211> LENGTH: 339
<212> TYPE: DNA
<213> ORGANISM: Artificial Sequence
<220> FEATURE:
<223> OTHER INFORMATION: synthetic

<400> SEQUENCE: 25
gacatcgtga tgacccagtc tccagactcc ctggctgtgt ctctgggcga gggggccacc       60
atcaactgca gtccagcca gagtgtttta ttcagctcca acaataagaa ctacttagct       120
tggtaccaac agaaaccagg acagcctcct aagttgctct tttactgggc atctacccgg     180
gaatccgggg tccctgaccg attcggtggc agcgggtctg ggacagattt ctctctcacc     240
atcaacagcc tgcagactga agatgtggca gtttattact gtctccaata ttatagtatt     300
ccgtggacgt tcggccaagg gaccaaggtg gaaatcaaa                             339

<210> SEQ ID NO 26
<211> LENGTH: 113
<212> TYPE: PRT
<213> ORGANISM: Artificial Sequence
<220> FEATURE:
<223> OTHER INFORMATION: synthetic

<400> SEQUENCE: 26

Asp Ile Val Met Thr Gln Ser Pro Asp Ser Leu Ala Val Ser Leu Gly
1               5                   10                  15

Glu Gly Ala Thr Ile Asn Cys Met Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Phe Tyr Trp Ala Ser Thr Arg Glu Ser Gly Val
    50                  55                  60

Pro Asp Arg Phe Gly Gly Ser Gly Ser Gly Thr Asp Phe Ser Leu Thr
65                  70                  75                  80

Ile Asn Ser Leu Gln Thr Glu Asp Val Ala Val Tyr Tyr Cys Leu Gln
                85                  90                  95
```

Tyr Tyr Ser Ile Pro Trp Thr Phe Gly Gln Gly Thr Lys Val Glu Ile
            100                 105                 110
Lys

<210> SEQ ID NO 27
<211> LENGTH: 36
<212> TYPE: DNA
<213> ORGANISM: Artificial Sequence
<220> FEATURE:
<223> OTHER INFORMATION: synthetic

<400> SEQUENCE: 27
cagagtgttt tattcagctc caacaataag aactac                              36

<210> SEQ ID NO 28
<211> LENGTH: 12
<212> TYPE: PRT
<213> ORGANISM: Artificial Sequence
<220> FEATURE:
<223> OTHER INFORMATION: synthetic

<400> SEQUENCE: 28

Gln Ser Val Leu Phe Ser Ser Asn Asn Lys Asn Tyr
1               5                   10

<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 tgggcatct                                                            9

<210> SEQ ID NO 30
<211> LENGTH: 3
<212> TYPE: PRT
<213> ORGANISM: Artificial Sequence
<220> FEATURE:
<223> OTHER INFORMATION: synthetic

<400> SEQUENCE: 30

Trp Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: synthetic

<400> SEQUENCE: 31
ctccaatatt atagtattcc gtggacg                                        27

<210> SEQ ID NO 32
<211> LENGTH: 9
<212> TYPE: PRT
<213> ORGANISM: Artificial Sequence
<220> FEATURE:
<223> OTHER INFORMATION: synthetic

<400> SEQUENCE: 32

Leu Gln Tyr Tyr Ser Ile Pro Trp Thr

<210> SEQ ID NO 33
<211> LENGTH: 381
<212> TYPE: DNA
<213> ORGANISM: Artificial Sequence
<220> FEATURE:
<223> OTHER INFORMATION: synthetic

<400> SEQUENCE: 33

```
gaggtgcagc tggtggagtc tgggggaggc ttggtacagc ctggagggtc cctgacactc    60
tcctgtgcag cctctggatt caatttccgt gattatgaaa tgatctgggt ccgccagact   120
ccagggaagg ggctggagtg gatttcatac attagtaata gtggttatac catatactac   180
gcagactctg tgaagggccg attcaccatc tccagagaca acgccaggaa ctcaatatat   240
ctgcaagtga acagcctgag agccgaggac acggctgttt attactgttc gagacgtact   300
actatgattc gggcattag gcgtactac tattacggtc tggacgtctg gggccaaggg   360
accacggtca ccgtctcctc a                                             381
```

<210> SEQ ID NO 34
<211> LENGTH: 127
<212> TYPE: PRT
<213> ORGANISM: Artificial Sequence
<220> FEATURE:
<223> OTHER INFORMATION: synthetic

<400> SEQUENCE: 34

Glu Val Gln Leu Val Glu Ser Gly Gly Gly Leu Val Gln Pro Gly Gly
1               5                   10                  15

Ser Leu Thr Leu Ser Cys Ala Ala Ser Gly Phe Asn Phe Arg Asp Tyr
            20                  25                  30

Glu Met Ile Trp Val Arg Gln Thr Pro Gly Lys Gly Leu Glu Trp Ile
        35                  40                  45

Ser Tyr Ile Ser Asn Ser Gly Tyr Thr Ile Tyr Tyr Ala Asp Ser Val
    50                  55                  60

Lys Gly Arg Phe Thr Ile Ser Arg Asp Asn Ala Arg Asn Ser Ile Tyr
65                  70                  75                  80

Leu Gln Val Asn Ser Leu Arg Ala Glu Asp Thr Ala Val Tyr Tyr Cys
                85                  90                  95

Ser Arg Arg Thr Thr Met Ile Arg Gly Ile Arg Ala Tyr Tyr Tyr Tyr
            100                 105                 110

Gly Leu Asp Val Trp Gly Gln Gly Thr Thr Val Thr Val Ser Ser
        115                 120                 125

<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35

```
ggattcaatt tccgtgatta tgaa                                           24
```

<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36

Gly Phe Asn Phe Arg Asp Tyr Glu
1               5

<210> SEQ ID NO 37
<211> LENGTH: 24
<212> TYPE: DNA
<213> ORGANISM: Artificial Sequence
<220> FEATURE:
<223> OTHER INFORMATION: synthetic

<400> SEQUENCE: 37
attagtaata gtggttatac cata                                          24

<210> SEQ ID NO 38
<211> LENGTH: 8
<212> TYPE: PRT
<213> ORGANISM: Artificial Sequence
<220> FEATURE:
<223> OTHER INFORMATION: synthetic

<400> SEQUENCE: 38

Ile Ser Asn Ser Gly Tyr Thr Ile
1               5

<210> SEQ ID NO 39
<211> LENGTH: 60
<212> TYPE: DNA
<213> ORGANISM: Artificial Sequence
<220> FEATURE:
<223> OTHER INFORMATION: synthetic

<400> SEQUENCE: 39
tcgagacgta ctactatgat cgggggcatt agggcgtact actattacgg tctggacgtc    60

<210> SEQ ID NO 40
<211> LENGTH: 20
<212> TYPE: PRT
<213> ORGANISM: Artificial Sequence
<220> FEATURE:
<223> OTHER INFORMATION: synthetic

<400> SEQUENCE: 40

Ser Arg Arg Thr Thr Met Ile Arg Gly Ile Arg Ala Tyr Tyr Tyr Tyr
1               5                   10                  15

Gly Leu Asp Val
            20

<210> SEQ ID NO 41
<211> LENGTH: 324
<212> TYPE: DNA
<213> ORGANISM: Artificial Sequence
<220> FEATURE:
<223> OTHER INFORMATION: synthetic

<400> SEQUENCE: 41
gacatccaga tgacccagtc tccatcctcc ctgtctgcat ctgtaggaga cagagtcacc    60
atcacttgcc gggcaagtca gagcattagc agctatttaa attggtatca gcagaaacca  120
gggaaagccc ctaagctcct gatctatgct gcatccagtt tgcaaagtgg ggtcccgtca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa					324

<210> SEQ ID NO 42
<211> LENGTH: 108
<212> TYPE: PRT
<213> ORGANISM: Artificial Sequence
<220> FEATURE:
<223> OTHER INFORMATION: synthetic

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 43
<211> LENGTH: 18
<212> TYPE: DNA
<213> ORGANISM: Artificial Sequence
<220> FEATURE:
<223> OTHER INFORMATION: synthetic

<400> SEQUENCE: 43
cagagcatta gcagctat					18

<210> SEQ ID NO 44
<211> LENGTH: 6
<212> TYPE: PRT
<213> ORGANISM: Artificial Sequence
<220> FEATURE:
<223> OTHER INFORMATION: synthetic

<400> SEQUENCE: 44

Gln Ser Ile Ser Ser Tyr
1               5

<210> SEQ ID NO 45
<211> LENGTH: 9
<212> TYPE: DNA
<213> ORGANISM: Artificial Sequence
<220> FEATURE:
<223> OTHER INFORMATION: synthetic

<400> SEQUENCE: 45 gctgcatcc					9

<210> SEQ ID NO 46
<211> LENGTH: 3
<212> TYPE: PRT
<213> ORGANISM: Artificial Sequence
<220> FEATURE:
<223> OTHER INFORMATION: synthetic

<400> SEQUENCE: 46

Ala Ala Ser
1

<210> SEQ ID NO 47
<211> LENGTH: 30
<212> TYPE: DNA
<213> ORGANISM: Artificial Sequence
<220> FEATURE:
<223> OTHER INFORMATION: synthetic

<400> SEQUENCE: 47
caacagagtt acagtacccc tccgatcacc             30

<210> SEQ ID NO 48
<211> LENGTH: 10
<212> TYPE: PRT
<213> ORGANISM: Artificial Sequence
<220> FEATURE:
<223> OTHER INFORMATION: synthetic

<400> SEQUENCE: 48

Gln Gln Ser Tyr Ser Thr Pro Pro Ile Thr
1               5                   10

<210> SEQ ID NO 49
<211> LENGTH: 123
<212> TYPE: PRT
<213> ORGANISM: Artificial Sequence
<220> FEATURE:
<223> OTHER INFORMATION: M2aM14173N HCVR

<400> SEQUENCE: 49

Asn Val Ser Leu Val Glu Ser Gly Gly Gly Ser Val Lys Pro Gly Gly
1               5                   10                  15

Ser Leu Gln Leu Ser Cys Ala Ala Ser Gly Phe Thr Phe Ser Ser Ser
            20                  25                  30

Ala Met Ser Trp Ile Arg Gln Thr Pro Glu Met Arg Leu Glu Trp Val
        35                  40                  45

Ala Thr Ile Ser Asp Arg Gly Ser Tyr Thr Tyr Tyr Pro Asp Ser Val
    50                  55                  60

Glu Gly Arg Phe Thr Ile Ser Arg Asp Asn Ala Lys Asn Ile Leu Tyr
65                  70                  75                  80

Leu Gln Met Ser His Leu Met Ser Glu Asp Thr Ala Met Tyr Tyr Cys
                85                  90                  95

Ala Arg Gly Lys Gly Glu Lys Tyr Tyr Thr Ala Phe Phe Ala Tyr
            100                 105                 110

Trp Gly Gln Gly Ser Leu Val Thr Val Ser Ala
        115                 120

<210> SEQ ID NO 50
<211> LENGTH: 8
<212> TYPE: PRT
<213> ORGANISM: Artificial Sequence
<220> FEATURE:
<223> OTHER INFORMATION: M2aM14173N HCDR1

<400> SEQUENCE: 50

Gly Phe Thr Phe Ser Ser Ser Ala
1               5

<210> SEQ ID NO 51
<211> LENGTH: 8

```
<212> TYPE: PRT
<213> ORGANISM: Artificial Sequence
<220> FEATURE:
<223> OTHER INFORMATION: M2aM14173N HCDR2

<400> SEQUENCE: 51

Ile Ser Asp Arg Gly Ser Tyr Thr
1               5

<210> SEQ ID NO 52
<211> LENGTH: 16
<212> TYPE: PRT
<213> ORGANISM: Artificial Sequence
<220> FEATURE:
<223> OTHER INFORMATION: M2aM14173N HCDR3

<400> SEQUENCE: 52

Ala Arg Gly Lys Gly Glu Lys Ala Tyr Tyr Thr Ala Phe Phe Ala Tyr
1               5                   10                  15

<210> SEQ ID NO 53
<211> LENGTH: 107
<212> TYPE: PRT
<213> ORGANISM: Artificial Sequence
<220> FEATURE:
<223> OTHER INFORMATION: M2aM14173N LCVR

<400> SEQUENCE: 53

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Pro Gly Lys Ser Pro His Leu Leu Val
        35                  40                  45

His Asn Ala Glu Thr Leu Ala Glu Gly Val Pro Ser Arg Phe Ser Gly
    50                  55                  60

Ser Gly Ser Gly Pro Gln Phe Ser Leu Lys Ile Asn Ser Leu Gln Pro
65                  70                  75                  80

Gly Asp Ser Gly Thr Tyr Tyr Cys Gln His His Tyr Ser Ser Pro Trp
                85                  90                  95

Thr Phe Gly Gly Gly Thr Lys Leu Glu Ile Lys
            100                 105

<210> SEQ ID NO 54
<211> LENGTH: 6
<212> TYPE: PRT
<213> ORGANISM: Artificial Sequence
<220> FEATURE:
<223> OTHER INFORMATION: M2aM14173N LCDR1

<400> SEQUENCE: 54

Glu Asn Ile Tyr Ser Tyr
1               5

<210> SEQ ID NO 55
<211> LENGTH: 3
<212> TYPE: PRT
<213> ORGANISM: Artificial Sequence
<220> FEATURE:
<223> OTHER INFORMATION: M2aM14173N LCDR2

<400> SEQUENCE: 55

Asn Ala Glu
1
```

<210> SEQ ID NO 56
<211> LENGTH: 9
<212> TYPE: PRT
<213> ORGANISM: Artificial Sequence
<220> FEATURE:
<223> OTHER INFORMATION: M2aM14173N LCDR3

<400> SEQUENCE: 56

Gln His His Tyr Ser Ser Pro Trp Thr
1               5

<210> SEQ ID NO 57
<211> LENGTH: 330
<212> TYPE: PRT
<213> ORGANISM: Artificial Sequence
<220> FEATURE:
<223> OTHER INFORMATION: Mouse IgG2a

<400> SEQUENCE: 57

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn

```
                    290                 295                 300
Ser Tyr Ser Cys Ser Val Val His Glu Gly Leu His Asn His His Thr
305                 310                 315                 320

Thr Lys Ser Phe Ser Arg Thr Pro Gly Lys
                325                 330
```

<210> SEQ ID NO 58
<211> LENGTH: 107
<212> TYPE: PRT
<213> ORGANISM: Artificial Sequence
<220> FEATURE:
<223> OTHER INFORMATION: Constant LC

<400> SEQUENCE: 58

```
Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Gly Glu Cys
            100                 105
```

<210> SEQ ID NO 59
<211> LENGTH: 119
<212> TYPE: PRT
<213> ORGANISM: Artificial Sequence
<220> FEATURE:
<223> OTHER INFORMATION: M2aM14178N HCVR

<400> SEQUENCE: 59

```
Glu Val Gln Leu Val Glu Ser Gly Gly Gly Leu Val Lys Pro Gly Gly
1               5                   10                  15

Ser Leu Lys Leu Ser Cys Thr Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Asn Ile Ser Asp Gly Gly Thr Tyr Thr Tyr Tyr Pro Asp Asn Ile
50                  55                  60

Lys Gly Arg Phe Thr Ile Ser Arg Asp Asn Ala Lys Asn Asn Leu Tyr
65                  70                  75                  80

Leu Gln Met Ser His Leu Glu Ser Glu Asp Thr Ala Met Tyr Tyr Cys
                85                  90                  95

Ile Arg Gly Asp Val Tyr Tyr Val Arg Phe Ala Tyr Trp Gly Gln Gly
            100                 105                 110

Thr Leu Val Thr Val Ser Ala
        115
```

<210> SEQ ID NO 60
<211> LENGTH: 8
<212> TYPE: PRT
<213> ORGANISM: Artificial Sequence
<220> FEATURE:

<223> OTHER INFORMATION: M2aM14178N HCDR1

<400> SEQUENCE: 60

Gly Phe Thr Phe Ser Ser Tyr Ala
1               5

<210> SEQ ID NO 61
<211> LENGTH: 8
<212> TYPE: PRT
<213> ORGANISM: Artificial Sequence
<220> FEATURE:
<223> OTHER INFORMATION: M2aM14178N HCDR2

<400> SEQUENCE: 61

Ile Ser Asp Gly Gly Thr Tyr Thr
1               5

<210> SEQ ID NO 62
<211> LENGTH: 12
<212> TYPE: PRT
<213> ORGANISM: Artificial Sequence
<220> FEATURE:
<223> OTHER INFORMATION: M2aM14178N HCDR3

<400> SEQUENCE: 62

Ile Arg Gly Asp Val Tyr Tyr Val Arg Phe Ala Tyr
1               5                   10

<210> SEQ ID NO 63
<211> LENGTH: 109
<212> TYPE: PRT
<213> ORGANISM: Artificial Sequence
<220> FEATURE:
<223> OTHER INFORMATION: M2aM14178N LCVR

<400> SEQUENCE: 63

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Ser Ser
                20                  25                  30

Asn His Ala Asn Trp Val Gln Glu Lys Pro Asp His Leu Phe Thr Gly
            35                  40                  45

Leu Ile Gly Gly Thr Asn Asn Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp His Ser Asn
                85                  90                  95

His Trp Val Phe Gly Gly Gly Thr Lys Leu Thr Val Leu
                100                 105

<210> SEQ ID NO 64
<211> LENGTH: 9
<212> TYPE: PRT
<213> ORGANISM: Artificial Sequence
<220> FEATURE:
<223> OTHER INFORMATION: M2aM14178N LCDR1

<400> SEQUENCE: 64

Thr Gly Ala Val Thr Ser Ser Asn His
1               5

<210> SEQ ID NO 65

```
<211> LENGTH: 3
<212> TYPE: PRT
<213> ORGANISM: Artificial Sequence
<220> FEATURE:
<223> OTHER INFORMATION: M2aM14178N LCDR2

<400> SEQUENCE: 65

Gly Thr Asn
1

<210> SEQ ID NO 66
<211> LENGTH: 9
<212> TYPE: PRT
<213> ORGANISM: Artificial Sequence
<220> FEATURE:
<223> OTHER INFORMATION: M2aM14178N LCDR3

<400> SEQUENCE: 66

Ala Leu Trp His Ser Asn His Trp Val
1               5

<210> SEQ ID NO 67
<211> LENGTH: 106
<212> TYPE: PRT
<213> ORGANISM: Artificial Sequence
<220> FEATURE:
<223> OTHER INFORMATION: M2aM14178N Constant LC

<400> SEQUENCE: 67

Gly Gln Pro Lys Ser Ser Pro Ser Val Thr Leu Phe Pro Pro Ser Ser
1               5                   10                  15

Glu Glu Leu Glu Thr Asn Lys Ala Thr Leu Val Cys Thr Ile Thr Asp
                20                  25                  30

Phe Tyr Pro Gly Val Val Thr Val Asp Trp Lys Val Asp Gly Thr Pro
            35                  40                  45

Val Thr Gln Gly Met Glu Thr Thr Gln Pro Ser Lys Gln Ser Asn Asn
    50                  55                  60

Lys Tyr Met Ala Ser Ser Tyr Leu Thr Leu Thr Ala Arg Ala Trp Glu
65                  70                  75                  80

Arg His Ser Ser Tyr Ser Cys Gln Val Thr His Glu Gly His Thr Val
                85                  90                  95

Glu Lys Ser Leu Ser Arg Ala Asp Cys Ser
                100                 105

<210> SEQ ID NO 68
<211> LENGTH: 119
<212> TYPE: PRT
<213> ORGANISM: Artificial Sequence
<220> FEATURE:
<223> OTHER INFORMATION: M2aM14179N HCVR

<400> SEQUENCE: 68

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Leu Thr Asp Tyr
                20                  25                  30

Tyr Met Asn Trp Val Lys Gln Ser His Gly Lys Ser Leu Glu Trp Ile
            35                  40                  45

Gly Asp Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80
```

```
Met Glu Leu Arg Ser Leu Thr Ser Glu Asp Ser Ala Val Tyr Tyr Cys
            85                  90                  95

Ala Arg Gly Ala Tyr Tyr Ser Asn Tyr Phe Asp Tyr Trp Gly Gln Gly
        100                 105                 110

Thr Thr Leu Thr Val Ser Ser
        115

<210> SEQ ID NO 69
<211> LENGTH: 8
<212> TYPE: PRT
<213> ORGANISM: Artificial Sequence
<220> FEATURE:
<223> OTHER INFORMATION: M2aM14179N HCDR1

<400> SEQUENCE: 69

Gly Tyr Thr Leu Thr Asp Tyr Tyr
1               5

<210> SEQ ID NO 70
<211> LENGTH: 8
<212> TYPE: PRT
<213> ORGANISM: Artificial Sequence
<220> FEATURE:
<223> OTHER INFORMATION: M2aM14179N HCDR2

<400> SEQUENCE: 70

Ile Asn Pro Asn Asn Gly Gly Thr
1               5

<210> SEQ ID NO 71
<211> LENGTH: 12
<212> TYPE: PRT
<213> ORGANISM: Artificial Sequence
<220> FEATURE:
<223> OTHER INFORMATION: M2aM14179N HCDR3

<400> SEQUENCE: 71

Ala Arg Gly Ala Tyr Tyr Ser Asn Tyr Phe Asp Tyr
1               5                   10

<210> SEQ ID NO 72
<211> LENGTH: 112
<212> TYPE: PRT
<213> ORGANISM: Artificial Sequence
<220> FEATURE:
<223> OTHER INFORMATION: M2aM14179N LCVR

<400> SEQUENCE: 72

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Ile Leu Phe Thr Phe Gly Ser Gly Thr Gln Leu Glu Ile Lys
            100                 105                 110
```

<210> SEQ ID NO 73
<211> LENGTH: 12
<212> TYPE: PRT
<213> ORGANISM: Artificial Sequence
<220> FEATURE:
<223> OTHER INFORMATION: M2aM14179N LCDR1

<400> SEQUENCE: 73

Gln Ser Leu Leu Asn Ser Arg Thr Arg Lys Asn Tyr
1               5                   10

<210> SEQ ID NO 74
<211> LENGTH: 3
<212> TYPE: PRT
<213> ORGANISM: Artificial Sequence
<220> FEATURE:
<223> OTHER INFORMATION: M2aM14179N LCDR2

<400> SEQUENCE: 74

Trp Ala Ser
1

<210> SEQ ID NO 75
<211> LENGTH: 8
<212> TYPE: PRT
<213> ORGANISM: Artificial Sequence
<220> FEATURE:
<223> OTHER INFORMATION: M2aM14179N LCDR3

<400> SEQUENCE: 75

Lys Gln Ser Tyr Ile Leu Phe Thr
1               5

<210> SEQ ID NO 76
<211> LENGTH: 427
<212> TYPE: PRT
<213> ORGANISM: Artificial Sequence
<220> FEATURE:
<223> OTHER INFORMATION: TrkB(C32-H430).mmH
     aa 1-399: aa 32 through 430 of NP_001018074.1; aa
     400-427 myc-myc-hexahistidine tag

<400> SEQUENCE: 76

Cys Pro Thr Ser Cys Lys Cys Ser Ala Ser Arg Ile Trp Cys Ser Asp
1               5                   10                  15

Pro Ser Pro Gly Ile Val Ala Phe Pro Arg Leu Glu Pro Asn Ser Val
                20                  25                  30

Asp Pro Glu Asn Ile Thr Glu Ile Phe Ile Ala Asn Gln Lys Arg Leu
            35                  40                  45

Glu Ile Ile Asn Glu Asp Val Glu Ala Tyr Val Gly Leu Arg Asn
        50                  55                  60

Leu Thr Ile Val Asp Ser Gly Leu Lys Phe Val Ala His Lys Ala Phe
65                  70                  75                  80

Leu Lys Asn Ser Asn Leu Gln His Ile Asn Phe Thr Arg Asn Lys Leu
                85                  90                  95

Thr Ser Leu Ser Arg Lys His Phe Arg His Leu Asp Leu Ser Glu Leu
            100                 105                 110

Ile Leu Val Gly Asn Pro Phe Thr Cys Ser Cys Asp Ile Met Trp Ile
        115                 120                 125

Lys Thr Leu Gln Glu Ala Lys Ser Ser Pro Asp Thr Gln Asp Leu Tyr
    130                 135                 140

```
Cys Leu Asn Glu Ser Ser Lys Asn Ile Pro Leu Ala Asn Leu Gln Ile
145                 150                 155                 160

Pro Asn Cys Gly Leu Pro Ser Ala Asn Leu Ala Ala Pro Asn Leu Thr
            165                 170                 175

Val Glu Glu Gly Lys Ser Ile Thr Leu Ser Cys Ser Val Ala Gly Asp
        180                 185                 190

Pro Val Pro Asn Met Tyr Trp Asp Val Gly Asn Leu Val Ser Lys His
    195                 200                 205

Met Asn Glu Thr Ser His Thr Gln Gly Ser Leu Arg Ile Thr Asn Ile
210                 215                 220

Ser Ser Asp Asp Ser Gly Lys Gln Ile Ser Cys Val Ala Glu Asn Leu
225                 230                 235                 240

Val Gly Glu Asp Gln Asp Ser Val Asn Leu Thr Val His Phe Ala Pro
            245                 250                 255

Thr Ile Thr Phe Leu Glu Ser Pro Thr Ser Asp His His Trp Cys Ile
        260                 265                 270

Pro Phe Thr Val Lys Gly Asn Pro Lys Pro Ala Leu Gln Trp Phe Tyr
    275                 280                 285

Asn Gly Ala Ile Leu Asn Glu Ser Lys Tyr Ile Cys Thr Lys Ile His
290                 295                 300

Val Thr Asn His Thr Glu Tyr His Gly Cys Leu Gln Leu Asp Asn Pro
305                 310                 315                 320

Thr His Met Asn Asn Gly Asp Tyr Thr Leu Ile Ala Lys Asn Glu Tyr
            325                 330                 335

Gly Lys Asp Glu Lys Gln Ile Ser Ala His Phe Met Gly Trp Pro Gly
        340                 345                 350

Ile Asp Asp Gly Ala Asn Pro Asn Tyr Pro Asp Val Ile Tyr Glu Asp
    355                 360                 365

Tyr Gly Thr Ala Ala Asn Asp Ile Gly Asp Thr Thr Asn Arg Ser Asn
370                 375                 380

Glu Ile Pro Ser Thr Asp Val Thr Asp Lys Thr Gly Arg Glu His Glu
385                 390                 395                 400

Gln Lys Leu Ile Ser Glu Glu Asp Leu Gly Gly Glu Gln Lys Leu Ile
            405                 410                 415

Ser Glu Glu Asp Leu His His His His His His
        420                 425

<210> SEQ ID NO 77
<211> LENGTH: 632
<212> TYPE: PRT
<213> ORGANISM: Artificial Sequence
<220> FEATURE:
<223> OTHER INFORMATION: Human TrkB (C32-H430).mFc
      aa 1-399: aa 32 through 430 of NP_001018074.1; aa
      400-632 mouse Fc domain

<400> SEQUENCE: 77

Cys Pro Thr Ser Cys Lys Cys Ser Ala Ser Arg Ile Trp Cys Ser Asp
1               5                   10                  15

Pro Ser Pro Gly Ile Val Ala Phe Pro Arg Leu Glu Pro Asn Ser Val
            20                  25                  30

Asp Pro Glu Asn Ile Thr Glu Ile Phe Ile Ala Asn Gln Lys Arg Leu
        35                  40                  45

Glu Ile Ile Asn Glu Asp Asp Val Glu Ala Tyr Val Gly Leu Arg Asn
    50                  55                  60

Leu Thr Ile Val Asp Ser Gly Leu Lys Phe Val Ala His Lys Ala Phe
```

```
                65                  70                  75                  80
        Leu Lys Asn Ser Asn Leu Gln His Ile Asn Phe Thr Arg Asn Lys Leu
                        85                  90                  95

Thr Ser Leu Ser Arg Lys His Phe Arg His Leu Asp Leu Ser Glu Leu
                       100                 105                 110

Ile Leu Val Gly Asn Pro Phe Thr Cys Ser Cys Asp Ile Met Trp Ile
                       115                 120                 125

Lys Thr Leu Gln Glu Ala Lys Ser Ser Pro Asp Thr Gln Asp Leu Tyr
                       130                 135                 140

Cys Leu Asn Glu Ser Ser Lys Asn Ile Pro Leu Ala Asn Leu Gln Ile
        145                 150                 155                 160

Pro Asn Cys Gly Leu Pro Ser Ala Asn Leu Ala Ala Pro Asn Leu Thr
                       165                 170                 175

Val Glu Glu Gly Lys Ser Ile Thr Leu Ser Cys Ser Val Ala Gly Asp
                       180                 185                 190

Pro Val Pro Asn Met Tyr Trp Asp Val Gly Asn Leu Val Ser Lys His
                       195                 200                 205

Met Asn Glu Thr Ser His Thr Gln Gly Ser Leu Arg Ile Thr Asn Ile
                       210                 215                 220

Ser Ser Asp Asp Ser Gly Lys Gln Ile Ser Cys Val Ala Glu Asn Leu
        225                 230                 235                 240

Val Gly Glu Asp Gln Asp Ser Val Asn Leu Thr Val His Phe Ala Pro
                       245                 250                 255

Thr Ile Thr Phe Leu Glu Ser Pro Thr Ser Asp His His Trp Cys Ile
                       260                 265                 270

Pro Phe Thr Val Lys Gly Asn Pro Lys Pro Ala Leu Gln Trp Phe Tyr
                       275                 280                 285

Asn Gly Ala Ile Leu Asn Glu Ser Lys Tyr Ile Cys Thr Lys Ile His
                       290                 295                 300

Val Thr Asn His Thr Glu Tyr His Gly Cys Leu Gln Leu Asp Asn Pro
        305                 310                 315                 320

Thr His Met Asn Asn Gly Asp Tyr Thr Leu Ile Ala Lys Asn Glu Tyr
                       325                 330                 335

Gly Lys Asp Glu Lys Gln Ile Ser Ala His Phe Met Gly Trp Pro Gly
                       340                 345                 350

Ile Asp Asp Gly Ala Asn Pro Asn Tyr Pro Asp Val Ile Tyr Glu Asp
                       355                 360                 365

Tyr Gly Thr Ala Ala Asn Asp Ile Gly Asp Thr Thr Asn Arg Ser Asn
        370                 375                 380

Glu Ile Pro Ser Thr Asp Val Thr Asp Lys Thr Gly Arg Glu His Glu
        385                 390                 395                 400

Pro Arg Gly Pro Thr Ile Lys Pro Cys Pro Pro Cys Lys Cys Pro Ala
                       405                 410                 415

Pro Asn Leu Leu Gly Gly Pro Ser Val Phe Ile Phe Pro Pro Lys Ile
                       420                 425                 430

Lys Asp Val Leu Met Ile Ser Leu Ser Pro Ile Val Thr Cys Val Val
                       435                 440                 445

Val Asp Val Ser Glu Asp Asp Pro Asp Val Gln Ile Ser Trp Phe Val
                       450                 455                 460

Asn Asn Val Glu Val His Thr Ala Gln Thr Gln Thr His Arg Glu Asp
        465                 470                 475                 480

Tyr Asn Ser Thr Leu Arg Val Val Ser Ala Leu Pro Ile Gln His Gln
                       485                 490                 495
```

```
Asp Trp Met Ser Gly Lys Glu Phe Lys Cys Lys Val Asn Asn Lys Asp
            500                 505                 510

Leu Pro Ala Pro Ile Glu Arg Thr Ile Ser Lys Pro Lys Gly Ser Val
        515                 520                 525

Arg Ala Pro Gln Val Tyr Val Leu Pro Pro Glu Glu Met Thr
    530                 535                 540

Lys Lys Gln Val Thr Leu Thr Cys Met Val Thr Asp Phe Met Pro Glu
545                 550                 555                 560

Asp Ile Tyr Val Glu Trp Thr Asn Asn Gly Lys Thr Glu Leu Asn Tyr
                565                 570                 575

Lys Asn Thr Glu Pro Val Leu Asp Ser Asp Gly Ser Tyr Phe Met Tyr
            580                 585                 590

Ser Lys Leu Arg Val Glu Lys Lys Asn Trp Val Glu Arg Asn Ser Tyr
        595                 600                 605

Ser Cys Ser Val Val His Glu Gly Leu His Asn His Thr Thr Lys
    610                 615                 620

Ser Phe Ser Arg Thr Pro Gly Lys
625                 630

<210> SEQ ID NO 78
<211> LENGTH: 626
<212> TYPE: PRT
<213> ORGANISM: Artificial Sequence
<220> FEATURE:
<223> OTHER INFORMATION: Human TrkB (C32-H430).hFc
      aa 1-399: aa 32 through 430 of NP_001018074.1; aa
      400-626: human Fc domain

<400> SEQUENCE: 78

Cys Pro Thr Ser Cys Lys Cys Ser Ala Ser Arg Ile Trp Cys Ser Asp
1               5                   10                  15

Pro Ser Pro Gly Ile Val Ala Phe Pro Arg Leu Glu Pro Asn Ser Val
            20                  25                  30

Asp Pro Glu Asn Ile Thr Glu Ile Phe Ile Ala Asn Gln Lys Arg Leu
        35                  40                  45

Glu Ile Ile Asn Glu Asp Asp Val Glu Ala Tyr Val Gly Leu Arg Asn
    50                  55                  60

Leu Thr Ile Val Asp Ser Gly Leu Lys Phe Val Ala His Lys Ala Phe
65                  70                  75                  80

Leu Lys Asn Ser Asn Leu Gln His Ile Asn Phe Thr Arg Asn Lys Leu
                85                  90                  95

Thr Ser Leu Ser Arg Lys His Phe Arg His Leu Asp Leu Ser Glu Leu
            100                 105                 110

Ile Leu Val Gly Asn Pro Phe Thr Cys Ser Cys Asp Ile Met Trp Ile
        115                 120                 125

Lys Thr Leu Gln Glu Ala Lys Ser Ser Pro Asp Thr Gln Asp Leu Tyr
130                 135                 140

Cys Leu Asn Glu Ser Ser Lys Asn Ile Pro Leu Ala Asn Leu Gln Ile
145                 150                 155                 160

Pro Asn Cys Gly Leu Pro Ser Ala Asn Leu Ala Ala Pro Asn Leu Thr
                165                 170                 175

Val Glu Glu Gly Lys Ser Ile Thr Leu Ser Cys Ser Val Ala Gly Asp
            180                 185                 190

Pro Val Pro Asn Met Tyr Trp Asp Val Gly Asn Leu Val Ser Lys His
        195                 200                 205
```

-continued

```
Met Asn Glu Thr Ser His Thr Gln Gly Ser Leu Arg Ile Thr Asn Ile
    210                 215                 220
Ser Ser Asp Asp Ser Gly Lys Gln Ile Ser Cys Val Ala Glu Asn Leu
225                 230                 235                 240
Val Gly Glu Asp Gln Asp Ser Val Asn Leu Thr Val His Phe Ala Pro
                245                 250                 255
Thr Ile Thr Phe Leu Glu Ser Pro Thr Ser Asp His His Trp Cys Ile
            260                 265                 270
Pro Phe Thr Val Lys Gly Asn Pro Lys Pro Ala Leu Gln Trp Phe Tyr
        275                 280                 285
Asn Gly Ala Ile Leu Asn Glu Ser Lys Tyr Ile Cys Thr Lys Ile His
290                 295                 300
Val Thr Asn His Thr Glu Tyr His Gly Cys Leu Gln Leu Asp Asn Pro
305                 310                 315                 320
Thr His Met Asn Asn Gly Asp Tyr Thr Leu Ile Ala Lys Asn Glu Tyr
                325                 330                 335
Gly Lys Asp Glu Lys Gln Ile Ser Ala His Phe Met Gly Trp Pro Gly
            340                 345                 350
Ile Asp Asp Gly Ala Asn Pro Asn Tyr Pro Asp Val Ile Tyr Glu Asp
        355                 360                 365
Tyr Gly Thr Ala Ala Asn Asp Ile Gly Asp Thr Thr Asn Arg Ser Asn
    370                 375                 380
Glu Ile Pro Ser Thr Asp Val Thr Asp Lys Thr Gly Arg Glu His Asp
385                 390                 395                 400
Lys Thr His Thr Cys Pro Pro Cys Pro Ala Pro Glu Leu Leu Gly Gly
                405                 410                 415
Pro Ser Val Phe Leu Phe Pro Pro Lys Pro Lys Asp Thr Leu Met Ile
            420                 425                 430
Ser Arg Thr Pro Glu Val Thr Cys Val Val Val Asp Val Ser His Glu
        435                 440                 445
Asp Pro Glu Val Lys Phe Asn Trp Tyr Val Asp Gly Val Glu Val His
    450                 455                 460
Asn Ala Lys Thr Lys Pro Arg Glu Glu Gln Tyr Asn Ser Thr Tyr Arg
465                 470                 475                 480
Val Val Ser Val Leu Thr Val Leu His Gln Asp Trp Leu Asn Gly Lys
                485                 490                 495
Glu Tyr Lys Cys Lys Val Ser Asn Lys Ala Leu Pro Ala Pro Ile Glu
            500                 505                 510
Lys Thr Ile Ser Lys Ala Lys Gly Gln Pro Arg Glu Pro Gln Val Tyr
        515                 520                 525
Thr Leu Pro Pro Ser Arg Asp Glu Leu Thr Lys Asn Gln Val Ser Leu
    530                 535                 540
Thr Cys Leu Val Lys Gly Phe Tyr Pro Ser Asp Ile Ala Val Glu Trp
545                 550                 555                 560
Glu Ser Asn Gly Gln Pro Glu Asn Asn Tyr Lys Thr Thr Pro Pro Val
                565                 570                 575
Leu Asp Ser Asp Gly Ser Phe Phe Leu Tyr Ser Lys Leu Thr Val Asp
            580                 585                 590
Lys Ser Arg Trp Gln Gln Gly Asn Val Phe Ser Cys Ser Val Met His
        595                 600                 605
Glu Ala Leu His Asn His Tyr Thr Gln Lys Ser Leu Ser Leu Ser Pro
    610                 615                 620
Gly Lys
```

-continued

```
<210> SEQ ID NO 79
<211> LENGTH: 426
<212> TYPE: PRT
<213> ORGANISM: Artificial Sequence
<220> FEATURE:
<223> OTHER INFORMATION: Mouse TrkB (C32-H429)mmH
      aa 1-398: aa 32 through 429 of NP_001020245; aa
      399-426: myc-myc-hexahistidine tag

<400> SEQUENCE: 79

Cys Pro Thr Ser Cys Lys Cys Ser Ser Ala Arg Ile Trp Cys Thr Glu
1               5                   10                  15

Pro Ser Pro Gly Ile Val Ala Phe Pro Arg Leu Glu Pro Asn Ser Val
            20                  25                  30

Asp Pro Glu Asn Ile Thr Glu Ile Leu Ile Ala Asn Gln Lys Arg Leu
        35                  40                  45

Glu Ile Ile Asn Glu Asp Asp Val Glu Ala Tyr Val Gly Leu Arg Asn
    50                  55                  60

Leu Thr Ile Val Asp Ser Gly Leu Lys Phe Val Ala Tyr Lys Ala Phe
65                  70                  75                  80

Leu Lys Asn Ser Asn Leu Arg His Ile Asn Phe Thr Arg Asn Lys Leu
                85                  90                  95

Thr Ser Leu Ser Arg Arg His Phe Arg His Leu Asp Leu Ser Asp Leu
            100                 105                 110

Ile Leu Thr Gly Asn Pro Phe Thr Cys Ser Cys Asp Ile Met Trp Leu
        115                 120                 125

Lys Thr Leu Gln Glu Thr Lys Ser Ser Pro Asp Thr Gln Asp Leu Tyr
    130                 135                 140

Cys Leu Asn Glu Ser Ser Lys Asn Met Pro Leu Ala Asn Leu Gln Ile
145                 150                 155                 160

Pro Asn Cys Gly Leu Pro Ser Ala Arg Leu Ala Ala Pro Asn Leu Thr
                165                 170                 175

Val Glu Glu Gly Lys Ser Val Thr Leu Ser Cys Ser Val Gly Gly Asp
            180                 185                 190

Pro Leu Pro Thr Leu Tyr Trp Asp Val Gly Asn Leu Val Ser Lys His
        195                 200                 205

Met Asn Glu Thr Ser His Thr Gln Gly Ser Leu Arg Ile Thr Asn Ile
    210                 215                 220

Ser Ser Asp Asp Ser Gly Lys Gln Ile Ser Cys Val Ala Glu Asn Leu
225                 230                 235                 240

Val Gly Glu Asp Gln Asp Ser Val Asn Leu Thr Val His Phe Ala Pro
                245                 250                 255

Thr Ile Thr Phe Leu Glu Ser Pro Thr Ser Asp His His Trp Cys Ile
            260                 265                 270

Pro Phe Thr Val Arg Gly Asn Pro Lys Pro Ala Leu Gln Trp Phe Tyr
        275                 280                 285

Asn Gly Ala Ile Leu Asn Glu Ser Lys Tyr Ile Cys Thr Lys Ile His
    290                 295                 300

Val Thr Asn His Thr Glu Tyr His Gly Cys Leu Gln Leu Asp Asn Pro
305                 310                 315                 320

Thr His Met Asn Asn Gly Asp Tyr Thr Leu Met Ala Lys Asn Glu Tyr
                325                 330                 335

Gly Lys Asp Glu Arg Gln Ile Ser Ala His Phe Met Gly Arg Pro Gly
            340                 345                 350
```

Val Asp Tyr Glu Thr Asn Pro Asn Tyr Pro Glu Val Leu Tyr Glu Asp
    355                 360                 365

Trp Thr Thr Pro Thr Asp Ile Gly Asp Thr Thr Asn Lys Ser Asn Glu
370                 375                 380

Ile Pro Ser Thr Asp Val Ala Asp Gln Ser Asn Arg Glu His Glu Gln
385                 390                 395                 400

Lys Leu Ile Ser Glu Glu Asp Leu Gly Gly Glu Gln Lys Leu Ile Ser
                405                 410                 415

Glu Glu Asp Leu His His His His His His
            420                 425

<210> SEQ ID NO 80
<211> LENGTH: 631
<212> TYPE: PRT
<213> ORGANISM: Artificial Sequence
<220> FEATURE:
<223> OTHER INFORMATION: Mouse TrkB (C32-H429).mFc
      aa 1-398: aa 32 through 429 of NP_001020245; aa
      399-631 Mouse Fc domain

<400> SEQUENCE: 80

Cys Pro Thr Ser Cys Lys Cys Ser Ser Ala Arg Ile Trp Cys Thr Glu
1               5                   10                  15

Pro Ser Pro Gly Ile Val Ala Phe Pro Arg Leu Glu Pro Asn Ser Val
            20                  25                  30

Asp Pro Glu Asn Ile Thr Glu Ile Leu Ile Ala Asn Gln Lys Arg Leu
        35                  40                  45

Glu Ile Ile Asn Glu Asp Asp Val Glu Ala Tyr Val Gly Leu Arg Asn
    50                  55                  60

Leu Thr Ile Val Asp Ser Gly Leu Lys Phe Val Ala Tyr Lys Ala Phe
65                  70                  75                  80

Leu Lys Asn Ser Asn Leu Arg His Ile Asn Phe Thr Arg Asn Lys Leu
                85                  90                  95

Thr Ser Leu Ser Arg Arg His Phe Arg His Leu Asp Leu Ser Asp Leu
            100                 105                 110

Ile Leu Thr Gly Asn Pro Phe Thr Cys Ser Cys Asp Ile Met Trp Leu
        115                 120                 125

Lys Thr Leu Gln Glu Thr Lys Ser Ser Pro Asp Thr Gln Asp Leu Tyr
    130                 135                 140

Cys Leu Asn Glu Ser Ser Lys Asn Met Pro Leu Ala Asn Leu Gln Ile
145                 150                 155                 160

Pro Asn Cys Gly Leu Pro Ser Ala Arg Leu Ala Ala Pro Asn Leu Thr
                165                 170                 175

Val Glu Glu Gly Lys Ser Val Thr Leu Ser Cys Ser Val Gly Gly Asp
            180                 185                 190

Pro Leu Pro Thr Leu Tyr Trp Asp Val Gly Asn Leu Val Ser Lys His
        195                 200                 205

Met Asn Glu Thr Ser His Thr Gln Gly Ser Leu Arg Ile Thr Asn Ile
    210                 215                 220

Ser Ser Asp Asp Ser Gly Lys Gln Ile Ser Cys Val Ala Glu Asn Leu
225                 230                 235                 240

Val Gly Glu Asp Gln Asp Ser Val Asn Leu Thr Val His Phe Ala Pro
                245                 250                 255

Thr Ile Thr Phe Leu Glu Ser Pro Thr Ser Asp His His Trp Cys Ile
            260                 265                 270

```
Pro Phe Thr Val Arg Gly Asn Pro Lys Pro Ala Leu Gln Trp Phe Tyr
            275                 280                 285

Asn Gly Ala Ile Leu Asn Glu Ser Lys Tyr Ile Cys Thr Lys Ile His
        290                 295                 300

Val Thr Asn His Thr Glu Tyr His Gly Cys Leu Gln Leu Asp Asn Pro
305                 310                 315                 320

Thr His Met Asn Asn Gly Asp Tyr Thr Leu Met Ala Lys Asn Glu Tyr
                325                 330                 335

Gly Lys Asp Glu Arg Gln Ile Ser Ala His Phe Met Gly Arg Pro Gly
            340                 345                 350

Val Asp Tyr Glu Thr Asn Pro Asn Tyr Pro Glu Val Leu Tyr Glu Asp
        355                 360                 365

Trp Thr Thr Pro Thr Asp Ile Gly Asp Thr Thr Asn Lys Ser Asn Glu
370                 375                 380

Ile Pro Ser Thr Asp Val Ala Asp Gln Ser Asn Arg Glu His Glu Pro
385                 390                 395                 400

Arg Gly Pro Thr Ile Lys Pro Cys Pro Pro Cys Lys Cys Pro Ala Pro
            405                 410                 415

Asn Leu Leu Gly Gly Pro Ser Val Phe Ile Phe Pro Pro Lys Ile Lys
        420                 425                 430

Asp Val Leu Met Ile Ser Leu Ser Pro Ile Val Thr Cys Val Val Val
435                 440                 445

Asp Val Ser Glu Asp Asp Pro Asp Val Gln Ile Ser Trp Phe Val Asn
        450                 455                 460

Asn Val Glu Val His Thr Ala Gln Thr Gln Thr His Arg Glu Asp Tyr
465                 470                 475                 480

Asn Ser Thr Leu Arg Val Val Ser Ala Leu Pro Ile Gln His Gln Asp
            485                 490                 495

Trp Met Ser Gly Lys Glu Phe Lys Cys Lys Val Asn Asn Lys Asp Leu
        500                 505                 510

Pro Ala Pro Ile Glu Arg Thr Ile Ser Lys Pro Lys Gly Ser Val Arg
            515                 520                 525

Ala Pro Gln Val Tyr Val Leu Pro Pro Pro Glu Glu Glu Met Thr Lys
        530                 535                 540

Lys Gln Val Thr Leu Thr Cys Met Val Thr Asp Phe Met Pro Glu Asp
545                 550                 555                 560

Ile Tyr Val Glu Trp Thr Asn Asn Gly Lys Thr Glu Leu Asn Tyr Lys
                565                 570                 575

Asn Thr Glu Pro Val Leu Asp Ser Asp Gly Ser Tyr Phe Met Tyr Ser
            580                 585                 590

Lys Leu Arg Val Glu Lys Lys Asn Trp Val Glu Arg Asn Ser Tyr Ser
        595                 600                 605

Cys Ser Val Val His Glu Gly Leu His Asn His His Thr Thr Lys Ser
610                 615                 620

Phe Ser Arg Thr Pro Gly Lys
625                 630

<210> SEQ ID NO 81
<211> LENGTH: 625
<212> TYPE: PRT
<213> ORGANISM: Artificial Sequence
<220> FEATURE:
<223> OTHER INFORMATION: Mouse TrkB (C32-H429).hFc
      aa 1-398: aa 32 through 429 of NP_001020245; aa
      399-625 human Fc domain
```

<400> SEQUENCE: 81

```
Cys Pro Thr Ser Cys Lys Cys Ser Ser Ala Arg Ile Trp Cys Thr Glu
1               5                   10                  15
Pro Ser Pro Gly Ile Val Ala Phe Pro Arg Leu Glu Pro Asn Ser Val
            20                  25                  30
Asp Pro Glu Asn Ile Thr Glu Ile Leu Ile Ala Asn Gln Lys Arg Leu
        35                  40                  45
Glu Ile Ile Asn Glu Asp Asp Val Glu Ala Tyr Val Gly Leu Arg Asn
    50                  55                  60
Leu Thr Ile Val Asp Ser Gly Leu Lys Phe Val Ala Tyr Lys Ala Phe
65                  70                  75                  80
Leu Lys Asn Ser Asn Leu Arg His Ile Asn Phe Thr Arg Asn Lys Leu
                85                  90                  95
Thr Ser Leu Ser Arg Arg His Phe Arg His Leu Asp Leu Ser Asp Leu
            100                 105                 110
Ile Leu Thr Gly Asn Pro Phe Thr Cys Ser Cys Asp Ile Met Trp Leu
        115                 120                 125
Lys Thr Leu Gln Glu Thr Lys Ser Ser Pro Asp Thr Gln Asp Leu Tyr
    130                 135                 140
Cys Leu Asn Glu Ser Ser Lys Asn Met Pro Leu Ala Asn Leu Gln Ile
145                 150                 155                 160
Pro Asn Cys Gly Leu Pro Ser Ala Arg Leu Ala Ala Pro Asn Leu Thr
                165                 170                 175
Val Glu Glu Gly Lys Ser Val Thr Leu Ser Cys Ser Val Gly Gly Asp
            180                 185                 190
Pro Leu Pro Thr Leu Tyr Trp Asp Val Gly Asn Leu Val Ser Lys His
        195                 200                 205
Met Asn Glu Thr Ser His Thr Gln Gly Ser Leu Arg Ile Thr Asn Ile
    210                 215                 220
Ser Ser Asp Asp Ser Gly Lys Gln Ile Ser Cys Val Ala Glu Asn Leu
225                 230                 235                 240
Val Gly Glu Asp Gln Asp Ser Val Asn Leu Thr Val His Phe Ala Pro
                245                 250                 255
Thr Ile Thr Phe Leu Glu Ser Pro Thr Ser Asp His His Trp Cys Ile
            260                 265                 270
Pro Phe Thr Val Arg Gly Asn Pro Lys Pro Ala Leu Gln Trp Phe Tyr
        275                 280                 285
Asn Gly Ala Ile Leu Asn Glu Ser Lys Tyr Ile Cys Thr Lys Ile His
    290                 295                 300
Val Thr Asn His Thr Glu Tyr His Gly Cys Leu Gln Leu Asp Asn Pro
305                 310                 315                 320
Thr His Met Asn Asn Gly Asp Tyr Thr Leu Met Ala Lys Asn Glu Tyr
                325                 330                 335
Gly Lys Asp Glu Arg Gln Ile Ser Ala His Phe Met Gly Arg Pro Gly
            340                 345                 350
Val Asp Tyr Glu Thr Asn Pro Asn Tyr Pro Glu Val Leu Tyr Glu Asp
        355                 360                 365
Trp Thr Thr Pro Thr Asp Ile Gly Asp Thr Thr Asn Lys Ser Asn Glu
    370                 375                 380
Ile Pro Ser Thr Asp Val Ala Asp Gln Ser Asn Arg Glu His Asp Lys
385                 390                 395                 400
Thr His Thr Cys Pro Pro Cys Pro Ala Pro Glu Leu Leu Gly Gly Pro
                405                 410                 415
```

-continued

```
Ser Val Phe Leu Phe Pro Pro Lys Pro Lys Asp Thr Leu Met Ile Ser
            420             425             430
Arg Thr Pro Glu Val Thr Cys Val Val Asp Val Ser His Glu Asp
        435             440             445
Pro Glu Val Lys Phe Asn Trp Tyr Val Asp Gly Val Glu Val His Asn
    450             455             460
Ala Lys Thr Lys Pro Arg Glu Glu Gln Tyr Asn Ser Thr Tyr Arg Val
465             470             475             480
Val Ser Val Leu Thr Val Leu His Gln Asp Trp Leu Asn Gly Lys Glu
            485             490             495
Tyr Lys Cys Lys Val Ser Asn Lys Ala Leu Pro Ala Pro Ile Glu Lys
        500             505             510
Thr Ile Ser Lys Ala Lys Gly Gln Pro Arg Glu Pro Gln Val Tyr Thr
    515             520             525
Leu Pro Pro Ser Arg Asp Glu Leu Thr Lys Asn Gln Val Ser Leu Thr
530             535             540
Cys Leu Val Lys Gly Phe Tyr Pro Ser Asp Ile Ala Val Glu Trp Glu
545             550             555             560
Ser Asn Gly Gln Pro Glu Asn Asn Tyr Lys Thr Thr Pro Pro Val Leu
            565             570             575
Asp Ser Asp Gly Ser Phe Phe Leu Tyr Ser Lys Leu Thr Val Asp Lys
        580             585             590
Ser Arg Trp Gln Gln Gly Asn Val Phe Ser Cys Ser Val Met His Glu
    595             600             605
Ala Leu His Asn His Tyr Thr Gln Lys Ser Leu Ser Leu Ser Pro Gly
            610             615             620
Lys
625

<210> SEQ ID NO 82
<211> LENGTH: 427
<212> TYPE: PRT
<213> ORGANISM: Artificial Sequence
<220> FEATURE:
<223> OTHER INFORMATION: Rabbit TrkB (C32-H430)mmH
      aa 1-399: aa32 through 430 of XP_002721319.1; aa
      400-427: myc-myc-hexahistidine tag

<400> SEQUENCE: 82

Cys Pro Ala Ser Cys Thr Cys Ser Ala Ser Arg Ile Trp Cys Ser Asp
1               5                   10                  15
Pro Val Pro Gly Leu Met Ala Phe Pro Arg Leu Glu Pro Asn Ser Ala
            20                  25                  30
Asp Pro Glu Asn Ile Thr Glu Ile Phe Ile Ala Asn Gln Lys Lys Leu
        35                  40                  45
Glu Ile Ile Asn Glu Asp Asp Ile Glu Ala Tyr Val Gly Leu Arg Asn
    50                  55                  60
Leu Thr Ile Val Asp Ser Gly Leu Lys Phe Val Ala Tyr Lys Ala Phe
65                  70                  75                  80
Leu Lys Asn Ser Asn Leu Gln His Ile Asn Phe Thr Arg Asn Lys Leu
                85                  90                  95
Thr Ser Leu Ser Arg Lys His Phe Arg His Leu Asp Leu Ser Glu Leu
            100                 105                 110
Ile Leu Val Gly Asn Pro Phe Thr Cys Ser Cys Asp Ile Met Trp Ile
        115                 120                 125
```

Lys Thr Leu Gln Glu Thr Lys Ser Ser Pro Glu Thr Gln Asp Leu Tyr
            130                 135                 140

Cys Leu Asn Glu Ser Ser Lys Asn Ile Pro Leu Ala Asn Leu Gln Ile
145                 150                 155                 160

Pro Asn Cys Gly Leu Pro Ser Ala Ser Leu Ala Ala Pro Asn Leu Thr
                165                 170                 175

Val Glu Glu Gly Lys Ser Ile Thr Leu Ser Cys Asn Val Ala Gly Asp
            180                 185                 190

Pro Val Pro Asn Leu Tyr Trp Asp Val Gly Asn Leu Val Ser Lys His
                195                 200                 205

Met Asn Glu Thr Ser His Thr Gln Gly Phe Leu Arg Ile Thr Asn Ile
        210                 215                 220

Ser Ser Asp Asp Ser Gly Lys Gln Ile Ser Cys Val Ala Glu Asn Leu
225                 230                 235                 240

Val Gly Glu Asp Gln Asp Ser Val Asn Leu Thr Val His Phe Ala Pro
                245                 250                 255

Thr Ile Thr Phe Leu Glu Ser Pro Thr Ser Asp His His Trp Cys Ile
                260                 265                 270

Pro Phe Thr Val Lys Gly Asn Pro Lys Pro Thr Leu Gln Trp Phe Tyr
            275                 280                 285

Asn Gly Ala Ile Leu Asn Glu Ser Lys Tyr Ile Cys Thr Lys Ile His
        290                 295                 300

Val Thr Asn His Thr Glu Tyr His Gly Cys Leu Gln Leu Asp Asn Pro
305                 310                 315                 320

Thr His Met Asn Asn Gly Asp Tyr Thr Leu Ile Ala Lys Asn Glu Tyr
                325                 330                 335

Gly Lys Asp Glu Arg Gln Ile Ser Ala His Phe Met Gly Trp Pro Gly
            340                 345                 350

Ile Asp Asp Asp Pro Asn Leu Asn Tyr Pro Asp Val Ile Tyr Ala Asp
                355                 360                 365

Tyr Gly Thr Ala Ala Asn Asp Ile Gly Asp Thr Thr Asn Arg Ser Asn
        370                 375                 380

Glu Ile Pro Pro Thr Gly Ala Ala Asp Asn Ala Gly Arg Glu His Glu
385                 390                 395                 400

Gln Lys Leu Ile Ser Glu Glu Asp Leu Gly Gly Glu Gln Lys Leu Ile
                405                 410                 415

Ser Glu Glu Asp Leu His His His His His
            420                 425

<210> SEQ ID NO 83
<211> LENGTH: 632
<212> TYPE: PRT
<213> ORGANISM: Artificial Sequence
<220> FEATURE:
<223> OTHER INFORMATION: Rabbit TrkB (C32-H430)mFc
      aa 1-399: aa32 through 430 of XP_002721319.1; aa
      400-632 Mouse Fc domain

<400> SEQUENCE: 83

Cys Pro Ala Ser Cys Thr Cys Ser Ala Ser Arg Ile Trp Cys Ser Asp
1               5                   10                  15

Pro Val Pro Gly Leu Met Ala Phe Pro Arg Leu Glu Pro Asn Ser Ala
            20                  25                  30

Asp Pro Glu Asn Ile Thr Glu Ile Phe Ile Ala Asn Gln Lys Lys Leu
        35                  40                  45

Glu Ile Ile Asn Glu Asp Asp Ile Glu Ala Tyr Val Gly Leu Arg Asn

```
                50                  55                  60
Leu Thr Ile Val Asp Ser Gly Leu Lys Phe Val Ala Tyr Lys Ala Phe
 65                  70                  75                  80

Leu Lys Asn Ser Asn Leu Gln His Ile Asn Phe Thr Arg Asn Lys Leu
                     85                  90                  95

Thr Ser Leu Ser Arg Lys His Phe Arg His Leu Asp Leu Ser Glu Leu
                100                 105                 110

Ile Leu Val Gly Asn Pro Phe Thr Cys Ser Cys Asp Ile Met Trp Ile
                115                 120                 125

Lys Thr Leu Gln Glu Thr Lys Ser Ser Pro Glu Thr Gln Asp Leu Tyr
            130                 135                 140

Cys Leu Asn Glu Ser Ser Lys Asn Ile Pro Leu Ala Asn Leu Gln Ile
145                 150                 155                 160

Pro Asn Cys Gly Leu Pro Ser Ala Ser Leu Ala Ala Pro Asn Leu Thr
                165                 170                 175

Val Glu Glu Gly Lys Ser Ile Thr Leu Ser Cys Asn Val Ala Gly Asp
                180                 185                 190

Pro Val Pro Asn Leu Tyr Trp Asp Val Gly Asn Leu Val Ser Lys His
            195                 200                 205

Met Asn Glu Thr Ser His Thr Gln Gly Phe Leu Arg Ile Thr Asn Ile
    210                 215                 220

Ser Ser Asp Asp Ser Gly Lys Gln Ile Ser Cys Val Ala Glu Asn Leu
225                 230                 235                 240

Val Gly Glu Asp Gln Asp Ser Val Asn Leu Thr Val His Phe Ala Pro
                245                 250                 255

Thr Ile Thr Phe Leu Glu Ser Pro Thr Ser Asp His His Trp Cys Ile
                260                 265                 270

Pro Phe Thr Val Lys Gly Asn Pro Lys Pro Thr Leu Gln Trp Phe Tyr
            275                 280                 285

Asn Gly Ala Ile Leu Asn Glu Ser Lys Tyr Ile Cys Thr Lys Ile His
    290                 295                 300

Val Thr Asn His Thr Glu Tyr His Gly Cys Leu Gln Leu Asp Asn Pro
305                 310                 315                 320

Thr His Met Asn Asn Gly Asp Tyr Thr Leu Ile Ala Lys Asn Glu Tyr
                325                 330                 335

Gly Lys Asp Glu Arg Gln Ile Ser Ala His Phe Met Gly Trp Pro Gly
                340                 345                 350

Ile Asp Asp Asp Pro Asn Leu Asn Tyr Pro Asp Val Ile Tyr Ala Asp
            355                 360                 365

Tyr Gly Thr Ala Ala Asn Asp Ile Gly Asp Thr Thr Asn Arg Ser Asn
    370                 375                 380

Glu Ile Pro Pro Thr Gly Ala Ala Asp Asn Ala Gly Arg Glu His Glu
385                 390                 395                 400

Pro Arg Gly Pro Thr Ile Lys Pro Cys Pro Pro Cys Lys Cys Pro Ala
                405                 410                 415

Pro Asn Leu Leu Gly Gly Pro Ser Val Phe Ile Phe Pro Pro Lys Ile
                420                 425                 430

Lys Asp Val Leu Met Ile Ser Leu Ser Pro Ile Val Thr Cys Val Val
            435                 440                 445

Val Asp Val Ser Glu Asp Asp Pro Asp Val Gln Ile Ser Trp Phe Val
    450                 455                 460

Asn Asn Val Glu Val His Thr Ala Gln Thr Gln Thr His Arg Glu Asp
465                 470                 475                 480
```

```
Tyr Asn Ser Thr Leu Arg Val Ser Ala Leu Pro Ile Gln His Gln
                485                 490                 495

Asp Trp Met Ser Gly Lys Glu Phe Lys Cys Lys Val Asn Asn Lys Asp
            500                 505                 510

Leu Pro Ala Pro Ile Glu Arg Thr Ile Ser Lys Pro Lys Gly Ser Val
            515                 520                 525

Arg Ala Pro Gln Val Tyr Val Leu Pro Pro Glu Glu Met Thr
530                 535                 540

Lys Lys Gln Val Thr Leu Thr Cys Met Val Thr Asp Phe Met Pro Glu
545                 550                 555                 560

Asp Ile Tyr Val Glu Trp Thr Asn Asn Gly Lys Thr Glu Leu Asn Tyr
                565                 570                 575

Lys Asn Thr Glu Pro Val Leu Asp Ser Asp Gly Ser Tyr Phe Met Tyr
            580                 585                 590

Ser Lys Leu Arg Val Glu Lys Lys Asn Trp Val Glu Arg Asn Ser Tyr
            595                 600                 605

Ser Cys Ser Val Val His Glu Gly Leu His Asn His His Thr Thr Lys
        610                 615                 620

Ser Phe Ser Arg Thr Pro Gly Lys
625                 630

<210> SEQ ID NO 84
<211> LENGTH: 426
<212> TYPE: PRT
<213> ORGANISM: Artificial Sequence
<220> FEATURE:
<223> OTHER INFORMATION: Rat TrkB (C32-H429)mmH
      aa 1-398: aa 32 through 429 of NP_036863.1; aa
      399-426 myc-myc-hexahistidine tag

<400> SEQUENCE: 84

Cys Pro Met Ser Cys Lys Cys Ser Thr Thr Arg Ile Trp Cys Thr Glu
1               5                   10                  15

Pro Ser Pro Gly Ile Val Ala Phe Pro Arg Leu Glu Pro Asn Ser Ile
            20                  25                  30

Asp Pro Glu Asn Ile Thr Glu Ile Leu Ile Ala Asn Gln Lys Arg Leu
        35                  40                  45

Glu Ile Ile Asn Glu Asp Asp Val Glu Ala Tyr Val Gly Leu Lys Asn
    50                  55                  60

Leu Thr Ile Val Asp Ser Gly Leu Lys Phe Val Ala Tyr Lys Ala Phe
65                  70                  75                  80

Leu Lys Asn Gly Asn Leu Arg His Ile Asn Phe Thr Arg Asn Lys Leu
                85                  90                  95

Thr Ser Leu Ser Arg Arg His Phe Arg His Leu Asp Leu Ser Asp Leu
            100                 105                 110

Ile Leu Thr Gly Asn Pro Phe Thr Cys Ser Cys Asp Ile Met Trp Leu
        115                 120                 125

Lys Thr Leu Gln Glu Thr Lys Ser Ser Pro Asp Thr Gln Asp Leu Tyr
    130                 135                 140

Cys Leu Asn Glu Ser Ser Lys Asn Thr Pro Leu Ala Asn Leu Gln Ile
145                 150                 155                 160

Pro Asn Cys Gly Leu Pro Ser Ala Arg Leu Ala Ala Pro Asn Leu Thr
                165                 170                 175

Val Glu Glu Gly Lys Ser Val Thr Ile Ser Cys Ser Val Gly Gly Asp
            180                 185                 190
```

Pro Leu Pro Thr Leu Tyr Trp Asp Val Gly Asn Leu Val Ser Lys His
            195                 200                 205

Met Asn Glu Thr Ser His Thr Gln Gly Ser Leu Arg Ile Thr Asn Ile
    210                 215                 220

Ser Ser Asp Asp Ser Gly Lys Gln Ile Ser Cys Val Ala Glu Asn Leu
225                 230                 235                 240

Val Gly Glu Asp Gln Asp Ser Val Asn Leu Thr Val His Phe Ala Pro
            245                 250                 255

Thr Ile Thr Phe Leu Glu Ser Pro Thr Ser Asp His His Trp Cys Ile
                260                 265                 270

Pro Phe Thr Val Arg Gly Asn Pro Lys Pro Ala Leu Gln Trp Phe Tyr
            275                 280                 285

Asn Gly Ala Ile Leu Asn Glu Ser Lys Tyr Ile Cys Thr Lys Ile His
    290                 295                 300

Val Thr Asn His Thr Glu Tyr His Gly Cys Leu Gln Leu Asp Asn Pro
305                 310                 315                 320

Thr His Met Asn Asn Gly Asp Tyr Thr Leu Met Ala Lys Asn Glu Tyr
                325                 330                 335

Gly Lys Asp Glu Arg Gln Ile Ser Ala His Phe Met Gly Arg Pro Gly
            340                 345                 350

Val Asp Tyr Glu Thr Asn Pro Asn Tyr Pro Glu Val Leu Tyr Glu Asp
                355                 360                 365

Trp Thr Thr Pro Thr Asp Ile Gly Asp Thr Thr Asn Lys Ser Asn Glu
    370                 375                 380

Ile Pro Ser Thr Asp Val Ala Asp Gln Thr Asn Arg Glu His Glu Gln
385                 390                 395                 400

Lys Leu Ile Ser Glu Glu Asp Leu Gly Gly Glu Gln Lys Leu Ile Ser
                405                 410                 415

Glu Glu Asp Leu His His His His His His
            420                 425

<210> SEQ ID NO 85
<211> LENGTH: 631
<212> TYPE: PRT
<213> ORGANISM: Artificial Sequence
<220> FEATURE:
<223> OTHER INFORMATION: Rat TrkB (C32-H429)mFc
      aa 1-398: aa 32 through 429 of NP_036863.1; aa
      399-631 Mouse Fc domain

<400> SEQUENCE: 85

Cys Pro Met Ser Cys Lys Cys Ser Thr Thr Arg Ile Trp Cys Thr Glu
1               5                   10                  15

Pro Ser Pro Gly Ile Val Ala Phe Pro Arg Leu Glu Pro Asn Ser Ile
            20                  25                  30

Asp Pro Glu Asn Ile Thr Glu Ile Leu Ile Ala Asn Gln Lys Arg Leu
        35                  40                  45

Glu Ile Ile Asn Glu Asp Val Glu Ala Tyr Val Gly Leu Lys Asn
    50                  55                  60

Leu Thr Ile Val Asp Ser Gly Leu Lys Phe Val Ala Tyr Lys Ala Phe
65                  70                  75                  80

Leu Lys Asn Gly Asn Leu Arg His Ile Asn Phe Thr Arg Asn Lys Leu
                85                  90                  95

Thr Ser Leu Ser Arg Arg His Phe Arg His Leu Asp Leu Ser Asp Leu
            100                 105                 110

Ile Leu Thr Gly Asn Pro Phe Thr Cys Ser Cys Asp Ile Met Trp Leu

```
                115                 120                 125
Lys Thr Leu Gln Glu Thr Lys Ser Ser Pro Asp Thr Gln Asp Leu Tyr
    130                 135                 140

Cys Leu Asn Glu Ser Ser Lys Asn Thr Pro Leu Ala Asn Leu Gln Ile
145                 150                 155                 160

Pro Asn Cys Gly Leu Pro Ser Ala Arg Leu Ala Ala Pro Asn Leu Thr
                165                 170                 175

Val Glu Glu Gly Lys Ser Val Thr Ile Ser Cys Ser Val Gly Gly Asp
                180                 185                 190

Pro Leu Pro Thr Leu Tyr Trp Asp Val Gly Asn Leu Val Ser Lys His
                195                 200                 205

Met Asn Glu Thr Ser His Thr Gln Gly Ser Leu Arg Ile Thr Asn Ile
    210                 215                 220

Ser Ser Asp Asp Ser Gly Lys Gln Ile Ser Cys Val Ala Glu Asn Leu
225                 230                 235                 240

Val Gly Glu Asp Gln Asp Ser Val Asn Leu Thr Val His Phe Ala Pro
                245                 250                 255

Thr Ile Thr Phe Leu Glu Ser Pro Thr Ser Asp His His Trp Cys Ile
                260                 265                 270

Pro Phe Thr Val Arg Gly Asn Pro Lys Pro Ala Leu Gln Trp Phe Tyr
                275                 280                 285

Asn Gly Ala Ile Leu Asn Glu Ser Lys Tyr Ile Cys Thr Lys Ile His
    290                 295                 300

Val Thr Asn His Thr Glu Tyr His Gly Cys Leu Gln Leu Asp Asn Pro
305                 310                 315                 320

Thr His Met Asn Asn Gly Asp Tyr Thr Leu Met Ala Lys Asn Glu Tyr
                325                 330                 335

Gly Lys Asp Glu Arg Gln Ile Ser Ala His Phe Met Gly Arg Pro Gly
                340                 345                 350

Val Asp Tyr Glu Thr Asn Pro Asn Tyr Pro Glu Val Leu Tyr Glu Asp
                355                 360                 365

Trp Thr Thr Pro Thr Asp Ile Gly Asp Thr Thr Asn Lys Ser Asn Glu
    370                 375                 380

Ile Pro Ser Thr Asp Val Ala Asp Gln Thr Asn Arg Glu His Glu Pro
385                 390                 395                 400

Arg Gly Pro Thr Ile Lys Pro Cys Pro Pro Cys Lys Cys Pro Ala Pro
                405                 410                 415

Asn Leu Leu Gly Gly Pro Ser Val Phe Ile Phe Pro Pro Lys Ile Lys
                420                 425                 430

Asp Val Leu Met Ile Ser Leu Ser Pro Ile Val Thr Cys Val Val Val
                435                 440                 445

Asp Val Ser Glu Asp Asp Pro Asp Val Gln Ile Ser Trp Phe Val Asn
                450                 455                 460

Asn Val Glu Val His Thr Ala Gln Thr Gln Thr His Arg Glu Asp Tyr
465                 470                 475                 480

Asn Ser Thr Leu Arg Val Val Ser Ala Leu Pro Ile Gln His Gln Asp
                485                 490                 495

Trp Met Ser Gly Lys Glu Phe Lys Cys Lys Val Asn Asn Lys Asp Leu
                500                 505                 510

Pro Ala Pro Ile Glu Arg Thr Ile Ser Lys Pro Lys Gly Ser Val Arg
                515                 520                 525

Ala Pro Gln Val Tyr Val Leu Pro Pro Glu Glu Glu Met Thr Lys
                530                 535                 540
```

-continued

```
Lys Gln Val Thr Leu Thr Cys Met Val Thr Asp Phe Met Pro Glu Asp
545                 550                 555                 560

Ile Tyr Val Glu Trp Thr Asn Asn Gly Lys Thr Glu Leu Asn Tyr Lys
                565                 570                 575

Asn Thr Glu Pro Val Leu Asp Ser Asp Gly Ser Tyr Phe Met Tyr Ser
            580                 585                 590

Lys Leu Arg Val Glu Lys Lys Asn Trp Val Glu Arg Asn Ser Tyr Ser
        595                 600                 605

Cys Ser Val Val His Glu Gly Leu His Asn His His Thr Thr Lys Ser
    610                 615                 620

Phe Ser Arg Thr Pro Gly Lys
625                 630

<210> SEQ ID NO 86
<211> LENGTH: 605
<212> TYPE: PRT
<213> ORGANISM: Artificial Sequence
<220> FEATURE:
<223> OTHER INFORMATION: Human TrkA(A34-T414).hFc
      aa 1-375: aa 34 through 414 of NP_001012331.1 with
      V263L, C300S; aa 376-378 GPG Linker; aa 379-605
      human Fc domain

<400> SEQUENCE: 86

Ala Pro Cys Pro Asp Ala Cys Cys Pro His Gly Ser Ser Gly Leu Arg
1               5                   10                  15

Cys Thr Arg Asp Gly Ala Leu Asp Ser Leu His His Leu Pro Gly Ala
            20                  25                  30

Glu Asn Leu Thr Glu Leu Tyr Ile Glu Asn Gln Gln His Leu Gln His
        35                  40                  45

Leu Glu Leu Arg Asp Leu Arg Gly Leu Gly Glu Leu Arg Asn Leu Thr
    50                  55                  60

Ile Val Lys Ser Gly Leu Arg Phe Val Ala Pro Asp Ala Phe His Phe
65                  70                  75                  80

Thr Pro Arg Leu Ser Arg Leu Asn Leu Ser Phe Asn Ala Leu Glu Ser
                85                  90                  95

Leu Ser Trp Lys Thr Val Gln Gly Leu Ser Leu Gln Glu Leu Val Leu
            100                 105                 110

Ser Gly Asn Pro Leu His Cys Ser Cys Ala Leu Arg Trp Leu Gln Arg
        115                 120                 125

Trp Glu Glu Glu Gly Leu Gly Gly Val Pro Glu Gln Lys Leu Gln Cys
    130                 135                 140

His Gly Gln Gly Pro Leu Ala His Met Pro Asn Ala Ser Cys Gly Val
145                 150                 155                 160

Pro Thr Leu Lys Val Gln Val Pro Asn Ala Ser Val Asp Val Gly Asp
                165                 170                 175

Asp Val Leu Leu Arg Cys Gln Val Glu Gly Arg Gly Leu Glu Gln Ala
            180                 185                 190

Gly Trp Ile Leu Thr Glu Leu Glu Gln Ser Ala Thr Val Met Lys Ser
        195                 200                 205

Gly Gly Leu Pro Ser Leu Gly Leu Thr Leu Ala Asn Val Thr Ser Asp
    210                 215                 220

Leu Asn Arg Lys Asn Leu Thr Cys Trp Ala Glu Asn Asp Val Gly Arg
225                 230                 235                 240

Ala Glu Val Ser Val Gln Val Asn Val Ser Phe Pro Ala Ser Val Gln
                245                 250                 255
```

```
Leu His Thr Ala Val Glu Met His His Trp Ser Ile Pro Phe Ser Val
            260                 265                 270

Asp Gly Gln Pro Ala Pro Ser Leu Arg Trp Leu Phe Asn Gly Ser Val
            275                 280                 285

Leu Asn Glu Thr Ser Phe Ile Phe Thr Glu Phe Leu Glu Pro Ala Ala
            290                 295                 300

Asn Glu Thr Val Arg His Gly Cys Leu Arg Leu Asn Gln Pro Thr His
305                 310                 315                 320

Val Asn Asn Gly Asn Tyr Thr Leu Leu Ala Ala Asn Pro Phe Gly Gln
                325                 330                 335

Ala Ser Ala Ser Ile Met Ala Ala Phe Met Asp Asn Pro Phe Glu Phe
            340                 345                 350

Asn Pro Glu Asp Pro Ile Pro Asp Thr Asn Ser Thr Ser Gly Asp Pro
            355                 360                 365

Val Glu Lys Lys Asp Glu Thr Gly Pro Gly Asp Lys Thr His Thr Cys
            370                 375                 380

Pro Pro Cys Pro Ala Pro Glu Leu Leu Gly Gly Pro Ser Val Phe Leu
385                 390                 395                 400

Phe Pro Pro Lys Pro Lys Asp Thr Leu Met Ile Ser Arg Thr Pro Glu
                405                 410                 415

Val Thr Cys Val Val Val Asp Val Ser His Glu Asp Pro Glu Val Lys
            420                 425                 430

Phe Asn Trp Tyr Val Asp Gly Val Glu Val His Asn Ala Lys Thr Lys
            435                 440                 445

Pro Arg Glu Glu Gln Tyr Asn Ser Thr Tyr Arg Val Val Ser Val Leu
            450                 455                 460

Thr Val Leu His Gln Asp Trp Leu Asn Gly Lys Glu Tyr Lys Cys Lys
465                 470                 475                 480

Val Ser Asn Lys Ala Leu Pro Ala Pro Ile Glu Lys Thr Ile Ser Lys
                485                 490                 495

Ala Lys Gly Gln Pro Arg Glu Pro Gln Val Tyr Thr Leu Pro Pro Ser
            500                 505                 510

Arg Asp Glu Leu Thr Lys Asn Gln Val Ser Leu Thr Cys Leu Val Lys
            515                 520                 525

Gly Phe Tyr Pro Ser Asp Ile Ala Val Glu Trp Glu Ser Asn Gly Gln
            530                 535                 540

Pro Glu Asn Asn Tyr Lys Thr Thr Pro Pro Val Leu Asp Ser Asp Gly
545                 550                 555                 560

Ser Phe Phe Leu Tyr Ser Lys Leu Thr Val Asp Lys Ser Arg Trp Gln
                565                 570                 575

Gln Gly Asn Val Phe Ser Cys Ser Val Met His Glu Ala Leu His Asn
            580                 585                 590

His Tyr Thr Gln Lys Ser Leu Ser Leu Ser Pro Gly Lys
            595                 600                 605

<210> SEQ ID NO 87
<211> LENGTH: 426
<212> TYPE: PRT
<213> ORGANISM: Artificial Sequence
<220> FEATURE:
<223> OTHER INFORMATION: Human TrkC(C32-T429).mmH
      aa 1-398: aa 32 through 429 of NP_001012338.1; aa
      399-426 myc-myc-hexahistidine tag

<400> SEQUENCE: 87
```

```
Cys Pro Ala Asn Cys Val Cys Ser Lys Thr Glu Ile Asn Cys Arg
  1               5                  10                  15

Pro Asp Asp Gly Asn Leu Phe Pro Leu Leu Glu Gly Gln Asp Ser Gly
             20                  25                  30

Asn Ser Asn Gly Asn Ala Ser Ile Asn Ile Thr Asp Ile Ser Arg Asn
         35                  40                  45

Ile Thr Ser Ile His Ile Glu Asn Trp Arg Ser Leu His Thr Leu Asn
 50                  55                  60

Ala Val Asp Met Glu Leu Tyr Thr Gly Leu Gln Lys Leu Thr Ile Lys
 65                  70                  75                  80

Asn Ser Gly Leu Arg Ser Ile Gln Pro Arg Ala Phe Ala Lys Asn Pro
             85                  90                  95

His Leu Arg Tyr Ile Asn Leu Ser Ser Asn Arg Leu Thr Thr Leu Ser
            100                 105                 110

Trp Gln Leu Phe Gln Thr Leu Ser Leu Arg Glu Leu Gln Leu Glu Gln
            115                 120                 125

Asn Phe Phe Asn Cys Ser Cys Asp Ile Arg Trp Met Gln Leu Trp Gln
130                 135                 140

Glu Gln Gly Glu Ala Lys Leu Asn Ser Gln Asn Leu Tyr Cys Ile Asn
145                 150                 155                 160

Ala Asp Gly Ser Gln Leu Pro Leu Phe Arg Met Asn Ile Ser Gln Cys
                165                 170                 175

Asp Leu Pro Glu Ile Ser Val Ser His Val Asn Leu Thr Val Arg Glu
            180                 185                 190

Gly Asp Asn Ala Val Ile Thr Cys Asn Gly Ser Gly Ser Pro Leu Pro
            195                 200                 205

Asp Val Asp Trp Ile Val Thr Gly Leu Gln Ser Ile Asn Thr His Gln
210                 215                 220

Thr Asn Leu Asn Trp Thr Asn Val His Ala Ile Asn Leu Thr Leu Val
225                 230                 235                 240

Asn Val Thr Ser Glu Asp Asn Gly Phe Thr Leu Thr Cys Ile Ala Glu
                245                 250                 255

Asn Val Val Gly Met Ser Asn Ala Ser Val Ala Leu Thr Val Tyr Tyr
            260                 265                 270

Pro Pro Arg Val Val Ser Leu Glu Glu Pro Glu Leu Arg Leu Glu His
            275                 280                 285

Cys Ile Glu Phe Val Val Arg Gly Asn Pro Pro Thr Leu His Trp
290                 295                 300

Leu His Asn Gly Gln Pro Leu Arg Glu Ser Lys Ile Ile His Val Glu
305                 310                 315                 320

Tyr Tyr Gln Glu Gly Glu Ile Ser Glu Gly Cys Leu Leu Phe Asn Lys
                325                 330                 335

Pro Thr His Tyr Asn Asn Gly Asn Tyr Thr Leu Ile Ala Lys Asn Pro
            340                 345                 350

Leu Gly Thr Ala Asn Gln Thr Ile Asn Gly His Phe Leu Lys Glu Pro
            355                 360                 365

Phe Pro Glu Ser Thr Asp Asn Phe Ile Leu Phe Asp Glu Val Ser Pro
370                 375                 380

Thr Pro Pro Ile Thr Val Thr His Lys Pro Glu Glu Asp Thr Glu Gln
385                 390                 395                 400

Lys Leu Ile Ser Glu Glu Asp Leu Gly Gly Glu Gln Lys Leu Ile Ser
                405                 410                 415

Glu Glu Asp Leu His His His His His
```

<210> SEQ ID NO 88
<211> LENGTH: 426
<212> TYPE: PRT
<213> ORGANISM: Artificial Sequence
<220> FEATURE:
<223> OTHER INFORMATION: Mouse TrkC(C32-T429).mmH
aa 1-398: aa 32 through 429 of NP_032772.3; aa
399-426 myc-myc-hexahistidine tag

<400> SEQUENCE: 88

Cys Pro Ala Asn Cys Val Cys Ser Lys Thr Glu Ile Asn Cys Arg Arg
1               5                   10                  15

Pro Asp Asp Gly Asn Leu Phe Pro Leu Leu Glu Gly Gln Asp Ser Gly
            20                  25                  30

Asn Ser Asn Gly Asn Ala Ser Ile Asn Ile Thr Asp Ile Ser Arg Asn
        35                  40                  45

Ile Thr Ser Ile His Ile Glu Asn Trp Arg Gly Leu His Thr Leu Asn
    50                  55                  60

Ala Val Asp Met Glu Leu Tyr Thr Gly Leu Gln Lys Leu Thr Ile Lys
65                  70                  75                  80

Asn Ser Gly Leu Arg Asn Ile Gln Pro Arg Ala Phe Ala Lys Asn Pro
                85                  90                  95

His Leu Arg Tyr Ile Asn Leu Ser Ser Asn Arg Leu Thr Thr Leu Ser
            100                 105                 110

Trp Gln Leu Phe Gln Thr Leu Ser Leu Arg Glu Leu Arg Leu Glu Gln
        115                 120                 125

Asn Phe Phe Asn Cys Ser Cys Asp Ile Arg Trp Met Gln Leu Trp Gln
    130                 135                 140

Glu Gln Gly Glu Ala Arg Leu Asp Ser Gln Ser Leu Tyr Cys Ile Ser
145                 150                 155                 160

Ala Asp Gly Ser Gln Leu Pro Leu Phe Arg Met Asn Ile Ser Gln Cys
                165                 170                 175

Asp Leu Pro Glu Ile Ser Val Ser His Val Asn Leu Thr Val Arg Glu
            180                 185                 190

Gly Asp Asn Ala Val Ile Thr Cys Asn Gly Ser Gly Ser Pro Leu Pro
        195                 200                 205

Asp Val Asp Trp Ile Val Thr Gly Leu Gln Ser Ile Asn Thr His Gln
    210                 215                 220

Thr Asn Leu Asn Trp Thr Asn Val His Ala Ile Asn Leu Thr Leu Val
225                 230                 235                 240

Asn Val Thr Ser Glu Asp Asn Gly Phe Thr Leu Thr Cys Ile Ala Glu
                245                 250                 255

Asn Val Val Gly Met Ser Asn Ala Ser Val Ala Leu Thr Val Tyr Tyr
            260                 265                 270

Pro Pro Arg Val Val Ser Leu Val Glu Pro Glu Val Arg Leu Glu His
        275                 280                 285

Cys Ile Glu Phe Val Val Arg Gly Asn Pro Thr Pro Thr Leu His Trp
    290                 295                 300

Leu Tyr Asn Gly Gln Pro Leu Arg Glu Ser Lys Ile Ile His Met Asp
305                 310                 315                 320

Tyr Tyr Gln Glu Gly Glu Val Ser Glu Gly Cys Leu Leu Phe Asn Lys
                325                 330                 335

Pro Thr His Tyr Asn Asn Gly Asn Tyr Thr Leu Ile Ala Lys Asn Ala
            340                 345                 350

-continued

```
Leu Gly Thr Ala Asn Gln Thr Ile Asn Gly His Phe Leu Lys Glu Pro
            355                 360                 365

Phe Pro Glu Ser Thr Asp Phe Phe Asp Phe Glu Ser Asp Ala Ser Pro
    370                 375                 380

Thr Pro Pro Ile Thr Val Thr His Lys Pro Glu Glu Asp Thr Glu Gln
385                 390                 395                 400

Lys Leu Ile Ser Glu Glu Asp Leu Gly Gly Glu Gln Lys Leu Ile Ser
                405                 410                 415

Glu Glu Asp Leu His His His His His His
            420                 425

<210> SEQ ID NO 89
<211> LENGTH: 426
<212> TYPE: PRT
<213> ORGANISM: Artificial Sequence
<220> FEATURE:
<223> OTHER INFORMATION: MF TrkC(C32-T429).mmH
      aa 1-398: aa 32 through 429 of XP_015308837.1; aa
      399-426 myc-myc-hexahistidine tag

<400> SEQUENCE: 89

Cys Pro Ala Asn Cys Val Cys Ser Lys Thr Glu Ile Asn Cys Arg Arg
1               5                   10                  15

Pro Asp Asp Gly Asn Leu Phe Pro Leu Leu Glu Gly Gln Asp Ser Gly
            20                  25                  30

Asn Ser Asn Gly Asn Ala Ser Ile Asn Ile Thr Asp Ile Ser Arg Asn
        35                  40                  45

Ile Thr Ser Ile His Ile Glu Asn Trp Arg Ser Leu His Thr Leu Asn
50                  55                  60

Ala Val Asp Met Glu Leu Tyr Thr Gly Leu Gln Asn Leu Thr Ile Arg
65                  70                  75                  80

Asn Ser Gly Leu Arg Ser Ile Gln Pro Arg Ala Phe Ala Lys Asn Pro
                85                  90                  95

His Leu Arg Tyr Ile Asn Leu Ser Ser Asn Arg Leu Thr Thr Leu Ser
            100                 105                 110

Trp Gln Leu Phe Gln Thr Leu Ser Leu Arg Glu Leu Arg Leu Glu Gln
        115                 120                 125

Asn Phe Phe Asn Cys Ser Cys Asp Ile Arg Trp Met Gln Leu Trp Gln
130                 135                 140

Glu Gln Gly Glu Ala Lys Leu Asn Asn Gln Asn Leu Tyr Cys Ile Asn
145                 150                 155                 160

Ala Asp Gly Ser Gln Leu Pro Leu Phe Arg Met Asn Ile Ser Gln Cys
                165                 170                 175

Asp Leu Pro Glu Ile Ser Val Ser His Val Asn Leu Thr Val Arg Glu
            180                 185                 190

Gly Asp Asn Ala Val Ile Thr Cys Asn Gly Ser Gly Ser Pro Leu Pro
        195                 200                 205

Asp Val Asp Trp Ile Val Thr Gly Leu Gln Ser Ile Asn Thr His Gln
210                 215                 220

Thr Asn Leu Asn Trp Thr Asn Val His Ala Ile Asn Leu Thr Leu Val
225                 230                 235                 240

Asn Val Thr Ser Glu Asp Asn Gly Phe Thr Leu Thr Cys Ile Ala Glu
                245                 250                 255

Asn Val Val Gly Met Ser Asn Ala Ser Val Ala Leu Thr Val Tyr Tyr
            260                 265                 270
```

```
Pro Pro Arg Val Val Ser Leu Glu Glu Pro Glu Leu Arg Leu Glu His
            275                 280                 285

Cys Ile Glu Phe Val Val Arg Gly Asn Pro Pro Thr Leu His Trp
        290                 295                 300

Leu His Asn Gly Gln Pro Leu Arg Glu Ser Lys Ile Ile His Val Glu
305                 310                 315                 320

Tyr Tyr Gln Glu Gly Glu Ile Ser Gly Cys Leu Leu Phe Asn Lys
            325                 330                 335

Pro Thr His Tyr Asn Asn Gly Asn Tyr Thr Leu Ile Ala Lys Asn Pro
            340                 345                 350

Leu Gly Thr Ala Asn Gln Thr Ile Asn Gly His Phe Leu Lys Glu Pro
            355                 360                 365

Phe Pro Glu Ser Thr Asp Asn Phe Ile Leu Phe Asp Glu Val Ser Pro
            370                 375                 380

Thr Pro Pro Ile Thr Val Thr His Lys Pro Glu Glu Asp Thr Glu Gln
385                 390                 395                 400

Lys Leu Ile Ser Glu Glu Asp Leu Gly Gly Gln Lys Leu Ile Ser
            405                 410                 415

Glu Glu Asp Leu His His His His His His
            420                 425

<210> SEQ ID NO 90
<211> LENGTH: 120
<212> TYPE: PRT
<213> ORGANISM: Artificial Sequence
<220> FEATURE:
<223> OTHER INFORMATION: BDNF_isoform A
      aa 1-120: aa 129 through 247 of NP_733928.1 with a
      Met added on the N-term

<400> SEQUENCE: 90

Met His Ser Asp Pro Ala Arg Arg Gly Glu Leu Ser Val Cys Asp Ser
1               5                   10                  15

Ile Ser Glu Trp Val Thr Ala Ala Asp Lys Lys Thr Ala Val Asp Met
            20                  25                  30

Ser Gly Gly Thr Val Thr Val Leu Glu Lys Val Pro Val Ser Lys Gly
            35                  40                  45

Gln Leu Lys Gln Tyr Phe Tyr Glu Thr Lys Cys Asn Pro Met Gly Tyr
        50                  55                  60

Thr Lys Glu Gly Cys Arg Gly Ile Asp Lys Arg His Trp Asn Ser Gln
65                  70                  75                  80

Cys Arg Thr Thr Gln Ser Tyr Val Arg Ala Leu Thr Met Asp Ser Lys
                85                  90                  95

Lys Arg Ile Gly Trp Arg Phe Ile Arg Ile Asp Thr Ser Cys Val Cys
            100                 105                 110

Thr Leu Thr Ile Lys Arg Gly Arg
        115                 120

<210> SEQ ID NO 91
<211> LENGTH: 791
<212> TYPE: PRT
<213> ORGANISM: Artificial Sequence
<220> FEATURE:
<223> OTHER INFORMATION: TrkB (pRG984.hTrkB ecto-hTrkB TM/Cyto)
      aa 1-792: aa 32 through 822 of NP_001018074.1 or
      Uniprot number Q16620-1 TM/Cyto 399-790

<400> SEQUENCE: 91

Cys Pro Thr Ser Cys Lys Cys Ser Ala Ser Arg Ile Trp Cys Ser Asp
```

-continued

```
1               5                   10                  15
Pro Ser Pro Gly Ile Val Ala Phe Pro Arg Leu Glu Pro Asn Ser Val
            20                  25                  30

Asp Pro Glu Asn Ile Thr Glu Ile Phe Ile Ala Asn Gln Lys Arg Leu
            35                  40                  45

Glu Ile Ile Asn Glu Asp Asp Val Glu Ala Tyr Val Gly Leu Arg Asn
            50                  55                  60

Leu Thr Ile Val Asp Ser Gly Leu Lys Phe Val Ala His Lys Ala Phe
65                  70                  75                  80

Leu Lys Asn Ser Asn Leu Gln His Ile Asn Phe Thr Arg Asn Lys Leu
                85                  90                  95

Thr Ser Leu Ser Arg Lys His Phe Arg His Leu Asp Leu Ser Glu Leu
                100                 105                 110

Ile Leu Val Gly Asn Pro Phe Thr Cys Ser Cys Asp Ile Met Trp Ile
                115                 120                 125

Lys Thr Leu Gln Glu Ala Lys Ser Ser Pro Asp Thr Gln Asp Leu Tyr
            130                 135                 140

Cys Leu Asn Glu Ser Ser Lys Asn Ile Pro Leu Ala Asn Leu Gln Ile
145                 150                 155                 160

Pro Asn Cys Gly Leu Pro Ser Ala Asn Leu Ala Ala Pro Asn Leu Thr
                165                 170                 175

Val Glu Glu Gly Lys Ser Ile Thr Leu Ser Cys Ser Val Ala Gly Asp
                180                 185                 190

Pro Val Pro Asn Met Tyr Trp Asp Val Gly Asn Leu Val Ser Lys His
                195                 200                 205

Met Asn Glu Thr Ser His Thr Gln Gly Ser Leu Arg Ile Thr Asn Ile
            210                 215                 220

Ser Ser Asp Asp Ser Gly Lys Gln Ile Ser Cys Val Ala Glu Asn Leu
225                 230                 235                 240

Val Gly Glu Asp Gln Asp Ser Val Asn Leu Thr Val His Phe Ala Pro
                245                 250                 255

Thr Ile Thr Phe Leu Glu Ser Pro Thr Ser Asp His His Trp Cys Ile
                260                 265                 270

Pro Phe Thr Val Lys Gly Asn Pro Lys Pro Ala Leu Gln Trp Phe Tyr
            275                 280                 285

Asn Gly Ala Ile Leu Asn Glu Ser Lys Tyr Ile Cys Thr Lys Ile His
            290                 295                 300

Val Thr Asn His Thr Glu Tyr His Gly Cys Leu Gln Leu Asp Asn Pro
305                 310                 315                 320

Thr His Met Asn Asn Gly Asp Tyr Thr Leu Ile Ala Lys Asn Glu Tyr
                325                 330                 335

Gly Lys Asp Glu Lys Gln Ile Ser Ala His Phe Met Gly Trp Pro Gly
            340                 345                 350

Ile Asp Asp Gly Ala Asn Pro Asn Tyr Pro Asp Val Ile Tyr Glu Asp
            355                 360                 365

Tyr Gly Thr Ala Ala Asn Asp Ile Gly Asp Thr Thr Asn Arg Ser Asn
            370                 375                 380

Glu Ile Pro Ser Thr Asp Val Thr Asp Lys Thr Gly Arg Glu His Leu
385                 390                 395                 400

Ser Val Tyr Ala Val Val Ile Ala Ser Val Val Gly Phe Cys Leu
                405                 410                 415

Leu Val Met Leu Phe Leu Leu Lys Leu Ala Arg His Ser Lys Phe Gly
            420                 425                 430
```

```
Met Lys Gly Pro Ala Ser Val Ile Ser Asn Asp Asp Ser Ala Ser
        435                 440                 445

Pro Leu His His Ile Ser Asn Gly Ser Asn Thr Pro Ser Ser Ser Glu
        450                 455                 460

Gly Gly Pro Asp Ala Val Ile Ile Gly Met Thr Lys Ile Pro Val Ile
465                 470                 475                 480

Glu Asn Pro Gln Tyr Phe Gly Ile Thr Asn Ser Gln Leu Lys Pro Asp
                485                 490                 495

Thr Phe Val Gln His Ile Lys Arg His Asn Ile Val Leu Lys Arg Glu
            500                 505                 510

Leu Gly Glu Gly Ala Phe Gly Lys Val Phe Leu Ala Glu Cys Tyr Asn
        515                 520                 525

Leu Cys Pro Glu Gln Asp Lys Ile Leu Val Ala Val Lys Thr Leu Lys
        530                 535                 540

Asp Ala Ser Asp Asn Ala Arg Lys Asp Phe His Arg Glu Ala Glu Leu
545                 550                 555                 560

Leu Thr Asn Leu Gln His Glu His Ile Val Lys Phe Tyr Gly Val Cys
                565                 570                 575

Val Glu Gly Asp Pro Leu Ile Met Val Phe Glu Tyr Met Lys His Gly
            580                 585                 590

Asp Leu Asn Lys Phe Leu Arg Ala His Gly Pro Asp Ala Val Leu Met
        595                 600                 605

Ala Glu Gly Asn Pro Pro Thr Glu Leu Thr Gln Ser Gln Met Leu His
        610                 615                 620

Ile Ala Gln Gln Ile Ala Ala Gly Met Val Tyr Leu Ala Ser Gln His
625                 630                 635                 640

Phe Val His Arg Asp Leu Ala Thr Arg Asn Cys Leu Val Gly Glu Asn
                645                 650                 655

Leu Leu Val Lys Ile Gly Asp Phe Gly Met Ser Arg Asp Val Tyr Ser
            660                 665                 670

Thr Asp Tyr Tyr Arg Val Gly Gly His Thr Met Leu Pro Ile Arg Trp
        675                 680                 685

Met Pro Pro Glu Ser Ile Met Tyr Arg Lys Phe Thr Thr Glu Ser Asp
        690                 695                 700

Val Trp Ser Leu Gly Val Val Leu Trp Glu Ile Phe Thr Tyr Gly Lys
705                 710                 715                 720

Gln Pro Trp Tyr Gln Leu Ser Asn Asn Glu Val Ile Glu Cys Ile Thr
                725                 730                 735

Gln Gly Arg Val Leu Gln Arg Pro Arg Thr Cys Pro Gln Glu Val Tyr
            740                 745                 750

Glu Leu Met Leu Gly Cys Trp Gln Arg Glu Pro His Met Arg Lys Asn
        755                 760                 765

Ile Lys Gly Ile His Thr Leu Leu Gln Asn Leu Ala Lys Ala Ser Pro
        770                 775                 780

Val Tyr Leu Asp Ile Leu Gly
785                 790

<210> SEQ ID NO 92
<211> LENGTH: 445
<212> TYPE: PRT
<213> ORGANISM: Artificial Sequence
<220> FEATURE:
<223> OTHER INFORMATION: Mouse TrkB
      aa 1-446: aa 32 through 476 of NP_032771.1
```

<400> SEQUENCE: 92

```
Cys Pro Thr Ser Cys Lys Cys Ser Ser Ala Arg Ile Trp Cys Thr Glu
1               5                   10                  15

Pro Ser Pro Gly Ile Val Ala Phe Pro Arg Leu Glu Pro Asn Ser Val
            20                  25                  30

Asp Pro Glu Asn Ile Thr Glu Ile Leu Ile Ala Asn Gln Lys Arg Leu
        35                  40                  45

Glu Ile Ile Asn Glu Asp Val Glu Ala Tyr Val Gly Leu Arg Asn
    50                  55                  60

Leu Thr Ile Val Asp Ser Gly Leu Lys Phe Val Ala Tyr Lys Ala Phe
65                  70                  75                  80

Leu Lys Asn Ser Asn Leu Arg His Ile Asn Phe Thr Arg Asn Lys Leu
                85                  90                  95

Thr Ser Leu Ser Arg Arg His Phe Arg His Leu Asp Leu Ser Asp Leu
            100                 105                 110

Ile Leu Thr Gly Asn Pro Phe Thr Cys Ser Cys Asp Ile Met Trp Leu
            115                 120                 125

Lys Thr Leu Gln Glu Thr Lys Ser Ser Pro Asp Thr Gln Asp Leu Tyr
    130                 135                 140

Cys Leu Asn Glu Ser Ser Lys Asn Met Pro Leu Ala Asn Leu Gln Ile
145                 150                 155                 160

Pro Asn Cys Gly Leu Pro Ser Ala Arg Leu Ala Ala Pro Asn Leu Thr
                165                 170                 175

Val Glu Glu Gly Lys Ser Val Thr Leu Ser Cys Ser Val Gly Gly Asp
            180                 185                 190

Pro Leu Pro Thr Leu Tyr Trp Asp Val Gly Asn Leu Val Ser Lys His
        195                 200                 205

Met Asn Glu Thr Ser His Thr Gln Gly Ser Leu Arg Ile Thr Asn Ile
    210                 215                 220

Ser Ser Asp Asp Ser Gly Lys Gln Ile Ser Cys Val Ala Glu Asn Leu
225                 230                 235                 240

Val Gly Glu Asp Gln Asp Ser Val Asn Leu Thr Val His Phe Ala Pro
                245                 250                 255

Thr Ile Thr Phe Leu Glu Ser Pro Thr Ser Asp His His Trp Cys Ile
            260                 265                 270

Pro Phe Thr Val Arg Gly Asn Pro Lys Pro Ala Leu Gln Trp Phe Tyr
        275                 280                 285

Asn Gly Ala Ile Leu Asn Glu Ser Lys Tyr Ile Cys Thr Lys Ile His
    290                 295                 300

Val Thr Asn His Thr Glu Tyr His Gly Cys Leu Gln Leu Asp Asn Pro
305                 310                 315                 320

Thr His Met Asn Asn Gly Asp Tyr Thr Leu Met Ala Lys Asn Glu Tyr
                325                 330                 335

Gly Lys Asp Glu Arg Gln Ile Ser Ala His Phe Met Gly Arg Pro Gly
            340                 345                 350

Val Asp Tyr Glu Thr Asn Pro Asn Tyr Pro Glu Val Leu Tyr Glu Asp
        355                 360                 365

Trp Thr Thr Pro Thr Asp Ile Gly Asp Thr Thr Asn Lys Ser Asn Glu
    370                 375                 380

Ile Pro Ser Thr Asp Val Ala Asp Gln Ser Asn Arg Glu His Leu Ser
385                 390                 395                 400

Val Tyr Ala Val Val Ile Ala Ser Val Val Gly Phe Cys Leu Leu
                405                 410                 415
```

```
Val Met Leu Leu Leu Lys Leu Ala Arg His Ser Lys Phe Gly Met
            420                 425                 430

Lys Gly Phe Val Leu Phe His Lys Ile Pro Leu Asp Gly
            435                 440                 445

<210> SEQ ID NO 93
<211> LENGTH: 790
<212> TYPE: PRT
<213> ORGANISM: Artificial Sequence
<220> FEATURE:
<223> OTHER INFORMATION: Chimera TrkB (pRG984.mTrkB ecto-hTrkB TM/Cyto)
      aa 1-398: aa 32 through 429 of NP_001020245.1 or
      Uniprot number P15209-1; Human TrkB TM/Cyto
      399-790 (aaa 431 through 822 of NP_001018074.1)

<400> SEQUENCE: 93

Cys Pro Thr Ser Cys Lys Cys Ser Ser Ala Arg Ile Trp Cys Thr Glu
1               5                   10                  15

Pro Ser Pro Gly Ile Val Ala Phe Pro Arg Leu Glu Pro Asn Ser Val
            20                  25                  30

Asp Pro Glu Asn Ile Thr Glu Ile Leu Ile Ala Asn Gln Lys Arg Leu
        35                  40                  45

Glu Ile Ile Asn Glu Asp Asp Val Glu Ala Tyr Val Gly Leu Arg Asn
    50                  55                  60

Leu Thr Ile Val Asp Ser Gly Leu Lys Phe Val Ala Tyr Lys Ala Phe
65                  70                  75                  80

Leu Lys Asn Ser Asn Leu Arg His Ile Asn Phe Thr Arg Asn Lys Leu
                85                  90                  95

Thr Ser Leu Ser Arg Arg His Phe Arg His Leu Asp Leu Ser Asp Leu
            100                 105                 110

Ile Leu Thr Gly Asn Pro Phe Thr Cys Ser Cys Asp Ile Met Trp Leu
        115                 120                 125

Lys Thr Leu Gln Glu Thr Lys Ser Ser Pro Asp Thr Gln Asp Leu Tyr
    130                 135                 140

Cys Leu Asn Glu Ser Ser Lys Asn Met Pro Leu Ala Asn Leu Gln Ile
145                 150                 155                 160

Pro Asn Cys Gly Leu Pro Ser Ala Arg Leu Ala Ala Pro Asn Leu Thr
                165                 170                 175

Val Glu Glu Gly Lys Ser Val Thr Leu Ser Cys Ser Val Gly Gly Asp
            180                 185                 190

Pro Leu Pro Thr Leu Tyr Trp Asp Val Gly Asn Leu Val Ser Lys His
        195                 200                 205

Met Asn Glu Thr Ser His Thr Gln Gly Ser Leu Arg Ile Thr Asn Ile
    210                 215                 220

Ser Ser Asp Asp Ser Gly Lys Gln Ile Ser Cys Val Ala Glu Asn Leu
225                 230                 235                 240

Val Gly Glu Asp Gln Asp Ser Val Asn Leu Thr Val His Phe Ala Pro
                245                 250                 255

Thr Ile Thr Phe Leu Glu Ser Pro Thr Ser Asp His His Trp Cys Ile
            260                 265                 270

Pro Phe Thr Val Arg Gly Asn Pro Lys Pro Ala Leu Gln Trp Phe Tyr
        275                 280                 285

Asn Gly Ala Ile Leu Asn Glu Ser Lys Tyr Ile Cys Thr Lys Ile His
    290                 295                 300

Val Thr Asn His Thr Glu Tyr His Gly Cys Leu Gln Leu Asp Asn Pro
305                 310                 315                 320
```

```
Thr His Met Asn Asn Gly Asp Tyr Thr Leu Met Ala Lys Asn Glu Tyr
                    325                 330                 335

Gly Lys Asp Glu Arg Gln Ile Ser Ala His Phe Met Gly Arg Pro Gly
                340                 345                 350

Val Asp Tyr Glu Thr Asn Pro Asn Tyr Pro Glu Val Leu Tyr Glu Asp
            355                 360                 365

Trp Thr Thr Pro Thr Asp Ile Gly Asp Thr Thr Asn Lys Ser Asn Glu
370                 375                 380

Ile Pro Ser Thr Asp Val Ala Asp Gln Ser Asn Arg Glu His Leu Ser
385                 390                 395                 400

Val Tyr Ala Val Val Ile Ala Ser Val Val Gly Phe Cys Leu Leu
                405                 410                 415

Val Met Leu Phe Leu Leu Lys Leu Ala Arg His Ser Lys Phe Gly Met
                420                 425                 430

Lys Gly Pro Ala Ser Val Ile Ser Asn Asp Asp Ser Ala Ser Pro
                435                 440                 445

Leu His His Ile Ser Asn Gly Ser Asn Thr Pro Ser Ser Glu Gly
                450                 455                 460

Gly Pro Asp Ala Val Ile Ile Gly Met Thr Lys Ile Pro Val Ile Glu
465                 470                 475                 480

Asn Pro Gln Tyr Phe Gly Ile Thr Asn Ser Gln Leu Lys Pro Asp Thr
                485                 490                 495

Phe Val Gln His Ile Lys Arg His Asn Ile Val Leu Lys Arg Glu Leu
                500                 505                 510

Gly Glu Gly Ala Phe Gly Lys Val Phe Leu Ala Glu Cys Tyr Asn Leu
                515                 520                 525

Cys Pro Glu Gln Asp Lys Ile Leu Val Ala Val Lys Thr Leu Lys Asp
                530                 535                 540

Ala Ser Asp Asn Ala Arg Lys Asp Phe His Arg Glu Ala Glu Leu Leu
545                 550                 555                 560

Thr Asn Leu Gln His Glu His Ile Val Lys Phe Tyr Gly Val Cys Val
                565                 570                 575

Glu Gly Asp Pro Leu Ile Met Val Phe Glu Tyr Met Lys His Gly Asp
                580                 585                 590

Leu Asn Lys Phe Leu Arg Ala His Gly Pro Asp Ala Val Leu Met Ala
                595                 600                 605

Glu Gly Asn Pro Pro Thr Glu Leu Thr Gln Ser Gln Met Leu His Ile
610                 615                 620

Ala Gln Gln Ile Ala Ala Gly Met Val Tyr Leu Ala Ser Gln His Phe
625                 630                 635                 640

Val His Arg Asp Leu Ala Thr Arg Asn Cys Leu Val Gly Glu Asn Leu
                645                 650                 655

Leu Val Lys Ile Gly Asp Phe Gly Met Ser Arg Asp Val Tyr Ser Thr
                660                 665                 670

Asp Tyr Tyr Arg Val Gly Gly His Thr Met Leu Pro Ile Arg Trp Met
                675                 680                 685

Pro Pro Glu Ser Ile Met Tyr Arg Lys Phe Thr Thr Glu Ser Asp Val
                690                 695                 700

Trp Ser Leu Gly Val Val Leu Trp Glu Ile Phe Thr Tyr Gly Lys Gln
705                 710                 715                 720

Pro Trp Tyr Gln Leu Ser Asn Asn Glu Val Ile Glu Cys Ile Thr Gln
                725                 730                 735
```

-continued

```
Gly Arg Val Leu Gln Arg Pro Arg Thr Cys Pro Gln Glu Val Tyr Glu
                740                 745                 750

Leu Met Leu Gly Cys Trp Gln Arg Glu Pro His Met Arg Lys Asn Ile
            755                 760                 765

Lys Gly Ile His Thr Leu Leu Gln Asn Leu Ala Lys Ala Ser Pro Val
        770                 775                 780

Tyr Leu Asp Ile Leu Gly
785                 790

<210> SEQ ID NO 94
<211> LENGTH: 791
<212> TYPE: PRT
<213> ORGANISM: Artificial Sequence
<220> FEATURE:
<223> OTHER INFORMATION: AGM TrkB (pRGN984.agmTrkB)
      1-791: aa 32 through 822 of XP_007967815.1

<400> SEQUENCE: 94

Cys Pro Arg Ser Cys Lys Cys Ser Ala Ser Arg Ile Trp Cys Ser Asp
1               5                   10                  15

Pro Ser Pro Gly Ile Val Ala Phe Pro Arg Leu Glu Pro Asn Ser Val
            20                  25                  30

Asp Pro Glu Asn Ile Thr Glu Ile Phe Ile Ala Asn Gln Lys Arg Leu
        35                  40                  45

Glu Ile Ile Asn Glu Asp Val Glu Ala Tyr Val Gly Leu Arg Asn
    50                  55                  60

Leu Thr Ile Val Asp Ser Gly Leu Lys Phe Val Ala His Lys Ala Phe
65                  70                  75                  80

Leu Lys Asn Ser Asn Leu Gln His Ile Asn Phe Thr Arg Asn Lys Leu
                85                  90                  95

Thr Ser Leu Ser Arg Lys His Phe Arg His Leu Asp Leu Ser Glu Leu
            100                 105                 110

Ile Leu Val Gly Asn Pro Phe Thr Cys Ser Cys Asp Ile Met Trp Ile
        115                 120                 125

Lys Thr Leu Gln Glu Ala Lys Ser Ser Pro Asp Thr Gln Asp Leu Tyr
    130                 135                 140

Cys Leu Asn Glu Ser Ser Lys Asn Ile Pro Leu Ala Asn Leu Gln Ile
145                 150                 155                 160

Pro Asn Cys Gly Leu Pro Ser Ala Asn Leu Ala Ala Pro Asn Leu Thr
                165                 170                 175

Val Glu Glu Gly Lys Ser Ile Thr Leu Ser Cys Ser Val Ala Gly Asp
            180                 185                 190

Pro Val Pro Asn Met Tyr Trp Asp Val Gly Asn Leu Val Ser Lys His
        195                 200                 205

Met Asn Glu Thr Ser His Thr Gln Gly Ser Leu Arg Ile Thr Asn Ile
    210                 215                 220

Ser Ser Asp Asp Ser Gly Lys Gln Ile Ser Cys Val Ala Glu Asn Leu
225                 230                 235                 240

Val Gly Glu Asp Gln Asp Ser Val Asn Leu Thr Val His Phe Ala Pro
                245                 250                 255

Thr Ile Thr Phe Leu Glu Ser Pro Thr Ser Asp His His Trp Cys Ile
            260                 265                 270

Pro Phe Thr Val Lys Gly Asn Pro Lys Pro Ala Leu Gln Trp Phe Tyr
        275                 280                 285

Asn Gly Ala Ile Leu Asn Glu Ser Lys Tyr Ile Cys Thr Lys Ile His
    290                 295                 300
```

```
Val Thr Asn His Thr Glu Tyr His Gly Cys Leu Gln Leu Asp Asn Pro
305                 310                 315                 320

Thr His Met Asn Asn Gly Asp Tyr Thr Leu Ile Ala Lys Asn Glu Tyr
            325                 330                 335

Gly Lys Asp Glu Lys Gln Ile Ser Ala His Phe Met Gly Trp Pro Gly
        340                 345                 350

Ile Asp Asp Gly Ala Asn Pro Asn Tyr Pro Asp Val Ile Tyr Glu Asp
    355                 360                 365

Tyr Gly Thr Ala Ala Asn Asp Ile Gly Asp Thr Thr Asn Arg Ser Asn
370                 375                 380

Glu Ile Pro Ser Thr Asp Val Thr Asp Lys Thr Gly Arg Glu His Leu
385                 390                 395                 400

Ser Val Tyr Ala Val Val Ile Ala Ser Val Val Gly Phe Cys Leu
            405                 410                 415

Leu Val Met Leu Phe Leu Leu Lys Leu Ala Arg His Ser Lys Phe Gly
            420                 425                 430

Met Lys Gly Pro Ala Ser Val Ile Ser Asn Asp Asp Ser Ala Ser
        435                 440                 445

Pro Leu His His Ile Ser Asn Gly Ser Asn Thr Pro Ser Ser Ser Glu
    450                 455                 460

Gly Gly Pro Asp Ala Val Ile Ile Gly Met Thr Lys Ile Pro Val Ile
465                 470                 475                 480

Glu Asn Pro Gln Tyr Phe Gly Ile Thr Asn Ser Gln Leu Lys Pro Asp
            485                 490                 495

Thr Phe Val Gln His Ile Lys Arg His Asn Ile Val Leu Lys Arg Glu
            500                 505                 510

Leu Gly Glu Gly Ala Phe Gly Lys Val Phe Leu Ala Glu Cys Tyr Asn
        515                 520                 525

Leu Cys Pro Glu Gln Asp Lys Ile Leu Val Ala Val Lys Thr Leu Lys
    530                 535                 540

Asp Ala Ser Asp Asn Ala Arg Lys Asp Phe His Arg Glu Ala Glu Leu
545                 550                 555                 560

Leu Thr Asn Leu Gln His Glu His Ile Val Lys Phe Tyr Gly Val Cys
            565                 570                 575

Val Glu Gly Asp Pro Leu Ile Met Val Phe Glu Tyr Met Lys His Gly
            580                 585                 590

Asp Leu Asn Lys Phe Leu Arg Ala His Gly Pro Asp Ala Val Leu Met
        595                 600                 605

Ala Glu Gly Asn Pro Pro Thr Glu Leu Thr Gln Ser Gln Met Leu His
        610                 615                 620

Ile Ala Gln Gln Ile Ala Ala Gly Met Val Tyr Leu Ala Ser Gln His
625                 630                 635                 640

Phe Val His Arg Asp Leu Ala Thr Arg Asn Cys Leu Val Gly Glu Asn
            645                 650                 655

Leu Leu Val Lys Ile Gly Asp Phe Gly Met Ser Arg Asp Val Tyr Ser
            660                 665                 670

Thr Asp Tyr Tyr Arg Val Gly Gly His Thr Met Leu Pro Ile Arg Trp
        675                 680                 685

Met Pro Pro Glu Ser Ile Met Tyr Arg Lys Phe Thr Thr Glu Ser Asp
        690                 695                 700

Val Trp Ser Leu Gly Val Val Leu Trp Glu Ile Phe Thr Tyr Gly Lys
705                 710                 715                 720
```

```
Gln Pro Trp Tyr Gln Leu Ser Asn Asn Glu Val Ile Glu Cys Ile Thr
                725                 730                 735

Gln Gly Arg Val Leu Gln Arg Pro Arg Thr Cys Pro Gln Glu Val Tyr
            740                 745                 750

Glu Leu Met Leu Gly Cys Trp Gln Arg Glu Pro His Met Arg Lys Asn
        755                 760                 765

Ile Lys Gly Ile His Thr Leu Leu Gln Asn Leu Ala Lys Ala Ser Pro
    770                 775                 780

Val Tyr Leu Asp Ile Leu Gly
785                 790

<210> SEQ ID NO 95
<211> LENGTH: 807
<212> TYPE: PRT
<213> ORGANISM: Artificial Sequence
<220> FEATURE:
<223> OTHER INFORMATION: MM TrkB (mmTrkB)
      1-807: aa 32 through 838 of NP_001248226.1

<400> SEQUENCE: 95

Cys Pro Thr Ser Cys Lys Cys Ser Ala Ser Arg Ile Trp Cys Ser Asp
1               5                   10                  15

Pro Ser Pro Gly Ile Val Ala Phe Pro Arg Leu Glu Pro Asn Ser Val
            20                  25                  30

Asp Pro Glu Asn Ile Thr Glu Ile Phe Ile Ala Asn Gln Lys Arg Leu
        35                  40                  45

Glu Ile Ile Asn Glu Asp Asp Val Glu Ala Tyr Val Gly Leu Arg Asn
    50                  55                  60

Leu Thr Ile Val Asp Ser Gly Leu Lys Phe Val Ala His Lys Ala Phe
65                  70                  75                  80

Leu Lys Asn Ser Asn Leu Gln His Ile Asn Phe Thr Arg Asn Lys Leu
                85                  90                  95

Thr Ser Leu Ser Arg Lys His Phe Arg His Leu Asp Leu Ser Glu Leu
            100                 105                 110

Ile Leu Val Gly Asn Pro Phe Thr Cys Ser Cys Asp Ile Met Trp Ile
        115                 120                 125

Lys Thr Leu Gln Glu Ala Lys Ser Ser Pro Asp Thr Gln Asp Leu Tyr
    130                 135                 140

Cys Leu Asn Glu Ser Ser Lys Asn Ile Pro Leu Ala Asn Leu Gln Ile
145                 150                 155                 160

Pro Asn Cys Gly Leu Pro Ser Ala Asn Leu Ala Ala Pro Asn Leu Thr
                165                 170                 175

Val Glu Glu Gly Lys Ser Ile Thr Leu Ser Cys Ser Val Ala Gly Asp
            180                 185                 190

Pro Val Pro Asn Met Tyr Trp Asp Val Gly Asn Leu Val Ser Lys His
        195                 200                 205

Met Asn Glu Thr Ser His Thr Gln Gly Ser Leu Arg Ile Thr Asn Ile
    210                 215                 220

Ser Ser Asp Asp Ser Gly Lys Gln Ile Ser Cys Val Ala Glu Asn Leu
225                 230                 235                 240

Val Gly Glu Asp Gln Asp Ser Val Asn Leu Thr Val His Phe Ala Pro
                245                 250                 255

Thr Ile Thr Phe Leu Glu Ser Pro Thr Ser Asp His His Trp Cys Ile
            260                 265                 270

Pro Phe Thr Val Lys Gly Asn Pro Lys Pro Ala Leu Gln Trp Phe Tyr
        275                 280                 285
```

```
Asn Gly Ala Ile Leu Asn Glu Ser Lys Tyr Ile Cys Thr Lys Ile His
    290                 295                 300

Val Thr Asn His Thr Glu Tyr His Gly Cys Leu Gln Leu Asp Asn Pro
305                 310                 315                 320

Thr His Met Asn Asn Gly Asp Tyr Thr Leu Ile Ala Lys Asn Glu Tyr
                325                 330                 335

Gly Lys Asp Glu Lys Gln Ile Ser Ala His Phe Met Gly Trp Pro Gly
                340                 345                 350

Ile Asp Asp Gly Ala Asn Pro Asn Tyr Pro Asp Val Ile Tyr Glu Asp
                355                 360                 365

Tyr Gly Thr Ala Ala Asn Asp Ile Gly Asp Thr Thr Asn Arg Ser Asn
    370                 375                 380

Glu Ile Pro Ser Thr Asp Val Thr Asp Lys Thr Gly Arg Glu His Leu
385                 390                 395                 400

Ser Val Tyr Ala Val Val Ile Ala Ser Val Val Gly Phe Cys Leu
                405                 410                 415

Leu Val Met Leu Phe Leu Leu Lys Leu Ala Arg His Ser Lys Phe Gly
                420                 425                 430

Met Lys Asp Phe Ser Trp Phe Gly Phe Gly Lys Val Lys Ser Arg Gln
                435                 440                 445

Gly Val Gly Pro Ala Ser Val Ile Ser Asn Asp Asp Asp Ser Ala Ser
    450                 455                 460

Pro Leu His His Ile Ser Asn Gly Ser Asn Thr Pro Ser Ser Ser Glu
465                 470                 475                 480

Gly Gly Pro Asp Ala Val Ile Ile Gly Met Thr Lys Ile Pro Val Ile
                485                 490                 495

Glu Asn Pro Gln Tyr Phe Gly Ile Thr Asn Ser Gln Leu Lys Pro Asp
                500                 505                 510

Thr Phe Val Gln His Ile Lys Arg His Asn Ile Val Leu Lys Arg Glu
                515                 520                 525

Leu Gly Glu Gly Ala Phe Gly Lys Val Phe Leu Ala Glu Cys Tyr Asn
    530                 535                 540

Leu Cys Pro Glu Gln Asp Lys Ile Leu Val Ala Val Lys Thr Leu Lys
545                 550                 555                 560

Asp Ala Ser Asp Asn Ala Arg Lys Asp Phe His Arg Glu Ala Glu Leu
                565                 570                 575

Leu Thr Asn Leu Gln His Glu His Ile Val Lys Phe Tyr Gly Val Cys
                580                 585                 590

Val Glu Gly Asp Pro Leu Ile Met Val Phe Glu Tyr Met Lys His Gly
    595                 600                 605

Asp Leu Asn Lys Phe Leu Arg Ala His Gly Pro Asp Ala Val Leu Met
610                 615                 620

Ala Glu Gly Asn Pro Pro Thr Glu Leu Thr Gln Ser Gln Met Leu His
625                 630                 635                 640

Ile Ala Gln Gln Ile Ala Ala Gly Met Val Tyr Leu Ala Ser Gln His
                645                 650                 655

Phe Val His Arg Asp Leu Ala Thr Arg Asn Cys Leu Val Gly Glu Asn
                660                 665                 670

Leu Leu Val Lys Ile Gly Asp Phe Gly Met Ser Arg Asp Val Tyr Ser
                675                 680                 685

Thr Asp Tyr Tyr Arg Val Gly Gly His Thr Met Leu Pro Ile Arg Trp
    690                 695                 700
```

```
Met Pro Pro Glu Ser Ile Met Tyr Arg Lys Phe Thr Thr Glu Ser Asp
705                 710                 715                 720

Val Trp Ser Leu Gly Val Val Leu Trp Glu Ile Phe Thr Tyr Gly Lys
            725                 730                 735

Gln Pro Trp Tyr Gln Leu Ser Asn Asn Glu Val Ile Glu Cys Ile Thr
            740                 745                 750

Gln Gly Arg Val Leu Gln Arg Pro Arg Thr Cys Pro Gln Glu Val Tyr
            755                 760                 765

Glu Leu Met Leu Gly Cys Trp Gln Arg Glu Pro His Met Arg Lys Asn
            770                 775                 780

Ile Lys Gly Ile His Thr Leu Leu Gln Asn Leu Ala Lys Ala Ser Pro
785                 790                 795                 800

Val Tyr Leu Asp Ile Leu Gly
            805

<210> SEQ ID NO 96
<211> LENGTH: 807
<212> TYPE: PRT
<213> ORGANISM: Artificial Sequence
<220> FEATURE:
<223> OTHER INFORMATION: MF TrkB (mfTrkB)
      1-807 : aa 32 through 838 of XP_005582102.1

<400> SEQUENCE: 96

Cys Pro Thr Ser Cys Lys Cys Ser Ala Ser Arg Ile Trp Cys Ser Asp
1               5                   10                  15

Pro Ser Pro Gly Ile Val Ala Phe Pro Arg Leu Glu Pro Asn Ser Val
            20                  25                  30

Asp Pro Glu Asn Ile Thr Glu Ile Phe Ile Ala Asn Gln Lys Arg Leu
            35                  40                  45

Glu Ile Ile Asn Glu Asp Asp Val Glu Ala Tyr Val Gly Leu Arg Asn
    50                  55                  60

Leu Thr Ile Val Asp Ser Gly Leu Lys Phe Val Ala His Lys Ala Phe
65                  70                  75                  80

Leu Lys Asn Ser Asn Leu Gln His Ile Asn Phe Thr Arg Asn Lys Leu
                85                  90                  95

Thr Ser Leu Ser Arg Lys His Phe Arg His Leu Asp Leu Ser Glu Leu
            100                 105                 110

Ile Leu Val Gly Asn Pro Phe Thr Cys Ser Cys Asp Ile Met Trp Ile
            115                 120                 125

Lys Thr Leu Gln Glu Ala Lys Ser Ser Pro Asp Thr Gln Asp Leu Tyr
130                 135                 140

Cys Leu Asn Glu Ser Ser Lys Asn Ile Pro Leu Ala Asn Leu Gln Ile
145                 150                 155                 160

Pro Asn Cys Gly Leu Pro Ser Ala Asn Leu Ala Ala Pro Asn Leu Thr
                165                 170                 175

Val Glu Glu Gly Lys Ser Ile Thr Leu Ser Cys Ser Val Ala Gly Asp
            180                 185                 190

Pro Val Pro Asn Met Tyr Trp Asp Val Gly Asn Leu Val Ser Lys His
            195                 200                 205

Met Asn Glu Thr Ser His Thr Gln Gly Ser Leu Arg Ile Thr Asn Ile
    210                 215                 220

Ser Ser Asp Asp Ser Gly Lys Gln Ile Ser Cys Val Ala Glu Asn Leu
225                 230                 235                 240

Val Gly Glu Asp Gln Asp Ser Val Asn Leu Thr Val His Phe Ala Pro
                245                 250                 255
```

```
Thr Ile Thr Phe Leu Glu Ser Pro Thr Ser Asp His His Trp Cys Ile
            260                 265                 270

Pro Phe Thr Val Lys Gly Asn Pro Lys Pro Ala Leu Gln Trp Phe Tyr
            275                 280                 285

Asn Gly Ala Ile Leu Asn Glu Ser Lys Tyr Ile Cys Thr Lys Ile His
            290                 295                 300

Val Thr Asn His Thr Glu Tyr His Gly Cys Leu Gln Leu Asp Asn Pro
305                 310                 315                 320

Thr His Met Asn Asn Gly Asp Tyr Thr Leu Ile Ala Lys Asn Glu Tyr
                325                 330                 335

Gly Lys Asp Glu Lys Gln Ile Ser Ala His Phe Met Gly Trp Pro Gly
            340                 345                 350

Ile Asp Asp Gly Ala Asn Pro Asn Tyr Pro Asp Val Ile Tyr Glu Asp
            355                 360                 365

Tyr Gly Thr Ala Ala Asn Asp Ile Gly Asp Thr Thr Asn Arg Ser Asn
370                 375                 380

Glu Ile Pro Ser Thr Asp Val Thr Asp Lys Thr Gly Arg Glu His Leu
385                 390                 395                 400

Ser Val Tyr Ala Val Val Ile Ala Ser Val Val Gly Phe Cys Leu
            405                 410                 415

Leu Val Met Leu Phe Leu Leu Lys Leu Ala Arg His Ser Lys Phe Gly
            420                 425                 430

Met Lys Asp Phe Ser Trp Phe Gly Phe Gly Lys Val Lys Ser Arg Gln
            435                 440                 445

Gly Val Gly Pro Ala Ser Val Ile Ser Asn Asp Asp Asp Ser Ala Ser
            450                 455                 460

Pro Leu His His Ile Ser Asn Gly Ser Asn Thr Pro Ser Ser Ser Glu
465                 470                 475                 480

Gly Gly Pro Asp Ala Val Ile Ile Gly Met Thr Lys Ile Pro Val Ile
            485                 490                 495

Glu Asn Pro Gln Tyr Phe Gly Ile Thr Asn Ser Gln Leu Lys Pro Asp
            500                 505                 510

Thr Phe Val Gln His Ile Lys Arg His Asn Ile Val Leu Lys Arg Glu
            515                 520                 525

Leu Gly Glu Gly Ala Phe Gly Lys Val Phe Leu Ala Glu Cys Tyr Asn
            530                 535                 540

Leu Cys Pro Glu Gln Asp Lys Ile Leu Val Ala Val Lys Thr Leu Lys
545                 550                 555                 560

Asp Ala Ser Asp Asn Ala Arg Lys Asp Phe His Arg Glu Ala Glu Leu
                565                 570                 575

Leu Thr Asn Leu Gln His Glu His Ile Val Lys Phe Tyr Gly Val Cys
            580                 585                 590

Val Glu Gly Asp Pro Leu Ile Met Val Phe Glu Tyr Met Lys His Gly
            595                 600                 605

Asp Leu Asn Lys Phe Leu Arg Ala His Gly Pro Asp Ala Val Leu Met
            610                 615                 620

Ala Glu Gly Asn Pro Pro Thr Glu Leu Thr Gln Ser Gln Met Leu His
625                 630                 635                 640

Ile Ala Gln Gln Ile Ala Ala Gly Met Val Tyr Leu Ala Ser Gln His
                645                 650                 655

Phe Val His Arg Asp Leu Ala Thr Arg Asn Cys Leu Val Gly Glu Asn
            660                 665                 670
```

```
Leu Leu Val Lys Ile Gly Asp Phe Gly Met Ser Arg Asp Val Tyr Ser
            675                 680                 685

Thr Asp Tyr Tyr Arg Val Gly Gly His Thr Met Leu Pro Ile Arg Trp
690                 695                 700

Met Pro Pro Glu Ser Ile Met Tyr Arg Lys Phe Thr Thr Glu Ser Asp
705                 710                 715                 720

Val Trp Ser Leu Gly Val Val Leu Trp Glu Ile Phe Thr Tyr Gly Lys
                725                 730                 735

Gln Pro Trp Tyr Gln Leu Ser Asn Asn Glu Val Ile Glu Cys Ile Thr
            740                 745                 750

Gln Gly Arg Val Leu Gln Arg Pro Arg Thr Cys Pro Gln Glu Val Tyr
        755                 760                 765

Glu Leu Met Leu Gly Cys Trp Gln Arg Glu Pro His Met Arg Lys Asn
    770                 775                 780

Ile Lys Gly Ile His Thr Leu Leu Gln Asn Leu Ala Lys Ala Ser Pro
785                 790                 795                 800

Val Tyr Leu Asp Ile Leu Gly
                805

<210> SEQ ID NO 97
<211> LENGTH: 447
<212> TYPE: PRT
<213> ORGANISM: Artificial Sequence
<220> FEATURE:
<223> OTHER INFORMATION: H1M8037C heavy chain

<400> SEQUENCE: 97

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asp Ile Ile Trp Val Arg Gln Ala Pro Gly Gln Gly Leu Glu Trp Met
        35                  40                  45

Gly Tyr Ile Asn Pro Tyr Asn Asp Gly Thr Lys Tyr Asn Glu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Leu Lys Tyr Arg Arg Phe Arg Tyr Tyr Ala Ile Asp Tyr
            100                 105                 110

Trp Gly Gln Gly Thr Thr Val Thr Val Ser Ser Ala Lys Thr Thr Pro
        115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Glu Thr Val Thr Cys Asn Val Ala
        195                 200                 205

His Pro Ala Ser Ser Thr Lys Val Asp Lys Lys Ile Val Pro Arg Asp
    210                 215                 220
```

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
            245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
            275                 280                 285

Thr Gln Pro Arg Glu Glu Gln Phe Asn Ser Thr Phe Arg Ser Val Ser
    290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
            355                 360                 365

Ile Thr Asp Phe Phe Pro Glu Asp Ile Thr Val Glu Trp Gln Trp Asn
370                 375                 380

Gly Gln Pro Ala Glu Asn Tyr Lys Asn Thr Gln Pro Ile Met Asp Thr
385                 390                 395                 400

Asp Gly Ser Tyr Phe Val Tyr Ser Lys Leu Asn Val Gln Lys Ser Asn
                405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
            435                 440                 445

<210> SEQ ID NO 98
<211> LENGTH: 214
<212> TYPE: PRT
<213> ORGANISM: Artificial Sequence
<220> FEATURE:
<223> OTHER INFORMATION: H1M8037C light chain

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Val Tyr Ser Asn
            20                  25                  30

Leu Ala Trp Tyr Gln Gln Lys Pro Gly Lys Ala Pro Lys Leu Leu Ile
            35                  40                  45

Tyr Ala Ala Ser Asn Leu Gln Ser Gly Val Pro Ser Arg Phe Ser Gly
50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln His Phe Trp Gly Ser Pro Phe
                85                  90                  95

Thr Phe Gly Gln Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
            130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Thr Tyr Ser Met Ser
            165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Gly Glu Cys
    210

<210> SEQ ID NO 99
<211> LENGTH: 445
<212> TYPE: PRT
<213> ORGANISM: Artificial Sequence
<220> FEATURE:
<223> OTHER INFORMATION: H4H9780P Full length heavy chain

<400> SEQUENCE: 99

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Phe
            20                  25                  30

Gly Met His Trp Val Arg Gln Ala Pro Gly Lys Gly Leu Glu Trp Val
        35                  40                  45

Ser Val Ile Ser Tyr Asp Gly Ile Asn Thr Tyr Tyr Thr Asp Ser Val
    50                  55                  60

Lys Gly Arg Phe Thr Ile Ser Arg Asp Asn Lys Asn Thr Leu Tyr
65                  70                  75                  80

Leu Gln Met Asn Gly Leu Arg Ala Glu Asp Thr Ala Leu Tyr Tyr Cys
                85                  90                  95

Val Gln Gly Ser Ile Gly Thr Val Phe Glu Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Lys Thr Tyr Thr Cys Asn Val Asp His Lys Pro Ser
    195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
        260                 265                 270

Phe Asn Trp Tyr Val Asp Gly Val Glu Val His Asn Ala Lys Thr Lys
    275                 280                 285

```
Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Gln Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly Lys
                435                 440                 445

<210> SEQ ID NO 100
<211> LENGTH: 214
<212> TYPE: PRT
<213> ORGANISM: Artificial Sequence
<220> FEATURE:
<223> OTHER INFORMATION: H4H9780P Full length light chain

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Gly Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Thr Ser Ala Pro Phe
                85                  90                  95

Thr Phe Gly Pro Gly Thr Lys Val Asp Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205
```

Phe Asn Arg Gly Glu Cys
    210

<210> SEQ ID NO 101
<211> LENGTH: 449
<212> TYPE: PRT
<213> ORGANISM: Artificial Sequence
<220> FEATURE:
<223> OTHER INFORMATION: H4H9814P Full length heavy chain

<400> SEQUENCE: 101

Glu Val Gln Leu Val Glu Ser Gly Gly Gly Leu Val Gln Pro Gly Gly
1               5                   10                  15

Ser Leu Lys Leu Ser Cys Thr Ala Ser Gly Phe Thr Phe Ser Gly Ser
            20                  25                  30

Val Ile His Trp Val Arg Gln Ala Ser Gly Lys Gly Leu Glu Trp Ile
        35                  40                  45

Gly Arg Ile Arg Asn Lys Ala Asn Ser Tyr Ala Thr Ala Tyr Gly Ala
    50                  55                  60

Ser Val Thr Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Phe Pro Gly Val Val Gly Arg Gly Gly Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

```
Leu Pro Pro Ser Gln Glu Met Thr Lys Asn Gln Val Ser Leu Thr
            355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                405                 410                 415
Ser Arg Trp Gln Glu Gly Asn Val Phe Ser Cys Ser Val Met His Glu
                420                 425                 430
Ala Leu His Asn His Tyr Thr Gln Lys Ser Leu Ser Leu Ser Leu Gly
            435                 440                 445
Lys

<210> SEQ ID NO 102
<211> LENGTH: 220
<212> TYPE: PRT
<213> ORGANISM: Artificial Sequence
<220> FEATURE:
<223> OTHER INFORMATION: H4H9814P Full length light chain

<400> SEQUENCE: 102

Asp Ile Val Met Thr Gln Ser Pro Asp Ser Leu Ala Val Ser Leu Gly
1               5                   10                  15
Glu Gly Ala Thr Ile Asn Cys Met Ser Ser Gln Ser Val Leu Phe Ser
                20                  25                  30
Ser Asn Asn Lys Asn Tyr Leu Ala Trp Tyr Gln Gln Lys Pro Gly Gln
            35                  40                  45
Pro Pro Lys Leu Leu Phe Tyr Trp Ala Ser Thr Arg Glu Ser Gly Val
50                  55                  60
Pro Asp Arg Phe Gly Gly Ser Gly Ser Gly Thr Asp Phe Ser Leu Thr
65                  70                  75                  80
Ile Asn Ser Leu Gln Thr Glu Asp Val Ala Val Tyr Tyr Cys Leu Gln
                85                  90                  95
Tyr Tyr Ser Ile Pro Trp Thr Phe Gly Gln Gly Thr Lys Val Glu Ile
                100                 105                 110
Lys Arg Thr Val Ala Ala Pro Ser Val Phe Ile Phe Pro Pro Ser Asp
            115                 120                 125
Glu Gln Leu Lys Ser Gly Thr Ala Ser Val Val Cys Leu Leu Asn Asn
        130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
            180                 185                 190
Glu Lys His Lys Val Tyr Ala Cys Glu Val Thr His Gln Gly Leu Ser
        195                 200                 205
Ser Pro Val Thr Lys Ser Phe Asn Arg Gly Glu Cys
    210                 215                 220

<210> SEQ ID NO 103
<211> LENGTH: 454
<212> TYPE: PRT
<213> ORGANISM: Artificial Sequence
<220> FEATURE:
<223> OTHER INFORMATION: H4H9816P2 Full length heavy chain
```

<400> SEQUENCE: 103

```
Glu Val Gln Leu Val Glu Ser Gly Gly Gly Leu Val Gln Pro Gly Gly
1               5                   10                  15

Ser Leu Thr Leu Ser Cys Ala Ala Ser Gly Phe Asn Phe Arg Asp Tyr
            20                  25                  30

Glu Met Ile Trp Val Arg Gln Thr Pro Gly Lys Gly Leu Glu Trp Ile
        35                  40                  45

Ser Tyr Ile Ser Asn Ser Gly Tyr Thr Ile Tyr Ala Asp Ser Val
    50                  55                  60

Lys Gly Arg Phe Thr Ile Ser Arg Asp Asn Ala Arg Asn Ser Ile Tyr
65                  70                  75                  80

Leu Gln Val Asn Ser Leu Arg Ala Glu Asp Thr Ala Val Tyr Tyr Cys
                85                  90                  95

Ser Arg Arg Thr Thr Met Ile Arg Gly Ile Arg Ala Tyr Tyr Tyr Tyr
            100                 105                 110

Gly Leu Asp Val Trp Gly Gln Gly Thr Thr Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
```

-continued

```
                 405                 410                 415
Leu Thr Val Asp Lys Ser Arg Trp Gln Glu Gly Asn Val Phe Ser Cys
            420                 425                 430

Ser Val Met His Glu Ala Leu His Asn Arg Phe Thr Gln Lys Ser Leu
        435                 440                 445

Ser Leu Ser Pro Gly Lys
    450

<210> SEQ ID NO 104
<211> LENGTH: 215
<212> TYPE: PRT
<213> ORGANISM: Artificial Sequence
<220> FEATURE:
<223> OTHER INFORMATION: H4H9816P2 Full length light chain

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

ANTI-TrkB MONOCLONAL ANTIBODIES AND METHODS OF USE

CROSS-REFERENCE

This application claims the benefit of U.S. provisional patent application Ser. No. 62/592,657 filed Nov. 30, 2017 which is incorporated by reference in its entirety.

FIELD OF THE INVENTION

The present invention relates to anti-tropomyosin-receptor-kinase B (TrkB) monoclonal antibodies. More specifically, the invention relates to compositions comprising anti-TrkB monoclonal antibodies and methods of using these antibodies.

BACKGROUND

Tropomyosin receptor kinase B (TrkB), belongs to a family of single transmembrane receptor tyrosine kinases, which includes TrkA and TrkC. These receptor kinases mediate the activity of neurotrophins, which are required for neuronal survival and development. Neurotrophins include, but are not limited to, nerve growth factor (NGF), brain derived neurotrophic factor (BDNF), neurotrophin-3 (NT-3), and neurotrophin-4/5 (NT-4/5). (Lo, K Y et al., J. Biol. Chem., 280:41744-52 (2005)).

TrkB is the high affinity receptor for BDNF (Minichiello, et al., Neuron 21:335-45 (1998)), but it is also known to bind NT4/5. The binding of BDNF to trkB causes the receptor to dimerize, resulting in the autophosphorylation of specific tyrosine residues on the receptor and activation of signaling pathways involving mitogen-activated protein kinase (MAPK), phosphatidylinositol 3-kinase (PI3K), and phospholipase C-γ (PLC-γ). (Jing, et al. Neuron 9:1067-1079 (1992); Barbacid, J. Neurobiol. 25:1386-1403 (1994); Bothwell, Ann. Rev. Neurosci. 18:223 253 (1995); Segal and Greenberg, Ann. Rev. Neurosci. 19:463 489 (1996); Kaplan and Miller, Curr. Opinion Neurobiol. 10:381 391 (2000)). After binding to BDNF, TrkB mediates the multiple effects of the neurotrophin, which includes neuronal differentiation and survival.

Since TrkB plays a major role in neuronal survival, differentiation, and function, TrkB agonists may have therapeutic potential for treating a number of neurodegenerative and metabolic disorders.

Certain TrkB agonists have been described in US2010/0150914; US2003/0157099; US2010/0196390 and US2017/0157099. However, there is still a need for the identification and development of additional TrkB agonists that provide improved specificity in addition to exhibiting neuronal survival and neuroprotective properties, such as those described herein.

BRIEF SUMMARY OF THE INVENTION

The present invention provides isolated monoclonal antibodies and antigen-binding fragments thereof that specifically bind to tropomyosin-receptor-kinase B (TrkB). The isolated antibodies and antigen-binding fragments of the invention are useful for treating diseases and disorders associated with TrkB activity or expression.

In its broadest aspect, the invention provides anti-TrkB agonist antibodies, which activate TrkB and promote neuronal survival. These antibodies may be used to improve nerve function and for treating any disease or disorder characterized in part by cellular degeneration, including nerve cell damage associated with nervous system injury and/or chronic neurodegenerative diseases.

In certain embodiments, the anti-TrkB antibodies may be useful to treat various diseases or disorders of the eye and may be formulated for intraocular or intravitreal delivery, in order to treat diseases of the eye, such as, but not limited to, glaucoma.

The antibodies of the invention can be full-length (for example, an IgG1 or IgG4 antibody) or may comprise only an antigen-binding portion (for example, a Fab, F(ab')2 or scFv fragment), and may be modified to affect functionality, e.g., to eliminate residual effector functions (Reddy et al., 2000, J. Immunol. 164:1925-1933).

Exemplary anti-TrkB antibodies of the present invention are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-TrkB antibodies. Table 2 sets forth the nucleic acid sequence identifiers of the HCVRs, LCVRs, HCDR1, HCDR2 HCDR3, LCDR1, LCDR2 and LCDR3 of the exemplary anti-TrkB antibodies.

The present invention provides antibodies or antigen-binding fragments thereof that specifically bind TrkB, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies or antigen-binding fragments thereof that specifically bind TrkB, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies or antigen-binding fragments thereof that specifically bind TrkB, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-TrkB antibodies listed in Table 1.

Accordingly, in a first aspect, the invention provides an isolated antibody or antigen-binding fragment thereof that binds specifically to tropomyosin receptor kinase B (TrkB), wherein the antibody or antigen-binding fragment thereof comprises three heavy chain complementarity determining regions (CDRs) (HCDR1, HCDR2 and HCDR3) contained within a heavy chain variable region (HCVR) comprising an amino acid sequence as set forth in Table 1, or a substantially similar sequence thereof having at least 90% sequence identity thereto; and three light chain CDRs (LCDR1, LCDR2 and LCDR3) contained within a light chain variable region (LCVR) comprising an amino acid sequence as set forth in Table 1, or a substantially similar sequence thereof having at least 90% sequence identity thereto.

In one embodiment, the anti-TrkB antibody or antigen-binding fragment thereof exhibits one or more properties selected from the group consisting of:
(a) is an agonist antibody;
(b) binds human TrkB with a $K_D$ of less than about 200 nM as measured by surface plasmon resonance at 25° C. or at 37° C.;
(c) binds human TrkB with a dissociative half life (t½) of greater than about 10 minutes as measured by surface plasmon resonance at 25° C. or at 37° C.;
(d) activates human TrkB signaling in the absence of brain derived neurotrophic factor (BDNF) in cells engineered to express human TrkB with an $EC_{50}$ ranging from about 35 to 82 pM;
(e) enhances TrkB phosphorylation when injected into the hippocampus of mice homozygous for human TrkB receptor ($TrkB^{hu/hu}$);
(f) promotes weight loss when injected into mice homozygous for human TrkB receptor ($TrkB^{hu/hu}$);
(g) increases retinal ganglion cell (RGC) survival as assessed in an optic nerve transection model in humanized TrkB rats;
(h) activates the MAPK/ERK and PI3K/Akt signaling pathways;
(i) increases survival of neuronal cells in vitro; and
(j) blocks the binding of TrkB to BDNF and/or NT-4 with an $IC_{50}$ of less than 5 nM.

In one embodiment, the invention provides an antibody or antigen-binding fragment thereof that specifically binds tropomyosin-receptor-kinase B (TrkB), wherein the antibody or antigen-binding fragment thereof comprises: (a) the complementarity determining regions (CDRs) of a heavy chain variable region (HCVR) comprising an amino acid sequence as set forth in Table 1; and (b) the CDRs of a light chain variable region (LCVR) comprising an amino acid sequence as set forth in Table 1.

In one embodiment, the antibody or antigen-binding fragment thereof that specifically binds TrkB comprises three heavy chain CDRs (HCDR1, HCDR2 and HCDR3) contained within any one of the HCVR sequences selected from the group consisting of SEQ ID NOs: 2, 18, 34, 49, 59 and 68, or a substantially similar sequence thereof having at least 90% sequence identity thereto; and three light chain CDRs (LCDR1, LCDR2 and LCDR3) contained within any one of the LCVR sequences selected from the group consisting of SEQ ID NOs: 10, 26, 42, 53, 63 and 72, or a substantially similar sequence thereof having at least 90% sequence identity thereto.

In one embodiment, the isolated antibody or antigen-binding fragment thereof that specifically binds TrkB comprises a HCVR having an amino acid sequence selected from the group consisting of SEQ ID NOs: 2, 18, 34, 49, 59 and 68.

In one embodiment, the isolated antibody or antigen-binding fragment thereof that specifically binds TrkB further comprises a LCVR having an amino acid sequence selected from the group consisting of SEQ ID NOs: 10, 26, 42, 53, 63 and 72.

In one embodiment, the isolated antibody or antigen-binding fragment thereof that specifically binds TrkB comprises a HCVR having an amino acid sequence selected from the group consisting of SEQ ID NOs: 2, 18, 34, 49, 59 and 68; and a LCVR having an amino acid sequence selected from the group consisting of SEQ ID NOs: 10, 26, 42, 53, 63 and 72.

In one embodiment, the isolated antibody or antigen-binding fragment thereof that specifically binds TrkB comprises the CDRs of a HCVR/LCVR amino acid sequence pair selected from the group consisting of SEQ ID NOs: 2/10, 18/26, 34/42, 49/53, 59/63 and 68/72.

In one embodiment, the isolated antibody or antigen-binding fragment thereof that specifically binds TrkB comprises: the CDRs of a HCVR/LCVR amino acid sequence pair selected from the group consisting of SEQ ID NOs: 2/10, 18/26, and 34/42.

In one embodiment, the isolated antibody or antigen-binding fragment thereof that specifically binds TrkB comprises an HCVR/LCVR amino acid sequence pair selected from the group consisting of SEQ ID NOs: 2/10, 18/26, 34/42, 49/53, 59/63 and 68/72.

In one embodiment, the isolated antibody or antigen-binding fragment thereof that specifically binds TrkB comprises an HCVR/LCVR amino acid sequence pair selected from the group consisting of SEQ ID NOs: 2/10, 18/26 and 34/42.

The present invention also provides antibodies or antigen-binding fragments thereof that specifically bind TrkB, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity thereto.

The present invention also provides antibodies or antigen-binding fragments thereof that specifically bind TrkB, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity thereto.

The present invention also provides antibodies or antigen-binding fragments thereof that specifically bind TrkB, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity thereto.

The present invention also provides antibodies or antigen-binding fragments thereof that specifically bind TrkB, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity thereto.

The present invention also provides antibodies or antigen-binding fragments thereof that specifically bind TrkB, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity thereto.

The present invention also provides antibodies or antigen-binding fragments thereof that specifically bind TrkB, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity thereto.

The present invention also provides antibodies or antigen-binding fragments thereof that specifically bind TrkB, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-TrkB antibodies listed in Table 1. In certain embodiments, the HCDR3/LCDR3 amino acid sequence pair is selected from the group consisting of: 8/16, 24/32, 40/48, 52/56, 62/66 and 71/75.

The present invention also provides antibodies or antigen-binding fragments thereof that specifically bind TrkB, comprising a set of six CDRs (i.e., HCDR1, HCDR2, HCDR3, LCDR1, LCDR2, LCDR3) contained within any of the exemplary anti-TrkB antibodies listed in Table 1. In certain embodiments, the HCDR1, HCDR2, HCDR3, LCDR1, LCDR2, LCDR3 amino acid sequence set is selected from the group consisting of: (a) SEQ ID NOs: 4, 6, 8, 12, 14, 16; (b) SEQ ID NOs: 20, 22, 24, 28, 30, 32; (c) SEQ ID NOs: 36, 38, 40, 44, 46, 48; (d) SEQ ID NOs: 50, 51, 52, 54, 55, 56; (e) SEQ ID NOs: 60, 61, 62, 64, 65, 66; and (f) SEQ ID NOs: 69, 70, 71, 73, 74, 75.

In a related embodiment, the present invention provides antibodies, or antigen-binding fragments thereof that specifically bind TrkB, comprising a set of six CDRs (i.e., HCDR1, HCDR2, HCDR3, LCDR1, LCDR2, LCDR3) contained within an HCVR/LCVR amino acid sequence pair as defined by any of the exemplary anti-TrkB antibodies listed in Table 1. For example, the present invention includes antibodies or antigen-binding fragments thereof that specifically bind TrkB, comprising the HCDR1, HCDR2, HCDR3, LCDR1, LCDR2, LCDR3 amino acid sequences set contained within an HCVR/LCVR amino acid sequence pair selected from the group consisting of: 2/10, 18/26, 34/42, 49/53, 59/63, and 68/72. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In one embodiment, the invention provides an isolated antibody or antigen-binding fragment thereof that specifically binds TrkB comprising:
(a) a HCDR1 domain having an amino acid sequence selected from the group consisting of SEQ ID NOs: 4, 20, 36, 50, 60 and 69;
(b) a HCDR2 domain having an amino acid sequence selected from the group consisting of SEQ ID NOs: 6, 22, 38, 51, 61 and 70;
(c) a HCDR3 domain having an amino acid sequence selected from the group consisting of SEQ ID NOs: 8, 24, 40, 52, 62 and 71;
(d) a LCDR1 domain having an amino acid sequence selected from the group consisting of SEQ ID NOs: 12, 28, 44, 54, 64 and 73;
(e) a LCDR2 domain having an amino acid sequence selected from the group consisting of SEQ ID NOs: 14, 30, 46, 55, 65 and 74; and
(f) a LCDR3 domain having an amino acid sequence selected from the group consisting of SEQ ID NOs: 16, 32, 48, 56, 66 and 75.

In one embodiment, the invention provides an isolated antibody or antigen-binding fragment thereof that specifically binds TrkB comprising:
(a) a HCDR1 domain having an amino acid sequence selected from the group consisting of SEQ ID NOs: 4, 20 and 36;
(b) a HCDR2 domain having an amino acid sequence selected from the group consisting of SEQ ID NOs: 6, 22 and 38;
(c) a HCDR3 domain having an amino acid sequence selected from the group consisting of SEQ ID NOs: 8, 24 and 40;
(d) a LCDR1 domain having an amino acid sequence selected from the group consisting of SEQ ID NOs: 12, 28 and 44;
(e) a LCDR2 domain having an amino acid sequence selected from the group consisting of SEQ ID NOs: 14, 30 and 46; and
(f) a LCDR3 domain having an amino acid sequence selected from the group consisting of SEQ ID NOs: 16, 32 and 48.

In one embodiment, the isolated antibody or antigen-binding fragment thereof comprises a set of six CDRs (HCDR1-HCDR2-HCDR3-LCDR1-LCDR2-LCDR3) selected from the group consisting of: (a) SEQ ID NOs: 4-6-8-12-14-16; (b) SEQ ID NOs: 20-22-24-28-30-32; (c) SEQ ID NOs: 36-38-40-44-46-48; (d) SEQ ID NOs: 50-51-52-54-55-56; (e) SEQ ID NOs: 60-61-62-64-65-66; and (f) SEQ ID NOs: 69-70-71-73-74-75.

In one embodiment, the isolated antibody or antigen-binding fragment thereof that binds to TrkB comprises an antibody or antigen-binding fragment thereof that competes for binding to TrkB with a reference antibody, wherein the reference antibody comprises an HCVR/LCVR amino acid sequence pair selected from the group consisting of SEQ ID NOs: 2/10, 18/26, 34/42, 49/53, 59/63 and 68/72.

In one embodiment, the isolated antibody or antigen-binding fragment thereof that binds to TrkB comprises an antibody or antigen-binding fragment thereof that binds to the same epitope as a reference antibody, wherein the reference antibody comprises an HCVR/LCVR amino acid sequence pair selected from the group consisting of SEQ ID NOs: 2/10, 18/26, 34/42, 49/53, 59/63 and 68/72.

In one embodiment, the isolated antibody or antigen-binding fragment thereof binds human TrkB with a $K_D$ of less than about 300 nM as measured by surface plasmon resonance at 25° C. or 37° C.

In one embodiment, the isolated antibody or antigen-binding fragment thereof binds human TrkB with a $K_D$ of less than about 200 nM as measured by surface plasmon resonance at 25° C. or 37° C.

In one embodiment, the isolated antibody or antigen-binding fragment thereof binds human TrkB with a $K_D$ of less than about 150 nM as measured by surface plasmon resonance at 25° C. or 37° C.

In one embodiment, the isolated antibody or antigen-binding fragment thereof binds human TrkB with a $K_D$ of less than about 50 nM as measured by surface plasmon resonance at 25° C. or 37° C.

In one embodiment, the isolated antibody or antigen-binding fragment thereof binds human TrkB with a $K_D$ of less than about 100 pM as measured by surface plasmon resonance at 25° C. or 37° C.

In one embodiment, the isolated antibody or antigen-binding fragment thereof binds human TrkB with a dissociative half life (t½) of greater than about 10 minutes as measured by surface plasmon resonance at 25° C. or 37° C.

In one embodiment, the isolated antibody or antigen-binding fragment thereof binds human TrkB with a t½ of greater than about 40 minutes as measured by surface plasmon resonance at 25° C. or 37° C.

In one embodiment, the isolated antibody or antigen-binding fragment thereof binds human TrkB with a t½ of greater than about 120 minutes as measured by surface plasmon resonance at 25° C. or 37° C.

In one embodiment, the isolated antibody or antigen-binding fragment thereof that binds to TrkB activates human TrkB signaling in the absence of BDNF in cells engineered to express TrkB, with an $EC_{50}$ of less than about 100 pM.

In one embodiment, the isolated antibody or antigen-binding fragment thereof that binds to TrkB activates human TrkB signaling in the absence of BDNF in cells engineered to express TrkB, with an $EC_{50}$ ranging from about 35 pM to about 82 pM.

In one embodiment, the isolated antibody or antigen-binding fragment thereof that binds to TrkB enhances activation of human TrkB signaling in the presence of BDNF in cells engineered to express TrkB, with an $EC_{50}$ of less than about 100 pM.

In one embodiment, the isolated antibody or antigen-binding fragment thereof that binds to TrkB, which when injected into the hippocampus of humanized TrkB mice, demonstrates TrkB activation, as shown by an increase in TrkB phosphorylation.

In one embodiment, the isolated antibody or antigen-binding fragment thereof that binds to TrkB demonstrates activation of the MAPK/ERK and PI3K/Akt signaling pathways, as demonstrated following incubation of primary mouse cortical neurons with an agonist anti-TrkB antibody.

In one embodiment, the isolated antibody or antigen-binding fragment thereof that binds to TrkB enhances/increases survival of retinal ganglion cells as shown in an optic nerve transection model in TrkB humanized rats.

In one embodiment, the isolated antibody or antigen-binding fragment thereof that binds to TrkB enhances/increases survival of neuronal cells in vitro.

In one embodiment, the isolated antibody or antigen-binding fragment thereof that binds to TrkB promotes weight loss in humanized TrkB mice.

In one embodiment, the isolated antibody or antigen-binding fragment thereof that binds to TrkB promotes a loss of fat mass in humanized TrkB mice.

In one embodiment, the isolated antibody or antigen-binding fragment thereof that binds to TrkB promotes a decrease in food and water consumption in humanized TrkB mice.

In one embodiment, the isolated antibody or antigen-binding fragment thereof that binds to TrkB promotes an increase in locomotor activity in humanized TrkB mice.

In one embodiment, the invention provides an anti-TrkB antibody or antigen-binding fragment thereof that specifically binds TrkB and blocks TrkB binding to BDNF with an $IC_{50}$ of less than about 5 nM.

In one embodiment, the invention provides an anti-TrkB antibody or antigen-binding fragment thereof that specifically binds TrkB and blocks TrkB binding to BDNF with an $IC_{50}$ of less than about 500 pM.

In one embodiment, the invention provides an anti-TrkB antibody or antigen-binding fragment thereof that specifically binds TrkB and blocks TrkB binding to BDNF with an $IC_{50}$ of less than about 200 pM.

In a second aspect, the present invention provides nucleic acid molecules encoding anti-TrkB antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1, HCDR2, HCDR3), wherein the HCDR1, HCDR2, HCDR3 amino acid sequence set is as defined by any of the exemplary anti-TRKB antibodies listed in Table 1.

The present invention also provides nucleic acid molecules encoding an LCVR, wherein the LCVR comprises a set of three CDRs (i.e., LCDR1, LCDR2, LCDR3), wherein the LCDR1, LCDR2, LCDR3 amino acid sequence set is as defined by any of the exemplary anti-TRKB antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-TrkB antibody listed in Table 1.

In a third aspect, the present invention provides recombinant expression vectors capable of expressing a polypeptide comprising a heavy or light chain variable region of an anti-TrkB antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

The present invention includes anti-TrkB antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In a fourth aspect, the invention provides a pharmaceutical composition comprising at least one antibody of the invention, or an antigen binding fragment thereof, which specifically binds TrkB and a pharmaceutically acceptable carrier.

In a related aspect, the invention features a composition, which is a combination of an anti-TrkB antibody and a second therapeutic agent. In one embodiment, the second therapeutic agent is any agent that is advantageously combined with an anti-TrkB antibody. The second therapeutic agent may be useful for alleviating at least one symptom of the neurodegenerative disease or disorder.

In a fifth aspect, the invention provides a method for enhancing a biological activity mediated by TrkB, the method comprising contacting TrkB with a biologically effective amount of an agonist anti-TrkB antibody of Table 1, or contacting TrkB with a pharmaceutical composition containing a biologically effective amount of an agonist anti-TrkB antibody of Table 1.

In certain embodiments, the biological activity is neuronal protection or neuronal survival and neuronal protection or neuronal survival is enhanced upon contact of TrkB with an agonist anti-TrkB antibody.

In certain embodiments, the biological activity is neuroprotection and survival of retinal ganglion cells (RGCs).

In a sixth aspect, the invention provides therapeutic methods for treating a disease or disorder associated with TrkB activity or expression, or at least one symptom associated with the disease or disorder, using an anti-TrkB antibody or antigen-binding portion of an antibody of the invention. The therapeutic methods according to this aspect of the invention comprise administering a therapeutically effective amount of a pharmaceutical composition comprising an antibody or antigen-binding fragment of an antibody of the invention to a subject in need thereof. The disorder treated is any disease or condition which is improved, ameliorated, inhibited or prevented by targeting TrkB and/or by activating TrkB-mediated cell signaling.

In one embodiment, the anti-TrkB antibodies of the invention may provide a method of preventing injury or death of retinal neurons. In one embodiment, the anti-TrkB antibodies of the invention may provide a method of treating pathological diseases wherein degeneration of the retina occurs. In one embodiment, the anti-TrkB antibodies of the invention may provide a method of treating the living eye prior to or following ocular surgery, exposure to light or other environmental trauma thereby preventing degeneration of retinal cells. In one embodiment, the anti-TrkB antibodies of the invention may provide a method of preventing photoreceptor injury and degeneration in the living eye. In one embodiment, the anti-TrkB antibodies of the invention may provide a method of protecting retinal neurons without the induction of side effects, possibly due to cross reactivity with other receptors, such as the p75 receptor. In one embodiment, the anti-TrkB antibodies of the invention may provide a method of allowing injured photoreceptors to recover or regenerate.

In certain embodiments, the disease or disorder to be treated with an antibody of the invention is a disease or disorder of the eye selected from the group consisting of glaucoma, diabetic retinopathy, age-related macular degeneration, ischemic optic neuropathy, optic neuritis, retinal ischemia, photoreceptor degeneration, retinitis pigmentosa, Leber Congenital Amaurosis, Leber's hereditary optic neuropathy, Usher Syndrome, Stargardt disease and retinal artery or vein occlusions.

Other pathological conditions treatable with one or more anti-TrkB antibodies of the invention include retinal detachment, photic retinopathies, surgery-induced retinopathies (either mechanically or light-induced), toxic retinopathies, retinopathy of prematurity, viral retinopathies such as CMV or HIV retinopathy related to AIDS; uveitis; ischemic retinopathies due to venous or arterial occlusion or other vascular disorder, retinopathies due to trauma or penetrating lesions of the eye, peripheral vitreoretinopathy or inherited retinal degenerations.

In one embodiment, the disease or disorder of the eye to be treated with an agonist anti-TrkB antibody of the invention is glaucoma.

A seventh aspect of the invention provides for achieving a reduction in body weight in a subject, the method comprising administering a TrkB agonist antibody of Table 1, or a pharmaceutical composition comprising the antibody or antigen-binding fragment thereof, to the subject.

In a related aspect, the invention provides a method for achieving a reduction of fat mass in a subject, the method comprising administering a TrkB agonist antibody of Table 1, or a pharmaceutical composition comprising the antibody or antigen-binding fragment thereof, to the subject.

An eighth aspect of the invention provides for a method of promoting neuronal survival in a subject, the method comprising administering a therapeutically effective amount of a TrkB agonist antibody of Table 1, or a pharmaceutical composition comprising a therapeutically effective amount of the antibody or antigen-binding fragment thereof, to the subject.

In one embodiment, the methods described above may be achieved by administering an agonist anti-TrkB antibody or antigen-binding fragment thereof to a subject in need thereof, wherein the agonist anti-TrkB antibody comprises three heavy chain complementarity determining regions (CDRs) (HCDR1, HCDR2 and HCDR3) contained within a heavy chain variable region (HCVR) comprising an amino acid sequence as set forth in Table 1, or a substantially similar sequence thereof having at least 90% sequence identity thereto; and three light chain CDRs (LCDR1, LCDR2 and LCDR3) contained within a light chain variable region (LCVR) comprising an amino acid sequence as set forth in Table 1, or a substantially similar sequence thereof having at least 90% sequence identity thereto.

In one embodiment, the methods of the invention may be achieved by administering an agonist TrkB antibody of the invention, wherein the antibody or antigen-binding fragment thereof comprises three heavy chain CDRs (HCDR1, HCDR2 and HCDR3) contained within any one of the HCVR sequences selected from the group consisting of SEQ ID NOs: 2, 18, 34, 49, 59 and 68, or a substantially similar sequence thereof having at least 90% sequence identity thereto; and three light chain CDRs (LCDR1, LCDR2 and LCDR3) contained within any one of the LCVR sequences selected from the group consisting of SEQ ID NOs: 10, 26, 42, 53, 63 and 72, or a substantially similar sequence thereof having at least 90% sequence identity thereto.

In one embodiment, the antibody or antigen-binding fragment thereof comprises a HCVR having an amino acid sequence selected from the group consisting of SEQ ID NOs: 2, 18, 34, 49, 59 and 68.

In one embodiment, the antibody or antigen-binding fragment thereof comprises a LCVR having an amino acid sequence selected from the group consisting of SEQ ID NOs: 10, 26, 42, 53, 63 and 72.

In one embodiment, the antibody or antigen-binding fragment thereof comprises a HCVR having an amino acid sequence selected from the group consisting of SEQ ID NOs: 2, 18, 34, 49, 59 and 68; and a LCVR having an amino acid sequence selected from the group consisting of SEQ ID NOs: 10, 26, 42, 53, 63 and 72.

In one embodiment, the antibody or antigen-binding fragment thereof comprises the CDRs of a HCVR/LCVR amino acid sequence pair selected from the group consisting of SEQ ID NOs: 2/10, 18/26, 34/42, 49/53, 59/63 and 68/72.

In one embodiment, the antibody or antigen-binding fragment thereof comprises a HCVR/LCVR amino acid sequence pair selected from the group consisting of SEQ ID NOs: 2/10, 18/26, 34/42, 49/53, 59/63 and 68/72.

In one embodiment, the antibody or antigen-binding fragment thereof comprises:
(a) a HCDR1 domain having an amino acid sequence selected from the group consisting of SEQ ID NOs: 4, 20, 36, 50, 60 and 69;
(b) a HCDR2 domain having an amino acid sequence selected from the group consisting of SEQ ID NOs: 6, 22, 38, 51, 61 and 70;
(c) a HCDR3 domain having an amino acid sequence selected from the group consisting of SEQ ID NOs: 8, 24, 40, 52, 62 and 71;
(d) a LCDR1 domain having an amino acid sequence selected from the group consisting of SEQ ID NOs: 12, 28, 44, 54, 64 and 73;
(e) a LCDR2 domain having an amino acid sequence selected from the group consisting of SEQ ID NOs: 14, 30, 46, 55, 65 and 74; and
(f) a LCDR3 domain having an amino acid sequence selected from the group consisting of SEQ ID NOs: 16, 32, 48, 56, 66 and 75.

In one embodiment, the antibody or antigen-binding fragment thereof comprises a set of six CDRs (HCDR1-HCDR2-HCDR3-LCDR1-LCDR2-LCDR3) selected from the group consisting of: (a) SEQ ID NOs: 4-6-8-12-14-16; (b) SEQ ID NOs: 20-22-24-28-30-32; (c) SEQ ID NOs: 36-38-40-44-46-48; (d) SEQ ID NOs: 50-51-52-54-55-56; (e) SEQ ID NOs: 60-61-62-64-65-66; and (f) SEQ ID NOs: 69-70-71-73-74-75.

In one embodiment, the disease or disorder to be treated with an anti-TrkB antibody of the invention is obesity, and any complication resulting from obesity.

It is envisioned that any disease or disorder associated with TrkB activity or expression is amenable to treatment with an antibody of the invention. These diseases may include any disease in which cellular degradation is evident, such as in a neurodegenerative condition, or following a nerve injury.

Other embodiments will become apparent from a review of the ensuing detailed description.

DETAILED DESCRIPTION

Figure 1:
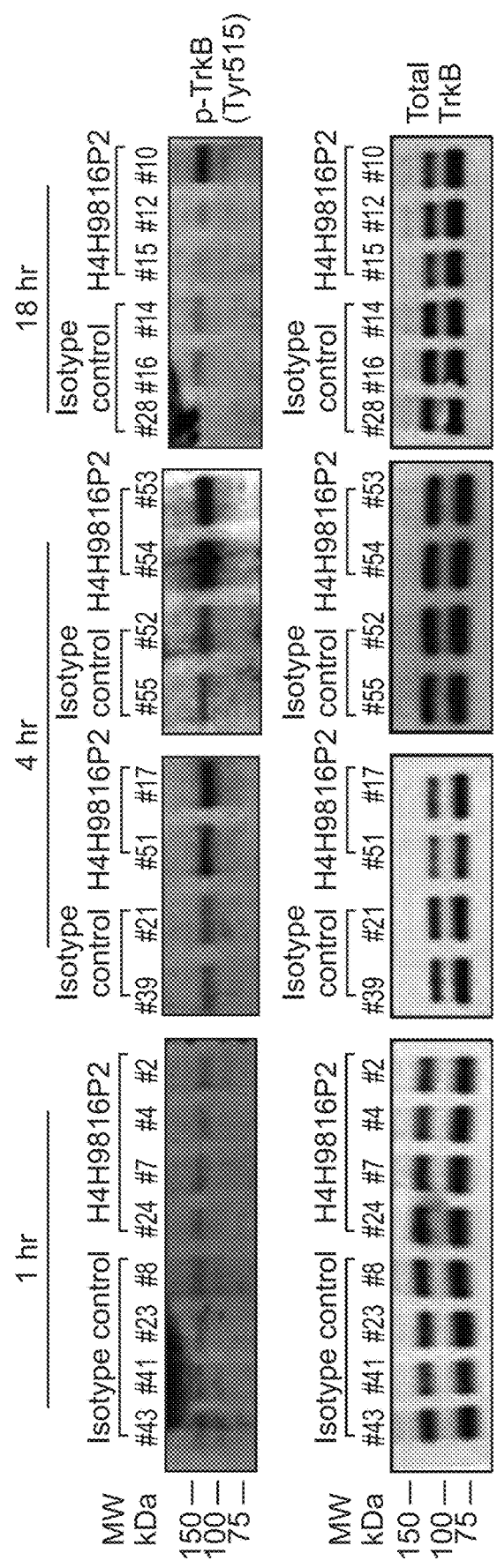
FIG. 1. Shows western blots assessing total TRKB levels and phospho-TRKB levels in homozygous humanized TRKB mice at 1 hour, 4 hours, and 18 hours following direct hippocampal injection of TRKB agonist antibody H4H9816P2 or isotype control antibody.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expression "TrkB," and the like, also known as "tropomyosin receptor kinase B", refers to the human receptor (unless designated as being from another species) comprising the amino acid sequence as set forth in amino acid residues 32 through 430 of accession number NP_001018074.1. Human TrkB containing a myc-myc-hexahistidine tag is shown as SEQ ID NO: 76 (with amino acid residues 1-399 being human TrkB and amino acid residues 400-427 being the myc-myc-hexahistidine tag). Other formats containing human TrkB proteins are described herein, including SEQ ID NO: 77, which is human TrkB (residues 1-399) with a mouse Fc region (residues 400-632); and SEQ ID NO: 78, which is human TrkB (residues 1-399) with a human Fc region (residues 400-626). Mouse TrkB comprises the amino acid sequence as set forth in amino acid residues 32 through 429 of accession number NP_001020245. Mouse TrkB containing a myc-myc-hexahistidine tag is shown as SEQ ID NO: 79 (with amino acid residues 1-398 being mouse TrkB and amino acid residues 399-426 being the myc-myc-hexahistidine tag). Other formats containing mouse TrkB proteins are described herein, including SEQ ID NO: 80, which is mouse TrkB (residues 1-398) with a mouse Fc region (residues 399-631); and SEQ ID NO: 81, which is mouse TrkB (residues 1-398) with a human Fc region (residues 399-625. Rabbit TrkB comprises the amino acid sequence as set forth in amino acid residues 32 through 430 of accession number XP_002721319.1. Rabbit TrkB containing a myc-myc-hexahistidine tag is shown as SEQ ID NO: 82 (with amino acid residues 1-399 being rabbit TrkB and amino acid residues 400-427 being the myc-myc-hexahistidine tag). Other formats containing rabbit TrkB proteins are described herein, including SEQ ID NO: 83, which is rabbit TrkB (residues 1-399) with a mouse Fc region (residues 400-632). Rat TrkB comprises the amino acid sequence as set forth in amino acid residues 32 through 429 of accession number NP_036863.1. Rat TrkB containing a myc-myc-hexahistidine tag is shown as SEQ ID NO: 84 (with amino acid residues 1-398 being rat TrkB and amino acid residues 399-426 being the myc-myc-hexahistidine tag). Other formats containing rat TrkB proteins are described herein, including SEQ ID NO: 85, which is rat TrkB (residues 1-398) with a mouse Fc region (residues 399-631). Rhesus macaque (*Macaca mulatta*) TrkB is shown as SEQ ID NO: 95 (amino acids 32 through 838 of accession number NP_001248226.1) and cynomolgus monkey (*Macaca fascicularis*) TrkB is shown as SEQ ID NO: 96 (amino acids 32 through 838 of accession number XP_055582102.1).

The human "TrkA" protein is shown as SEQ ID NO: 86, with amino acids 1-375 being TrkA (amino acids 34-414 of accession number NP_001012331.1 with V263L, C300S), amino acids 376-378 being a GPG linker and amino acids 379-605 being a human Fc.

The human "TrkC" protein is shown as SEQ ID NO: 87, with amino acids 1-398 being TrkC (amino acids 32-429 of accession number NP_001012338.1) and amino acids 399-426 being a myc-myc-his tag.

The mouse "TrkC" protein is shown as SEQ ID NO: 88, with amino acids 1-398 being TrkC (amino acids 32-429 of accession number NP_032772.3) and amino acids 399-426 being a myc-myc-his tag.

The cynomolgus monkey "TrkC" protein is shown as SEQ ID NO: 89, with amino acids 1-398 being TrkC (amino acids 32-429 of accession number XP_015308837.1) and amino acids 399-426 being a myc-myc-his tag.

In certain instances, cell lines were prepared that expressed the TrkB proteins, including the ecto domain, as well as the transmembrane and cytoplasmic domains of the TrkB protein. For example, SEQ ID NO: 91 is the human TrkB protein containing all three domains contained within amino acids 32-822 of accession number NP_001018074.1) or Uniprot Q16620-1, with amino acids 1-398 being the ecto domain, and the transmembrane/cytoplasmic region defined by about amino acid residues 399-790. In one instance, a TrkB cell line was prepared which expressed mouse TrkB (amino acids 32-476 of accession number NP_032771.1; See also SEQ ID NO: 92). In another instance, a cell line was prepared that expressed a chimeric TrkB protein, with the ecto domain of mouse TrkB from amino acids 32-429 of accession number NP_001020245.1 (See also SEQ ID NO: 93) or Uniprot number P15209-1 and the human TrkB transmembrane and cytoplasmic domains (amino acids 431-822 of accession number NP_001018074.1 (See also SEQ ID NO: 91). A cell line was also prepared that expressed African Green Monkey (*Chlorocebus sabaeus*) TrkB (amino acids 32-822 of accession number XP_007967815.1(See also SEQ ID NO: 94)).

The term "brain derived neurotrophic factor" or "BDNF" refers to the ligand for TrkB and the amino acid sequence of BDNF is shown in SEQ ID NO: 90 (isoform A 1-120, with amino acids 129-247 of accession number NP_733928.1 with a Met added onto the N-terminal). In certain experiments described herein, the source of the BDNF is from R & D Systems, 248-BD/CF.

All references to proteins, polypeptides and protein fragments herein are intended to refer to the human version of the respective protein, polypeptide or protein fragment unless explicitly specified as being from a non-human species. Thus, the expression "TrkB" means human TrkB unless specified as being from a non-human species, e.g., "monkey TrkB," "mouse TrkB," "rat TrkB," etc.

As used herein, the expression "anti-TrkB antibody" includes both monovalent antibodies with a single specificity, as well as bispecific antibodies comprising a first arm that binds TrkB and a second arm that binds a second (target) antigen, wherein the anti-TrkB arm comprises any of the HCVR/LCVR or CDR sequences as set forth in Table 1 herein. The expression "anti-TrkB antibody" also includes antibody-drug conjugates (ADCs) comprising an anti-TrkB antibody or antigen-binding portion thereof conjugated to a drug or toxin (i.e., cytotoxic agent). The expression "anti-TrkB antibody" also includes antibody-radionuclide conjugates (ARCs) comprising an anti-TrkB antibody or antigen-binding portion thereof conjugated to a radionuclide.

The term "anti-TrkB antibody", as used herein, means any antigen-binding molecule or molecular complex comprising at least one complementarity determining region (CDR) that specifically binds to or interacts with TrkB or a portion of TrkB. The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-TrkB antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full length antibody molecules. The terms "antigen-binding portion" of an antibody, "antigen-binding fragment" of an antibody, and the like, as used herein, include any enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (V) $V_H$-$C_H1$-$C_H2$-$C_H3$; (vi) $V_H$-$C_H2$-$C_H3$; (vii) $V_H$-CL; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

In certain instances, it may be desirable to antagonize TrkB, for example, for inhibiting the growth or proliferation of, for example, a neuronal tumor cell. However, the antibodies of the present invention act as agonist antibodies, which serve as enhancers of neuronal survival and as neuroprotectants. The antibodies of the present invention may function by enhancing the interaction between TrkB and its ligand, BDNF. Alternatively, the antibodies of the invention may mediate TrkB signaling through a mechanism that does not involve enhancing the TrkB interaction with its ligand The term "human antibody", as used herein, is intended to include non-naturally occurring human antibodies. The term includes antibodies that are recombinantly produced in a non-human mammal, or in cells of a non-human mammal. The term is not intended to include antibodies isolated from or generated in a human subject.

The antibodies of the invention may, in some embodiments, be recombinant and/or non-naturally occurring human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. In certain embodiments, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region, which may be desirable, for example, in production, to improve the yield of the desired antibody form.

The term "specifically binds", or "binds specifically to", or the like, means that an antibody or antigen-binding fragment thereof forms a complex with an antigen that is relatively stable under physiologic conditions. Specific binding can be characterized by an equilibrium dissociation constant of at least about $1 \times 10^{-6}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to TrkB. Moreover, multi-specific antibodies that bind to TrkB protein and one or more additional antigens or a bi-specific that binds to two different regions of TrkB are nonetheless considered antibodies that "specifically bind", as used herein.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The anti-TrkB antibodies disclosed herein may comprise one or more amino acid substitutions, insertions and/or deletions in the framework and/or CDR regions of the heavy and light chain variable domains. Such mutations can be readily ascertained by comparing the amino acid sequences disclosed herein to sequences available from, for example, public antibody sequence databases. Once obtained, antibodies and antigen-binding fragments that contain one or more mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-TrkB antibodies comprising variants of any of the HCVR, LCVR, and/or CDR amino acid sequences disclosed herein having one or more conservative substitutions. For example, the present invention includes anti-TrkB antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Biological Characteristics of the Antibodies

The present invention includes anti-TrkB antibodies that bind human TrkB with a $K_D$ of less than about 200 nM as measured by surface plasmon resonance at 25° C., or at 37° C. According to certain embodiments, the invention includes anti-TrkB antibodies that bind human TrkB with a $K_D$ of less than about 600 pM, less than about 300 pM, less than about 200 pM, less than about 150 pM, less than about 100 pM, less than about 80 pM, less than about 50 pM, less than about 40 pM, less than about 30 pM, less than about 20 pM, less than about 10 pM, less than about 5 pM, less than about 3 pM, or less than about 1 pM.

The present invention includes anti-TrkB antibodies that bind human TrkB with a dissociative half life (t½) of greater than about 10 minutes as measured by surface plasmon resonance at 25° C., or 37° C. According to certain embodiments, the invention includes anti-TrkB antibodies that bind human TrkB with a t1/2 of greater than about 20 minutes, greater than about 50 minutes, greater than about 100 minutes, greater than about 120 minutes, greater than about 150 minutes, greater than about 300 minutes, greater than about 350 minutes, greater than about 400 minutes, greater than about 450 minutes, greater than about 500 minutes, greater than about 550 minutes, greater than about 600 minutes, greater than about 700 minutes, greater than about 800 minutes, greater than about 900 minutes, greater than about 1000 minutes, greater than about 1100 minutes, or greater than about 1200 minutes.

The present invention includes anti-TrkB antibodies that may or may not bind monkey TrkB, or mouse or rat TrkB. As used herein, an antibody "does not bind" a particular antigen (e.g., monkey, mouse or rat TrkB if the antibody, when tested in an antigen binding assay such as surface plasmon resonance exhibits a $K_D$ of greater than about 1000 nM, or does not exhibit any antigen binding, in such an assay. Another assay format that can be used to determine whether an antibody binds or does not bind a particular antigen, according to this aspect of the invention, is ELISA.

The present invention includes anti-TrkB antibodies that activate human TrkB signaling in cells engineered to express an TrkB receptor with an $EC_{50}$ of less than about 100 pM. Using an assay format described in Example 5, or a substantially similar assay format, an $EC_{50}$ value can be calculated as the concentration of antibody required to activate TrkB-mediated signaling to the half-maximal signal observed. Thus, according to certain embodiments, the invention includes anti-TrkB antibodies that mediate human TrkB signaling in cells engineered to express a TrkB receptor in the presence or absence of BDNF with an $EC_{50}$ of less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, or less than about 5 pM, as measured using the assay format described in Example 5 herein or a substantially similar assay.

The present invention includes anti-TrkB antibodies that activate the TrkB receptor as shown by TrkB phosphorylation following direct hippocampal injection in mice humanized to express the human TrkB receptor, as shown in Example 6.

The present invention includes anti-TrkB antibodies that promote weight loss in mice humanized to express the human TrkB receptor. The antibodies of the invention also serve to promote loss of fat mass and increase locomotor activity in these mice, while decreasing food and water intake (see Example 7)

The antibodies of the invention promote survival of retinal ganglion cells (RGCs) in rats humanized to express the human TrkB receptor, when tested in an optic nerve transection model. See Example 8.

The antibodies of the invention activate the downstream pathways MAPK/ERK and PI3K/Akt, as shown by exposure of primary mouse cortical neurons obtained from humanized TrkB mice to the antibodies of the invention. (See Example 9).

The agonist anti-TrkB antibodies of the invention also promote survival of SH-SY5Y cells in a dose dependent fashion, as shown in Example 10.

The present invention includes anti-TrkB antibodies that block TrkB binding to BDNF with an $IC_{50}$ of less than about 5 nM. For example, as shown in Example 12, all three antibodies tested blocked >50% of mouse or rat TrkB binding to BDNF. Using the assay format described in Example 12, or a substantially similar assay format, an $IC_{50}$ value can be calculated as the concentration of antibody required to block TrkB binding to BDNF when compared to the maximal signal observed in the absence of antibody. Thus, according to certain embodiments, the invention includes anti-TrkB antibodies that block TrkB binding to BDNF with an $IC_{50}$ of less than about 5 nM, less than about 4 nM, less than about 3 nM, less than about 2 nM, less than about 1 nM, less than about 900 pM, less than about 800 pM, less than about 700 pM, less than about 600 pM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, or less than about 20 pM, as measured using the assay format described in Example 12 herein or a substantially similar assay. In one embodiment, the TrkB antibodies of the invention block TrkB binding to BDNF with an $IC_{50}$ ranging from about 180 pM to about 4 nM.

A binding characteristic of an antibody of the invention (e.g., any of the binding characteristics mentioned herein above), when disclosed in term of being "measured by surface plasmon resonance" means that the relevant binding characteristic pertaining to the interaction between the antibody and the antigen are measured using a surface plasmon resonance instrument (e.g., a Biacore® instrument, GE Healthcare) using standard Biacore assay conditions as illustrated in Examples 3 and 4 herein, or substantially similar assay format. In certain embodiments, the binding parameters are measured at 25° C., while in other embodiments, the binding parameters are measured at 37° C.

The present invention includes antibodies or antigen-binding fragments thereof that specifically bind TrkB, comprising an HCVR and/or an LCVR comprising an amino acid sequence selected from any of the HCVR and/or LCVR amino acid sequences listed in Table 1.

The antibodies of the present invention may possess one or more of the aforementioned biological characteristics, or any combination thereof. The foregoing list of biological characteristics of the antibodies of the invention is not intended to be exhaustive. Other biological characteristics of the antibodies of the present invention will be evident to a person of ordinary skill in the art from a review of the present disclosure including the working Examples herein.

Epitope Mapping and Related Technologies

The epitope to which the antibodies of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of a TrkB protein. Alternatively, the epitope may consist of a plurality of non-contiguous amino acids (or amino acid sequences) of TrkB. In some embodiments, the epitope is located on or near a surface of TrkB, for example, in the domain that interacts with its ligand, BDNF. In other embodiments, the epitope is located on or near a surface of TrkB that does not interact with the TrkB ligand, e.g., at a location on the surface of TrkB at which an antibody, when bound to such an epitope, does not interfere with the interaction between TrkB and its ligand.

Various techniques known to persons of ordinary skill in the art can be used to determine whether an antibody "interacts with one or more amino acids" within a polypeptide or protein. Exemplary techniques include, e.g., routine cross-blocking assay such as that described *Antibodies*, Harlow and Lane (Cold Spring Harbor Press, Cold Spring Harb., NY), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A.

The present invention includes anti-TrkB antibodies that bind to the same epitope as any of the specific exemplary antibodies described herein (e.g. antibodies comprising any of the amino acid sequences as set forth in Table 1 herein). Likewise, the present invention also includes anti-TrkB antibodies that compete for binding to TrkB with any of the specific exemplary antibodies described herein (e.g. antibodies comprising any of the amino acid sequences as set forth in Table 1 herein).

One can easily determine whether an antibody binds to the same epitope as, or competes for binding with, a reference anti-TrkB antibody by using routine methods known in the art and exemplified herein. For example, to determine if a test antibody binds to the same epitope as a reference anti-TrkB antibody of the invention, the reference antibody is allowed to bind to an TrkB protein. Next, the ability of a test antibody to bind to the TrkB molecule is assessed. If the test antibody is able to bind to TrkB following saturation binding with the reference anti-TrkB antibody, it can be concluded that the test antibody binds to a different epitope than the reference anti-TrkB antibody. On the other hand, if the test antibody is not able to bind to the TrkB molecule following saturation binding with the reference anti-TrkB antibody, then the test antibody may bind to the same epitope as the epitope bound by the reference anti-TrkB antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-TrkB antibody, the above-described binding methodology is performed in two orientations: In a first orientation, the reference antibody is allowed to bind to an TrkB protein under saturating conditions followed by assessment of binding of the test antibody to the TrkB molecule. In a second orientation, the test antibody is allowed to bind to a TrkB molecule under saturating conditions followed by assessment of binding of the reference antibody to the TrkB molecule. If, in both orientations, only the first (saturating) antibody is capable of binding to the TrkB molecule, then it is concluded that the test antibody and the reference antibody compete for binding to TrkB (see, e.g., the assay format described in Example 4 herein, in which TrkB protein is captured onto sensor tips and the TrkB-coated sensor tips are treated with a reference antibody [mAb-1] and a test anti-TrkB antibody [mAb-2] sequentially and in both binding orders). As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

The anti-TrkB antibodies of the present invention can be fully human but non-naturally occurring, antibodies. Methods for generating monoclonal antibodies, including fully human monoclonal antibodies are known in the art. Any such known methods can be used in the context of the present invention to make human antibodies that specifically bind to human TrkB.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to an allergen are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

As described in the experimental section below, the high affinity chimeric antibodies, which are isolated having a human variable region and a mouse constant region, are characterized and selected for desirable characteristics, including affinity, selectivity, epitope, etc. The mouse constant regions are then replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In certain embodiments, it may be desirable to test anti-human TrkB antibodies in mice or rats that have been engineered to express a human TrkB receptor. These mice or rats may be beneficial in circumstances wherein the anti-TrkB antibodies may only bind human TrkB, but will not cross react with mouse or rat TrkB. Certain examples in the present invention were carried out using mice and rats that were genetically modified to express the human trkB. Any method known to those skilled in the art may be used for generating such TrkB humanized mice and rats.

In general, the antibodies of the instant invention possess very high affinities, typically possessing $K_D$ of from about $10^{-12}$ through about $10^{-9}$ M, when measured by binding to antigen either immobilized on solid phase or in solution phase.

Bioequivalents

The anti-TrkB antibodies and antibody fragments of the present invention encompass proteins having amino acid sequences that vary from those of the described antibodies but that retain the ability to bind human TrkB. Such variant antibodies and antibody fragments comprise one or more additions, deletions, or substitutions of amino acids when compared to parent sequence, but exhibit biological activity that is essentially equivalent to that of the described antibodies. Likewise, the anti-TrkB antibody-encoding DNA sequences of the present invention encompass sequences that comprise one or more additions, deletions, or substitutions of nucleotides when compared to the disclosed sequence, but that encode an anti-TrkB antibody or antibody fragment that is essentially bioequivalent to an anti-TrkB antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-TrkB antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-TrkB antibody variants comprising amino acid changes which modify the glycosylation characteristics of the antibodies, e.g., mutations which eliminate or remove glycosylation.

Species Selectivity and Species Cross-Reactivity

The present invention, according to certain embodiments, provides anti-TrkB antibodies that bind to human TrkB but not to TrkB from other species. The present invention also includes anti-TrkB antibodies that bind to human TrkB and to TrkB from one or more non-human species. For example, the anti-TrkB antibodies of the invention may bind to human TrkB and may bind or not bind, as the case may be, to one or more of mouse, rat, guinea pig, hamster, gerbil, pig, cat, dog, rabbit, goat, sheep, cow, horse, camel, cynomologous, marmoset, rhesus or chimpanzee TrkB. According to certain exemplary embodiments of the present invention, anti-TrkB antibodies are provided which specifically bind human TrkB but do not bind, or bind only weakly, to mouse or rat TrkB.

Multispecific Antibodies

The antibodies of the present invention may be mono specific or multispecific (e.g., bispecific). Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-TrkB antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity.

The present invention includes bispecific antibodies wherein one arm of an immunoglobulin binds human TrkB, and the other arm of the immunoglobulin is specific for a second antigen. The TrkB-binding arm can comprise any of the HCVR/LCVR or CDR amino acid sequences as set forth in Table 1 herein.

An exemplary bispecific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bispecific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Formulation and Administration

The invention provides pharmaceutical compositions comprising the anti-TrkB antibodies or antigen-binding fragments thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA These formulations include, for example, powders, pastes, ointments, jellies, waxes, oils, lipids, lipid (cationic or anionic) containing vesicles (such as LIPOFECTIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. In an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-TrkB antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intravitreal, intraocular, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to, the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.), and the HUMIRA™ Pen (Abbott Labs, Abbott Park IL), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, intravitreal, intraocular, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The present invention includes methods comprising administering to a subject in need thereof a therapeutic composition comprising an anti-TrkB antibody (e.g., an anti-TrkB antibody comprising any of the HCVR/LCVR or CDR sequences as set forth in Table 1 herein). The therapeutic composition can comprise any one or more of the anti-TrkB antibodies or antigen-binding fragments thereof disclosed herein, and a pharmaceutically acceptable carrier or diluent.

The antibodies of the invention are useful, inter alia, for the treatment, prevention and/or amelioration of any disease or disorder associated with or mediated by TrkB expression or activity. The TrkB agonist antibodies of the invention may be used to improve nerve function and may be used to treat or prevent any disease or condition that is characterized in part by cellular degradation, in particular by nerve cell injury or nerve cell degeneration, e.g. an acute nervous system injury or a chronic neurodegenerative disease.

The present invention includes methods of treating or preventing a disease or disorder of the eye by administering to a patient in need of such treatment an anti-TrkB antibody or antigen-binding fragment thereof as disclosed elsewhere herein.

In one embodiment, the anti-TrkB antibodies of the invention may provide a method of preventing injury or death of retinal neurons. In one embodiment, the anti-TrkB antibodies of the invention may provide a method of treating pathological diseases wherein degeneration of the retina occurs. In one embodiment, the anti-TrkB antibodies of the invention may provide a method of treating the eye prior to or following ocular surgery, exposure to light or other environmental trauma thereby preventing degeneration of retinal cells. In one embodiment, the anti-TrkB antibodies of the invention may provide a method of preventing photoreceptor injury and degeneration in the eye. In one embodiment, the anti-TrkB antibodies of the invention may provide a method of protecting retinal neurons without the induction of side effects. In one embodiment, the anti-TrkB antibodies of the invention may provide a method of allowing injured photoreceptors to recover or regenerate.

In certain embodiments, the eye diseases treatable by using one or more of the anti-TrkB antibodies of the invention may be selected from the group consisting of glaucoma, diabetic retinopathy, age-related macular degeneration or other maculopathies, ischemic optic neuropathy, optic neuritis, retinal ischemia, photoreceptor degeneration, retinitis pigmentosa, Leber Congenital Amaurosis, Leber's hereditary optic neuropathy, Usher Syndrome, Stargardt disease, and retinal artery or vein occlusions.

Other pathological conditions treatable with one or more anti-TrkB antibodies of the invention include retinal detachment, photic retinopathies, surgery-induced retinopathies (either mechanically or light-induced), toxic retinopathies, retinopathy of prematurity, viral retinopathies such as CMV or HIV retinopathy related to AIDS; uveitis; ischemic retinopathies due to venous or arterial occlusion or other vascular disorder, retinopathies due to trauma or penetrating lesions of the eye, peripheral vitreoretinopathy or inherited retinal degenerations.

In one embodiment, the anti-TrkB antibodies of the invention may be formulated for intraocular or intravitreal delivery.

The present invention also provides methods for treating other central or peripheral nervous system diseases or disorders, such as stroke, or traumatic brain injury. Furthermore, since the antibodies of the present invention act to promote neuronal survival and act as neuroprotectants, any one or more of these agonist antibodies may prove to be beneficial in treating a patient suffering from a nervous system disease or disorder whereby neuronal survival is of prime importance in recovery or repair of the cellular damage caused by an injury to the nervous system, or caused by a disease that has a major effect on the nervous system, including neurodegenerative diseases.

In the context of the methods of treatment described herein, the anti-TrkB antibody may be administered as a monotherapy (i.e., as the only therapeutic agent) or in combination with one or more additional therapeutic agents.

Combination Therapies and Formulations

The present invention includes compositions and therapeutic formulations comprising any of the anti-TrkB antibodies described herein in combination with one or more additional therapeutically active components, and methods of treatment comprising administering such combinations to subjects in need thereof.

The anti-TrkB antibodies of the present invention may be co-formulated with and/or administered in combination with one or more additional therapeutically active component(s) selected from the group consisting of: a drug that helps to lower intraocular pressure (an IOP lowering drug), a neurotrophin, and an antagonist of vascular endothelial growth factor (VEGF), such as a VEGF trap, e.g. aflibercept (EYLEA®). Other medications that may be combined with the TrkB antibodies of the invention include, but are not limited to, a prostaglandin analog (e.g. ZIOPTAN™, XALATAN®), a beta blocker, (e.g. TIMOPTIC XE®, ISTALOL®, BETOPTIC®S); an alpha-2 adrenergic agonist (e.g. apraclonidine), carbonic anhydrase inhibitors (e.g. TRUSOPT®, AZOPT®), a cholinergic agent (e.g. ISOPTO®CARPINE, PILOPINE HS® gel), or a combined therapeutic (a beta blocker plus a carbonic anhydrase inhibitor, e.g. COMBIGAN™, COS OPT®).

The anti-TrkB antibodies of the invention may also be administered and/or co-formulated in combination with antivirals, antibiotics, analgesics, antioxidants, COX inhibitors, and/or NSAIDs. The anti-TrkB antibodies may also be used in conjunction with other types of therapy including stem cell therapy, glaucoma filtration surgery, laser surgery, or gene therapy.

The additional therapeutically active component(s), e.g., any of the agents listed above or derivatives thereof, may be administered just prior to, concurrent with, or shortly after the administration of an anti-TrkB antibody of the present invention; (for purposes of the present disclosure, such administration regimens are considered the administration of an anti-TrkB antibody "in combination with" an additional therapeutically active component). The present invention includes pharmaceutical compositions in which an anti-TrkB antibody of the present invention is co-formulated with one or more of the additional therapeutically active component(s) as described elsewhere herein.

Administration Regimens

According to certain embodiments of the present invention, multiple doses of an anti-TrkB antibody (or a pharmaceutical composition comprising a combination of an anti-TrkB antibody and any of the additional therapeutically active agents mentioned herein) may be administered to a subject over a defined time course. The methods according to this aspect of the invention comprise sequentially administering to a subject multiple doses of an anti-TrkB antibody of the invention. As used herein, "sequentially administering" means that each dose of anti-TrkB antibody is administered to the subject at a different point in time, e.g., on different days separated by a predetermined interval (e.g., hours, days, weeks or months). The present invention includes methods which comprise sequentially administering to the patient a single initial dose of an anti-TrkB antibody, followed by one or more secondary doses of the anti-TrkB antibody, and optionally followed by one or more tertiary doses of the anti-TrkB antibody.

The terms "initial dose," "secondary doses," and "tertiary doses," refer to the temporal sequence of administration of the anti-TrkB antibody of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-TrkB antibody, but generally may differ from one another in terms of frequency of administration. In certain embodiments, however, the amount of anti-TrkB antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-TrkB antibody, which is administered to a patient prior to the administration of the very next dose in the sequence with no intervening doses.

The methods according to this aspect of the invention may comprise administering to a patient any number of secondary and/or tertiary doses of an anti-TrkB antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient. The administration regimen may be carried out indefinitely over the lifetime of a particular subject, or until such treatment is no longer therapeutically needed or advantageous.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect of the invention, if the loading doses are administered at a frequency of once a month, then the maintenance doses may be administered to the patient once every six weeks, once every two months, once every three months, etc.

Diagnostic Uses of the Antibodies

The anti-TrkB antibodies of the present invention may also be used to detect and/or measure TrkB, or TrkB-expressing cells in a sample, e.g., for diagnostic purposes. For example, an anti-TrkB antibody, or fragment thereof, may be used to diagnose a condition or disease characterized by aberrant expression (e.g., over-expression, under-expression, lack of expression, etc.) of TrkB. Exemplary diagnostic assays for TrkB may comprise, e.g., contacting a sample, obtained from a patient, with an anti-TrkB antibody of the invention, wherein the anti-TrkB antibody is labeled with a detectable label or reporter molecule. Alternatively, an unlabeled anti-TrkB antibody can be used in diagnostic applications in combination with a secondary antibody which is itself detectably labeled. The detectable label or reporter molecule can be a radioisotope, such as 3H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure TrkB in a sample include enzyme-linked immunosorbent assay (ELISA), radioimmunoassay (RIA), and fluorescence-activated cell sorting (FACS).

Samples that can be used in TrkB diagnostic assays according to the present invention include any tissue or fluid sample obtainable from a patient, which contains detectable quantities of TrkB protein, or fragments thereof, under normal or pathological conditions. Generally, levels of TrkB in a particular sample obtained from a healthy patient (e.g., a patient not afflicted with a disease or condition associated with abnormal TrkB levels or activity) will be measured to initially establish a baseline, or standard, level of TrkB. This baseline level of TrkB can then be compared against the levels of TrkB measured in samples obtained from individuals suspected of having a TrkB related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies to TrkB

Human antibodies to TrkB were generated in a mouse comprising DNA encoding human immunoglobulin heavy and kappa light chain variable regions. In one embodiment, the human antibodies were generated in a VELOCIMMUNE® mouse. In one embodiment, VelocImmune® (VI) mice were immunized with human TrkB(ecto)mFc (SEQ ID NO: 77). In one embodiment, VelocImmune® (VI) mice were immunized with mouse TrkB(ecto)mFc (SEQ ID NO: 80). The antibody immune response was monitored by TrkB specific immunoassay. For example, sera were assayed for specific antibody titers to purified full-length TrkB. Antibody-producing clones were isolated using both B-cell Sorting Technology (BST) and hybridoma methods. For example, when a desired immune response was achieved, splenocytes were harvested and fused with mouse myeloma cells to preserve their viability and form hybridoma cell lines. The hybridoma cell lines were screened and selected to identify cell lines that produce TrkB-specific antibodies. Certain anti-mouse TrkB antibodies were generated this way and are designated M2aM14173N, M2aM14178N and M2aM14179N.

Anti-TrkB antibodies were also isolated directly from antigen-positive mouse B cells without fusion to myeloma cells, as described in U.S. Pat. No. 7,582,298, herein specifically incorporated by reference in its entirety. Using this method, several fully human anti-TrkB antibodies (i.e., antibodies possessing human variable domains and human constant domains) were obtained; exemplary antibodies generated in this manner were designated as H4H9780P, H4H9814P and H4H9816P2.

The biological properties of the exemplary antibodies generated in accordance with the methods of this Example are described in detail in the Examples set forth below.

Example 2: Heavy and Light Chain Variable Region Amino Acid and Nucleotide Sequences Table 1a sets forth the amino acid sequence identifiers of the heavy and light chain variable regions and CDRs of selected anti-TrkB antibodies of the invention. Table 1b sets forth the amino acid sequence identifiers for the full length heavy and light chains of selected anti-TrkB antibodies of the invention. The corresponding nucleic acid sequence identifiers for selected anti-TrkB antibodies of the invention are set forth in Table 2.

TABLE 1a

| Amino Acid Sequence Identifiers | | | | | | | | | | |
|---|---|---|---|---|---|---|---|---|---|---|
| Ab Name | HCVR | HCDR1 | HCDR2 | HCDR3 | LCVR | LCDR1 | LCDR2 | LCDR3 | mIgG2a | Constant LC |
| H4H9780P | 2 | 4 | 6 | 8 | 10 | 12 | 14 | 16 | | |
| H4H9814P | 18 | 20 | 22 | 24 | 26 | 28 | 30 | 32 | | |
| H4H9816P2 | 34 | 36 | 38 | 40 | 42 | 44 | 46 | 48 | | |
| M2aM14173N | 49 | 50 | 51 | 52 | 53 | 54 | 55 | 56 | 57 | 58 |
| M2aM14178N | 59 | 60 | 61 | 62 | 63 | 64 | 65 | 66 | 57 | 67 |
| M2aM14179N | 68 | 69 | 70 | 71 | 72 | 73 | 74 | 75 | 57 | 58 |

TABLE 1b

| Ab Name | Full length heavy chain | Full length light chain |
|---|---|---|
| H4H9780P | 99 | 100 |
| H4H9814P | 101 | 102 |
| H4H9816P2 | 103 | 104 |

TABLE 2

| Nucleic Acid Sequence Identifiers | | | | | | | | |
|---|---|---|---|---|---|---|---|---|
| Ab Name | VH | HCDR1 | HCDR2 | HCDR3 | VK | LCDR1 | LCDR2 | LCDR3 |
| H4H9780P | 1 | 3 | 5 | 7 | 9 | 11 | 13 | 15 |
| H4H9814P | 17 | 19 | 21 | 23 | 25 | 27 | 29 | 31 |
| H4H9816P2 | 33 | 35 | 37 | 39 | 41 | 43 | 45 | 47 |

Antibodies are typically referred to herein according to the following nomenclature: Fc prefix (e.g. "H4H," "H2M," etc.), followed by a numerical identifier (e.g. "9780," "9816," etc., as shown in Table 1 or 2), followed by a "P," "P2," or "N" suffix. The H4H prefix on the antibody designations indicate the particular Fc region isotype of the antibody. Thus, according to this nomenclature, an antibody may be referred to herein as, e.g., "H4H9780P", which indicates a human IgG4 Fc region and M2aM14179N, for example, indicates a mouse IgG2a Fc region. Variable regions are fully human if denoted by the first 'H' in the antibody designation. An 'M' prefix designates a mouse variable region. As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 1 or 2—will remain the same, and the binding properties to antigen are expected to be identical or substantially similar regardless of the nature of the Fc domain.

Example 3. Biacore Binding Kinetics of Anti-TrkB Monoclonal Antibodies Binding to Different TrkB Reagents Measured at 25° C. and 37° C.

Equilibrium dissociation constants ($K_D$ values) for TrkB binding to purified anti-TrkB monoclonal antibodies were determined using a real-time surface plasmon resonance biosensor using a Biacore 4000 instrument. All binding studies were performed in 10 mM Hepes pH 7.4, 150 mM NaCl, 3 mM EDTA, and 0.05% v/v Surfactant Tween-20 (HBS-ET running buffer) at 25° C. and 37° C. The Biacore sensor surface was first derivatized by amine coupling with F(ab')2 fragment goat anti-human Fcγ specific polyclonal antibody (Jackson ImmunoResearch Laboratories, #109-006-098) or rabbit anti-mouse Fc polyclonal antibody (GE Healthcare #BR-1008-38) to capture anti-TrkB monoclonal antibodies. Binding studies were performed on following TrkB reagents; human TrkB extracellular domain expressed with a C-terminal myc-myc-hexahistidine tag (hTRKB.mmH; SEQ ID NO: 76; Accession number NP_001018074.1), mouse TrkB extracellular domain expressed with a C-terminal myc-myc-hexahistidine tag (mTRKB.mmH; SEQ ID NO: 79; Accession number NP_001020245), rat TrkB extracellular domain expressed with a C-terminal myc-myc-hexahistidine tag (rTRKB.mmH; SEQ ID NO: 84; Accession number NP_036863.1), and human TrkB extracellular domain expressed with a C-terminal mouse IgG2a Fc tag (hTrkB-mFc; SEQ ID NO: 77; Accession number NP_001018074.1). Different concentrations of TrkB reagents were first prepared in HBS-ET running buffer (100 nM–1.23 nM; 3-fold serial dilution) and were injected over anti-human Fc captured anti-TrkB monoclonal antibody surface for 4 minutes at a flow rate of 30 μL/minute, while the dissociation of monoclonal antibody bound TrkB reagent was monitored for 10 minutes in HBS-ET running buffer. Kinetic association ($k_a$) and dissociation ($k_d$) rate constants were determined by fitting the real-time binding sensor-grams to a 1:1 binding model with mass transport limitation using Scrubber 2.0c curve-fitting software. Binding dissociation equilibrium constants ($K_D$) and dissociative half-lives (t½) were calculated from the kinetic rate constants as:

$$K_D(M) = \frac{kd}{ka}, \text{ and } t1/2(\min) = \frac{\ln(2)}{60 \times kd}$$

Binding kinetic parameters for hTrkB.mmH, mTrkB.mmH, rTrkB.mmH, or hTrkB-mFc binding to different anti-TrkB monoclonal antibodies of the invention at 25° C. and 37° C. are shown in Tables 3 through 10.
Summary of Results:

At 25° C., anti-TrkB monoclonal antibodies bound to hTrkB.mmH with KD values ranging from 545 pM to 41.3 nM, as shown in Table 3. At 37° C., monoclonal antibodies bound to hTrkB.mmH with KD values ranging from 2.28 nM to 135 nM, as shown in Table 4.

At 25° C., anti-TrkB monoclonal antibodies bound to hTrkB-mFc with KD values ranging from 31.1 pM to 4.48 nM, as shown in Table 5. At 37° C., anti-TrkB monoclonal antibodies bound to hTrkB-mFc with KD values ranging from 73.3 pM to 3.46 nM, as shown in Table 6.

At 25° C., the comparator anti-TrkB monoclonal antibody, referred to herein as H1M8037C, (See US2010/0196390, the antibody designated as C2; See also SEQ ID NOs: 97 and 98 for the comparator heavy and light chain, respectively, amino acid sequences) bound to mTrkB.mmH with a KD value of 40.8 nM, as shown in Table 7. The anti-TrkB antibodies of the invention did not bind to mTrkB.mmH at 25° C., as shown in Table 7. At 37° C., the comparator anti-TrkB monoclonal antibody bound to mTrkB.mmH with a KD value of 94.1 nM, as shown in Table 8. The anti-TrkB antibodies of the invention did not bind to mTrkB.mmH at 37° C., as shown in Table 8.

At 25° C., the comparator anti-TrkB monoclonal antibody bound to rTrkB.mmH with a KD value of 31.8 nM, as shown in Table 9. The anti-TrkB antibodies of the invention did not bind to rTrkB.mmH at 25° C., as shown in Table 9. At 37° C., the comparator anti-TrkB monoclonal antibody bound to rTrkB.mmH with a KD value of 87.5 nM, as shown in Table 10. The anti-TrkB antibodies of the invention did not bind to rTrkB.mmH at 37° C., as shown in Table 10.

TABLE 3

Binding kinetics parameters of hTrkB.mmH binding to TrkB monoclonal antibodies at 25° C.

| Captured Analyte | Amount of Analyte Captured (RU) | 100 nM hTrkB.mmH Bound (RU) | $k_a$ (1/Ms) | $k_d$ (1/s) | $K_D$ (M) | $t_{1/2}$ (min) |
|---|---|---|---|---|---|---|
| H4H9780P | 116 ± 2.8 | 20 | 4.00E+04 | 8.67E−04 | 2.17E−08 | 13 |
| H4H9814P | 93 ± 2.1 | 63 | 1.26E+06 | 6.86E−04 | 5.45E−10 | 17 |
| H4H9816P2 | 138 ± 1.5 | 30 | 6.14E+04 | 8.45E−04 | 1.38E−08 | 14 |
| H1M8037C* Comparator | 757 | 23 | 4.65E+04 | 1.92E−03 | 4.13E−08 | 6 |

*indicates that mAb was captured using anti-mFc immobilized surface

TABLE 4

Binding kinetics parameters of hTrkB.mmH binding to TrkB monoclonal antibodies at 37° C.

| Captured Analyte | Amount of Analyte Captured (RU) | 100 nM hTrkB.mmH Bound (RU) | $k_a$ (1/Ms) | $k_d$ (1/s) | $K_D$ (M) | $t_{1/2}$ (min) |
|---|---|---|---|---|---|---|
| H4H9780P | 64 ± 1.9 | 14 | 5.71E+04 | 3.64E−03 | 6.38E−08 | 3.2 |
| H4H9814P | 52 ± 1.2 | 32 | 2.05E+06 | 4.68E−03 | 2.28E−09 | 2.5 |
| H4H9816P2 | 80 ± 2.3 | 12 | 5.28E+04 | 3.74E−03 | 7.08E−08 | 3.1 |
| H1M8037C* Comparator | 815.11 | 28 | 6.13E+04 | 8.31E−03 | 1.35E−07 | 1.4 |

*indicates that mAb was captured using anti-mFc immobilized surface

TABLE 5

Binding kinetics parameters of hTrkB-mFc binding to TrkB monoclonal antibodies at 25° C.

| Captured Analyte | Amount of Analyte Captured (RU) | 100 nM hTrkB-mFc Bound (RU) | $k_a$ (1/Ms) | $k_d$ (1/s) | $K_D$ (M) | $t_{1/2}$ (min) |
|---|---|---|---|---|---|---|
| H4H9780P | 105 ± 1.6 | 14 | 3.74E+04 | 1.68E−04 | 4.48E−09 | 69 |
| H4H9814P | 83 ± 1.3 | 69 | 1.91E+06 | 5.95E−05 | 3.11E−11 | 194 |
| H4H9816P2 | 131 ± 1 | 25 | 6.52E+04 | 7.98E−05 | 1.22E−09 | 145 |
| H1M8037C* Comparator | 753 | 41 | 8.80E+04 | 9.55E−05 | 1.09E−09 | 121 |

*indicates that mAb was captured using anti-mFc immobilized surface

TABLE 6

Binding kinetics parameters of hTrkB.mFc binding to TrkB monoclonal antibodies at 37° C.

| Captured Analyte | Amount of Analyte Captured (RU) | 100 nM hTrkB-mFc Bound (RU) | $k_a$ (1/Ms) | $k_d$ (1/s) | $K_D$ (M) | $t_{1/2}$ (min) |
|---|---|---|---|---|---|---|
| H4H9780P | 56 ± 1 | 14 | 6.65E+04 | 2.22E−04 | 3.33E−09 | 52 |
| H4H9814P | 46 ± 1 | 42 | 2.83E+06 | 2.08E−04 | 7.33E−11 | 56 |
| H4H9816P2 | 71 ± 1.4 | 14 | 6.95E+04 | 2.40E−04 | 3.46E−09 | 48 |
| H1M8037C* Comparator | 814.46 | 58 | 2.35E+05 | 2.92E−04 | 1.24E−09 | 40 |

*indicates that mAb was captured using anti-mFc immobilized surface

TABLE 7

Binding kinetics parameters of mTrkB.mmH binding to TrkB monoclonal antibodies at 25° C.

| Captured Analyte | Amount of Analyte Captured (RU) | 100 nM mTrkB.mmH Bound (RU) | $k_a$ (1/Ms) | $k_d$ (1/s) | $K_D$ (M) | $t_{1/2}$ (min) |
|---|---|---|---|---|---|---|
| H4H9780P | 111 ± 0.7 | −1 | NB | NB | NB | NB |
| H4H9814P | 88 ± 0.7 | −2 | NB | NB | NB | NB |

TABLE 7-continued

Binding kinetics parameters of mTrkB.mmH binding to TrkB monoclonal antibodies at 25° C.

| Captured Analyte | Amount of Analyte Captured (RU) | 100 nM mTrkB.mmH Bound (RU) | $k_a$ (1/Ms) | $k_d$ (1/s) | $K_D$ (M) | $t_{1/2}$ (min) |
|---|---|---|---|---|---|---|
| H4H9816P2 | 135 ± 0.6 | 0 | NB | NB | NB | NB |
| H1M8037C* Comparator | 755 | 26 | 4.12E+04 | 1.68E−03 | 4.08E−08 | 7 |

*indicates that mAb was captured using anti-mFc immobilized surface

TABLE 8

Binding kinetics parameters of mTrkB.mmH binding to TrkB monoclonal antibodies at 37° C.

| Captured Analyte | Amount of Analyte Captured (RU) | 100 nM mTrkBmmH Bound (RU) | $k_a$ (1/Ms) | $k_d$ (1/s) | $K_D$ (M) | $t_{1/2}$ (min) |
|---|---|---|---|---|---|---|
| H4H9780P | 60 ± 0.7 | 1 | NB | NB | NB | NB |
| H4H9814P | 49 ± 0.6 | 0 | NB | NB | NB | NB |
| H4H9816P2 | 75 ± 0.9 | 0 | NB | NB | NB | NB |
| H1M8037C* Comparator | 815.95 | 31 | 7.40E+04 | 6.96E−03 | 9.41E−08 | 1.7 |

*indicates that mAb was captured using anti-mFc immobilized surface

TABLE 9

Binding kinetics parameters of rTrkB.mmH binding to TrkB monoclonal antibodies at 25° C.

| Captured Analyte | Amount of Analyte Captured (RU) | 100 nM rTrkB.mmH Bound (RU) | $k_a$ (1/Ms) | $k_d$ (1/s) | $K_D$ (M) | $t_{1/2}$ (min) |
|---|---|---|---|---|---|---|
| H4H9780P | 108 ± 0.7 | −1 | NB | NB | NB | NB |
| H4H9814P | 86 ± 0.4 | −1 | NB | NB | NB | NB |
| H4H9816P2 | 134 ± 0.3 | 0 | NB | NB | NB | NB |
| H1M8037C* Comparator | 756 | 26 | 5.16E+04 | 1.60E−03 | 3.10E−08 | 7 |

*indicates that mAb was captured using anti-mFc immobilized surface

TABLE 10

Binding kinetics parameters of rTrkB.mmH binding to TrkB monoclonal antibodies at 37° C.

| Captured Analyte | Amount of Analyte Captured (RU) | 100 nM rTrkB.mmH Bound (RU) | $k_a$ (1/Ms) | $k_d$ (1/s) | $K_D$ (M) | $t_{1/2}$ (min) |
|---|---|---|---|---|---|---|
| H4H9780P | 59 ± 0.2 | 0 | NB | NB | NB | NB |
| H4H9814P | 48 ± 0.5 | −1 | NB | NB | NB | NB |
| H4H9816P2 | 74 ± 0.6 | 0 | NB | NB | NB | NB |
| H1M8037C* Comparator | 815.45 | 32 | 7.93E+04 | 6.94E−03 | 8.75E−08 | 1.7 |

*indicates that mAb was captured using anti-mFc immobilized surface

Example 4. Biacore Binding Kinetics of Surrogate Anti-TrkB Monoclonal Antibodies Binding to Different TrkB Reagents Measured at 25° C.

Equilibrium dissociation constants ($K_D$ values) for TrkB binding to purified anti-TrkB monoclonal antibodies were determined using a real-time surface plasmon resonance biosensor using a Biacore T200 instrument. All binding studies were performed in 10 mM Hepes pH 7.4, 150 mM NaCl, 3 mM EDTA, and 0.05% v/v Surfactant Tween-20 (HBS-ET running buffer) at 25° C. The Biacore sensor surface was first derivatized by amine coupling with rabbit anti-mouse Fc polyclonal antibody (GE Healthcare #BR-1008-38) to capture anti-TrkB monoclonal antibodies. Binding studies were performed on the following TrkB reagents; human TrkB extracellular domain expressed with a C-terminal myc-myc-hexahistidine tag (hTrkB.mmH; SEQ ID NO: 76; NP_001018074.1), mouse TrkB extracellular domain expressed with a C-terminal myc-myc-hexahistidine tag (mTRKB.mmH; SEQ ID NO: 79; NP_001020245), and rat TrkB extracellular domain expressed with a C-terminal myc-myc-hexahistidine tag (rTRKB.mmH; SEQ ID NO: 84; XP_002721319.1). Different concentrations of TrkB reagents were first prepared in HBS-ET running buffer (90 nM-3.33 nM; 3-fold serial dilution) and were injected over anti-mouse Fc captured anti-TrkB monoclonal antibody surface for 4 minutes at a flow rate of 50 µL/minute, while the dissociation of monoclonal antibody bound TrkB reagent was monitored for 10 minutes in HBS-ET running buffer. Kinetic association ($k_a$) and dissociation ($k_d$) rate constants were determined by fitting the real-time binding sensorgrams to a 1:1 binding model with mass transport limitation using Scrubber 2.0c curve-fitting software. Binding dissociation equilibrium constants ($K_D$) and dissociative half-lives (t½) were calculated from the kinetic rate constants as:

$$K_D(M) = \frac{kd}{ka}, \text{ and } t1/2(\min) = \frac{\ln(2)}{60 \times kd}$$

Binding kinetic parameters for hTrkB.mmH, mTrkB.mmH or rTrkB.mmH binding to different anti-TrkB monoclonal antibodies of the invention at 25° C. are shown in Tables 11 through 13.

Results:

At 25° C., the surrogate anti-TrkB monoclonal antibodies of the invention show no binding to hTrkB.mmH, as shown in Table 11.

At 25° C., the surrogate anti-TrkB monoclonal antibodies of the invention bound to mTrkB.mmH with KD values ranging from 2.39 nM to 32.4 nM, as shown in Table 12.

At 25° C., the surrogate anti-TrkB monoclonal antibodies of the invention bound to rTrkB.mmH with KD values ranging from 2.56 nM to 26.9 nM, as shown in Table 13.

TABLE 11

Binding kinetics parameters of hTrkB.mmH binding to TrkB monoclonal antibodies at 25° C.

| Captured Analyte | Amount of Analyte Captured (RU) | 90 nM hTrkB.mmH Bound (RU) | $k_a$ (1/Ms) | $k_d$ (1/s) | $K_D$ (M) | $t_{1/2}$ (min) |
|---|---|---|---|---|---|---|
| M2aM14173N | 230 ± 0.8 | 0 | NB | NB | NB | NB |
| M2aM14178N | 125 ± 0.1 | −1 | NB | NB | NB | NB |
| M2aM14179N | 396 ± 2.1 | −2 | NB | NB | NB | NB |

TABLE 12

Binding kinetics parameters of mTrkB.mmH binding to TrkB monoclonal antibodies at 25° C.

| Captured Analyte | Amount of Analyte Captured (RU) | 90 nM mTrkB.mmH Bound (RU) | $k_a$ (1/Ms) | $k_d$ (1/s) | $K_D$ (M) | $t_{1/2}$ (min) |
|---|---|---|---|---|---|---|
| M2aM14173N | 236 ± 1.1 | 33 | 7.41E+04 | 6.30E−04 | 8.49E−09 | 18 |
| M2aM14178N | 126 ± 0.3 | 12 | 1.03E+05 | 2.47E−04 | 2.39E−09 | 47 |
| M2aM14179N | 416 ± 4.3 | 32 | 1.15E+05 | 3.72E−03 | 3.24E−08 | 3.1 |

TABLE 13

Binding kinetics parameters of rTrkB.mmH binding to TrkB monoclonal antibodies at 25° C.

| Captured Analyte | Amount of Analyte Captured (RU) | 90 nM rTrkB.mmH Bound (RU) | $k_a$ (1/Ms) | $k_d$ (1/s) | $K_D$ (M) | $t_{1/2}$ (min) |
|---|---|---|---|---|---|---|
| M2aM14173N | 233 ± 0.7 | 33 | 7.90E+04 | 6.32E−04 | 8.00E−09 | 18 |
| M2aM14178N | 125 ± 0.3 | 11 | 9.00E+04 | 2.30E−04 | 2.56E−09 | 50 |
| M2aM14179N | 404 ± 2.5 | 33 | 1.48E+05 | 3.98E−03 | 2.69E−08 | 2.9 |

Example 5. Bioassay with HEK293/SRE-luc/hTrkB and HEK293/SRE-luc/mTrkB(Ecto)-hTrkB (TM-Cyto) Cells A bioassay was developed to detect the activation of TrkB using a luciferase reporter gene under control of the serum response element (SRE) and the ligand, brain derived neurotrophic factor (BDNF, R & D Systems). HEK293 cell lines were generated that stably express a luciferase reporter (SRE response element-luciferase, SRE-luc, SA Bioscience, #CLS-010L) with either human TrkB (hTrkB, amino acids 32-429 of NP_001018074.1 or Uniprot number Q16620-1) or mouse TrkB extracellular domain fused to the transmembrane and cytoplasmic domains of human TrkB (mTrkB, amino acids 32-429 of NP_001020245.1 or Uniprot number P15200-1 fused to hTrkB, amino acids 431-822). The stable cell lines, HEK293/SRE-Luc/hTrkB and HEK293/SRE-Luc/mTrkB, were maintained in DMEM supplemented with 10% FBS, non-essential amino acids, penicillin/streptomycin/glutamine, 1 □g/mL puromycin, and 500 □g/mL G418.

For the bioassay, cells were seeded into 96-well assay plates at 20,000 cells/well in Opti-MEM™ supplemented with 0.1% FBS, penicillin/streptomycin and L-glutamine, and then incubated at 37° C. in 5% $CO_2$ overnight. The next morning, human BDNF or antibodies was serially diluted from 100 nM to 0.002 nM (plus a sample containing buffer alone without ligand) and added to the cells to determine the activation of TrkB signaling. The serially diluted antibodies were also tested with 100 pM of BDNF (R & D Systems, 248-BD/CF). The cells were then incubated for 5.5 hours at 37° C. in the presence of 5% $CO_2$. Luciferase activity was measured after the addition of OneGlo reagent (Promega) using a Victor X instrument (Perkin Elmer). The results were analyzed using nonlinear regression (4-parameter logistics) with Prism 5 software (GraphPad) to obtain $EC_{50}$ and $IC_{50}$ values. Maximum activation of antibodies was calculated using the following:

$$\text{Max. \% Activation} = \frac{(\text{Maximum } RLU \text{ acheived by antibody}) - (RLU \text{ acheived by no } BDNF)}{(\text{Maximum } RLU \text{ acheived by } BDNF) - (RLU \text{ acheived by no } BDNF)}$$

Results Summary and Conclusions:

As shown in Table 14, three anti-TrkB antibodies of the invention H4H9816P2, H4H9814P, H4H9780P showed activation of human TrkB signaling in HEK293/SRE-luc/hTrkB cells in the absence of BDNF with $EC_{50s}$ of 35-82 pM with maximum activation ranging 88-92%. Three antibodies of the invention were also tested in the presence 100 pM BDNF. Whereas 100 pM BDNF showed activation of 56% in the presence of irrelevant control mAb, Control mAb2, the antibodies of the invention showed further activation with $EC_{50s}$ of 45-76 pM with maximum activation ranging 77-80%. Three anti-TrkB antibodies of the invention did not show activation of mouse TrkB signaling in HEK293/SRE-luc/mTrkB cells in the absence of BDNF or presence of 100 pM BDNF. Control mAb 1, an anti-TrkB comparator antibody H1M8037C, showed activation of human TrkB signaling with an $EC_{50}$ of 76 pM with maximum activation of 78% and mouse TrkB with an $EC_{50}$ of 43 pM with maximum activation of 85% without BDNF. In the presence of 100 pM BDNF, Control mAb 1 activated human TrkB signaling with an $EC_{50}$ of 110 pM with maximum activation of 79% and mouse TrkB with an $EC_{50}$ of 42 pM with maximum activation of 69%, greater than the activation by Control mAb 2 with 100 pM BDNF. Control mAb 2, an irrelevant human IgG4 antibody, did not show any activation in the absence or in the presence of 100 pM BDNF.

As shown in Table 15, three anti-TrkB antibodies of the invention M2aM14173N, M2aM14178N, M2aM14179N showed activation of mouse TrkB signaling in HEK293/SRE-luc/mTrkB cells in the absence of BDNF with $EC_{50s}$ of 34-190 pM with maximum activation ranging from 76-94%. Three antibodies of the invention were also tested in the presence 100 pM BDNF. Whereas 100 pM BDNF showed activation of 60% in the presence of irrelevant isotype control mAb, Control mAb4, the antibodies of the invention showed further activation with $EC_{50s}$ of 17-100 pM with maximum activation ranging 67-75%. Three anti-TrkB antibodies of the invention did not show activation of human TrkB signaling in HEK293/SRE-luc/hTrkB cells in the absence of BDNF or presence of 100 pM BDNF. Control mAb 1 showed activation of human TrkB signaling with an $EC_{50}$ of 57 pM with maximum activation of 80% and mouse TrkB with an $EC_{50}$ of 43 pM with maximum activation of 85% without BDNF. In the presence of 100 pM BDNF, Control mAb 1 activated human TrkB signaling with an $EC_{50}$ of 110 pM with maximum activation of 79% and mouse TrkB with an $EC_{50}$ of 42 pM with maximum activation of 69%, greater than the activation by Control mAb 4 with 100 pM BDNF. Control mAb 3 and Control mAb 4, irrelevant mouse IgG2a isotype control antibodies, did not show any activation in the absence or in the presence of 100 pM BDNF.

Tabulated Data Summary:

TABLE 14

Activation of HEK293/SRE-Luc/hTrkB and HEK293/SRE-Luc/mTrkB cells by anti-TrkB antibodies

| | Cells | | | | | | | |
|---|---|---|---|---|---|---|---|---|
| | HEK293/SRE-luc/hTrkB | | | | HEK293/SRE-luc/mTrkB | | | |
| | BDNF | | | | | | | |
| | 1.0E−10 | | | | 7.4E−11 | | | |
| | Ligand | | | | | | | |
| | No BDNF | | 100 pM BDNF | | No BDNF | | 100 pM BDNF | |
| Antibody | EC50 (M) | Activation (%) | EC50 (M) | Activation (%) | EC50 (M) | Activation (%) | EC50 (M) | Activation (%) |
| H4H9780P | 8.2E−11 | 88 | 7.6E−11 | 77 | No activation | 0 | No activation | 55 |
| H4H9814P | 3.5E−11 | 92 | 4.9E−11 | 80 | No activation | 0 | No activation | 54 |

TABLE 14-continued

Activation of HEK293/SRE-Luc/hTrkB and HEK293/SRE-Luc/mTrkB cells by anti-TrkB antibodies

| | Cells | | | | | | | |
|---|---|---|---|---|---|---|---|---|
| | HEK293/SRE-luc/hTrkB | | | | HEK293/SRE-luc/mTrkB | | | |
| | BDNF | | | | | | | |
| | 1.0E−10 | | | | 7.4E−11 | | | |
| | Ligand | | | | | | | |
| | No BDNF | | 100 pM BDNF | | No BDNF | | 100 pM BDNF | |
| Antibody | EC50 (M) | Activation (%) | EC50 (M) | Activation (%) | EC50 (M) | Activation (%) | EC50 (M) | Activation (%) |
| H4H9816P2 | 6.3E−11 | 90 | 4.5E−11 | 78 | No activation | 0 | No activation | 58 |
| Control mAb 1 (Comparator H1M8037C) | 7.6E−11 | 78 | 1.1E−10 | 79 | 4.3E−11 | 85 | 4.2E−11 | 69 |
| Negative Isotype Control mAb 2 | No activation | 3 | No activation | 56 | No activation | 0 | No activation | 54 |

TABLE 15

Activation of HEK293/SRE-Luc/hTrkB and HEK293/SRE-Luc/mTrkB cells by anti-TrkB antibodies (surrogate)

| | Cells | | | | | | | |
|---|---|---|---|---|---|---|---|---|
| | HEK293/SRE-luc/hTrkB | | | | HEK293/SRE-luc/mTrkB | | | |
| | BDNF | | | | | | | |
| | 1.3E−10 | | 1.0E−10 | | 7.4E−11 | | 1.1E−10 | |
| | Ligand | | | | | | | |
| | No BDNF | | 100 pM BDNF | | No BDNF | | 100 pM BDNF | |
| Antibody | EC50 (M) | Activation (%) | EC50 (M) | Activation (%) | EC50 (M) | Activation (%) | EC50 (M) | Activation (%) |
| M2aM14173N | No activation | 2 | No activation | 59 | 3.6E−11 | 94 | 1.7E−11 | 74 |
| M2aM14178N | No activation | 0 | No activation | 52 | 1.9E−10 | 76 | 1.0E−10 | 67 |
| M2aM14179N | No activation | 4 | No activation | 52 | 3.4E−11 | 87 | 2.1E−11 | 75 |
| Control mAb 1 (Comparator H1M8037C) | 5.7E−11 | 80 | 1.1E−10 | 79 | 4.3E−11 | 85 | 4.2E−11 | 69 |
| Negative Isotype Control mAb 3 | No activation | 0 | Not tested | Not tested | Not tested | Not tested | Not tested | Not tested |
| Negative Isotype Control mAb 4 | Not tested | Not tested | No activation | 61 | No activation | 0 | No activation | 60 |

Example 6. In Vivo Comparison of the Effect of TrkB Agonist Antibody H4H9816P2 and IgG4 Isotype Control REGN1945 on TrkB Phosphorylation in the Brain Following Stereotaxic Injection in TrkB$^{hu/hu}$ Mice In order to determine the effect of a TrkB agonist antibody of the invention, H4H9816P2, on TrkB activation kinetics, a time-course study of TrkB phosphorylation following direct hippocampal injection was performed in mice homozygous for human TrkB receptor in place of mouse TrkB receptor (referred to as TrkB$^{hu/hu}$ mice). TrkB$^{hu/hu}$ mice (N=48) received bilateral stereotaxic injections with either 2 μl of vehicle (PBS), REGN1945 hereby noted as IgG4 isotype control antibody (27.5 mg/mL final concentration), or TrkB agonist antibody H4H9816P2 (27.5 mg/mL final concentration) into the hippocampus, −2 mm posterior and +1.5 mm lateral to bregma. In order to minimize tissue damage, injection and needle removal were both performed gradually over 5-minute intervals. TrkB$^{hu/hu}$ mice were then sacrificed by CO$_2$ euthanasia approximately 30 minutes, 1 hour, 4 hours, or 18 hours post-injection. A terminal bleed was performed via cardiac puncture to collect blood, and mice were then transcardially perfused with cold heparinized saline. The brain was carefully removed from the skull, and a 2 mm³ section of tissue surrounding the injection site was dissected, collected in an Eppendorf tube and stored on ice. The brain section was then lysed in 300 uL of RIPA lysis buffer (ThermoFisher Scientific, Cat #89901) containing 2× protease and phosphatase inhibitors (ThermoFisher Scientific, Cat #78444) and stored on ice. The lysed tissue was then homogenized for further processing, aliquoted and stored at −80° C.

To assess TrkB phosphorylation in the brain tissue, immuno-precipitation and western blotting was performed. Anti-human TrkB antibody H4H10108N that does not compete for binding with H4H9816P2 was coupled to NHS-activated Sepharose beads (prepared using manufacturer's protocol; GE Healthcare, Cat #17-0906) and washed with DPBS three times to remove any residual preservation solution. Homogenized brain lysates were thawed on ice and diluted to a concentration of 1 mg/mL (brain weight to buffer volume) in a buffer composed of 1% NP-40, 0.1% Tween-20, protease and phosphatase inhibitors in TBST. The protein concentration of the homogenized brain lysate was quantified by performing a standard BCA assay per manufacturer's instructions (Thermo Scientific Pierce, Cat #23225). For every 100 ug of protein, 15 uL of anti-human TrkB antibody (H4H10108N) NHS-activated Sepharose beads were added to the brain lysate solution and the mixture was incubated overnight at 4° C. with gentle shaking at 20 rpm (Thermo rotator). The next day, samples were centrifuged at 1000×g for one minute, and the supernatant was then carefully removed. Beads were subsequently washed twice with 400 uL of Tris-buffered saline (Bio-Rad, Cat #1706435) with 1% Tween-20 (Sigma Aldrich, Cat #P9416) (TBST). After carefully aspirating the wash buffer, 60 uL of 0.1% Trifluoroacetic acid (TFA; Sigma-Aldrich, T62200) in water at pH 3.0 was added to each sample. The solution was mixed and allowed to stand for two minutes before being collected and transferred into a separate tube. This process was repeated with another 60 uL of 0.1% TFA at pH 3.0. The two 0.1% TFA solutions for each sample were then combined, and 2 uL of 1M Tris-HCl (ThermoFisher Scientific, Cat #15567-027), at pH 8.5, was added.

The solution was dried using a speed vacuum and then re-suspended and reduced with a mixtue of 20 uL of 1× Laemmli Buffer (Bio-Rad, Cat #1610737) plus 355 nM 2-mercaptoethanol (BME; Gibco, Cat #21985-023). Samples were boiled at 95° C. for 10 minutes and loaded onto a 10-well, Mini-Protean 4-15% Tris-Glycine gel (Bio-Rad, Cat #4561086). After electrophoresis, protein samples were transferred from the Tris-Glycine gel onto a PVDF membrane (Bio-Rad, Cat #170-4156) via the Trans-Blot Turbo Transfer System (Bio-Rad, Cat #1704156) over the course of 30 minutes at a constant rate of 1.3 A and 25 V. After the transfer, the membrane was blocked with 2.5% milk (Bio-Rad, Cat #170-6406) in TBST for one hour at room temperature, and subsequently probed overnight with either an anti-phospho-TrkB antibody (Novus, Cat #NB100-92656) diluted 1:1000 in a solution of 2.5% BSA or anti-TrkB primary antibody (Cell Signaling, Cat #4603) diluted to 1:1000 in 2.5% milk TBST at 4° C. on a shaker at 30 rpm. The next day, blots were washed with TBST and incubated with an anti-rabbit IgG antibody conjugated with horseradish peroxidase (Jackson, Cat #111-035-144) at 1:1000 in 1% milk in TBST for 1 hour at room temperature. Blots were then washed again, developed with ECL solution (PerkinElmer, Inc. Cat #RPN2106), and subsequent image exposures were taken every 30 seconds.

Results Summary and Conclusions:

Immunoprecipitation and subsequent western blotting of protein derived from TrkB$^{hu/hu}$ mouse brain lysates demonstrated that hippocampal TrkB phosphorylation was detectable in mice injected with a TrkB agonist antibody, H4H9816P2, but not in mice treated with vehicle or isotype control antibody, as shown FIG. 1. Amongst the timepoints assessed, TrkB phosphorylation peaked at 4 hours after stereotaxic injection in mice dosed with H4H9816P2. TrkB phosphorylation was also detected by western blot at 18 hours post-dosing in some, but not all mice. Conversely, injection of vehicle and IgG4 isotype control antibody did not induce TrkB phosphorylation at any timepoint. Western blotting also indicated that the total TrkB receptor levels were downregulated in some, but not all TrkB$^{hu/hu}$ mice dosed with H4H9816P2 relative to vehicle and isotype control treated mice. Total TrkB levels appeared to be slightly downregulated in H4H9816P2-treated subjects at 18 hours post-dosing. Thus, these results indicate that direct injection of the TrkB agonist antibody, H4H9816P2, induces phosphorylation of hippocampal TrkB receptors in TrkB$^{hu/hu}$ mice.

Example 7. In Vivo Comparison of the Effect of H4H9816 and Isotype Control REGN1945 Antibodies on Body Weight and Metabolism in TrkB$^{hu/hu}$ Mice To determine the effect of a TrkB agonist antibody of the invention, H4H9816P2, on body weight and composition, a metabolic study of mice homozygous for the expression of human TrkB receptor in place of the mouse TrkB receptor (TrkB$^{hu/hu}$ mice) was conducted following a single subcutaneous antibody injection. TrkB$^{hu/hu}$ mice (male, 20 weeks old) were first transferred from group-cage to single-cage housing for two weeks of acclimatization. After this period, mice were transferred to metabolic cages (CLAMS, Columbus Instruments) to assess changes in food and water consumption, locomotion, energy expenditure and respiration following antibody administration. Regular powdered chow was stored in a floor chamber on a spring-loaded scale (Mettler Toledo, PL602E) to measure food consumption via changes in total chow weight. Water was accessible via a cage-top spout and intake was measured by tracking changes in pump-line volume (Oxymax®/CLAMS Liquid Unit). CLAMS metabolic cages measured each of these parameters in continuous, 16-18 minute intervals throughout the duration of the study. Metabolic data was analyzed in single measures and summarized in 24-hour intervals containing one complete dark and light cycle using OXYMAX®/CLAMS software (Columbus instruments, v5.35). After acclimating to the cages for two weeks, TrkB$^{hu/hu}$ mice received a single 50 mg/kg subcutaneous dose of either a TrkB agonist antibody, H4H9816P2, or an IgG4 isotype control antibody in PBS at pH7.2. A group of naïve control TrkB$^{hu/hu}$ mice did not receive an injection. Mice were weighed immediately prior to dosing, and at 24, 48, 72, 96, and 120 hours post-dosing. In order to measure each mouse's body composition, Nuclear Magnetic Resonance Relaxometry, also referred to as Quantitative Magnetic Resonance, was performed using a EchoMRI™-500 Analyzer (EchoMRI LLC). Prior to dosing, mice were placed in a clear plastic holder and inserted into the NMR-MRI device to measure each subject's lean mass, fat mass, and hydration status. Measurements were performed over the course of 0.5-3.2 minutes per mouse, and were taken again approximately 120 hours after dosing.

Results Summary and Conclusions:

Daily body weight monitoring was performed to determine whether a single subcutaneous injection of H4H9816P2 induces weight loss in TrkB$^{hu/hu}$ mice. Prior to dosing, there were no significant differences in the average body weight of the three treatment groups, as each had an average pre-dose body weight of 28.39-29.85 g (Table 16). At 48 hours post-dosing, however, H4H9816P2-treated TrkB$^{hu/hu}$ mice lost an average of 1.70 g, or 5.96% of their pre-dose body weight. At the same time point, naïve and isotype control antibody-treated TrkB$^{hu/hu}$ mice gained between 1.79-2.37% of their pre-dose body weight. H4H9816P2-treated TrkB$^{hu/hu}$ mice continued to lose weight throughout the full time course of the study, and by 72 and 96 hours post-dosing these mice had lost an average of 8.42% and 11.80% of their pre-dose body weight, respectively. At 120 hours post-dosing, H4H9816P2-treated TrkB$^{hu/hu}$ mice had lost an average of 12.67% of their pre-dose body weight. Conversely, naïve and isotype control-treated TrkB$^{hu/hu}$ mice did not exhibit any loss in pre-dose body weight throughout the study. As body weight in H4H9816P2-treated TrkB$^{hu/hu}$ mice was significantly reduced relative to both naïve and isotype controls at 48, 72, 96, and 120 hours post-dosing, it was determined that TrkB agonist antibody H4H9816P2 induced significant body weight loss in TrkB$^{hu/hu}$ mice.

TABLE 16

Body weight of TrkB$^{hu/hu}$ mice after dosing with TrkB agonist antibody H4H9816P2

| Experimental group | Mean pre-dose body weight (g) (±SD) / Percent change from pre-dose body weight (+/−SD) | Mean body weight (g) 24 hours post-dose (±SD) / Percent change from pre-dose body weight (+/−SD) | Mean body weight (g) 48 hours post-dose (±SD) / Percent change from pre-dose body weight (+/−SD) | Mean body weight (g) 72 hours post-dose (±SD) / Percent change from pre-dose body weight (+/−SD) | Mean body weight (g) 96 hours post-dose (±SD) / Percent change from pre-dose body weight (+/−SD) | Mean body weight (g) 120 hours post-dose (±SD) / Percent change from pre-dose body weight (+/−SD) |
|---|---|---|---|---|---|---|
| Naive (n = 3) | 28.85 (+/−0.81) N/A | 29.69 (+/−0.97) +2.91% (+/−0.62) | 29.36 (+/−1.10) +1.79% (+/−1.62) | 29.32 (+/−1.29) +1.65% (+/−2.24) | 29.29 (+/−1.10) +1.54% (+/−1.22) | 28.88 (+/−1.04) +0.10% (+/−1.05) |
| Isotype control (n = 4) | 29.21 (+/−2.68) N/A | 30.27 (+/−2.51) +3.61% (+/−1.68) | 29.90 (+/−2.63) +2.37% (+/−1.50) | 30.08 (+/−2.69) +2.98% (+/−1.09) | 29.87 (+/−2.52) +2.25% (+/−1.56) | 29.69 (+/−2.68) +1.65% (+/−0.81) |
| H4H9816P2 (n = 4) | 28.39 (+/−1.35) N/A | 27.87 (+/−1.29) −1.83% (+/−0.56) | 26.69 (+/−0.87) −5.96% (+/−1.88) | 26.00* (+/−0.98) −8.42% (+/−1.85) | 25.04** (+/−1.03) −11.80% (+/−1.52) | 24.79** (+/−1.36) −12.67% (+/−1.66) |

Note:

Statistical significance determined by two-way ANOVA with Tukey's multiple comparison post-hoc test is indicated (*= p < 0.05,

**= p < 0.01,

*** = p < 0.001,

**** = p < 0.0001, compared to isotype control group: TrkB$^{hu/hu}$ mice dosed with 50 mg/kg isotype control antibody.

The effect of TrkB agonist antibody H4H9816P2 injection on body composition was also measured by performing NMR-MRI on each subject before and after dosing. Prior to dosing, the three treatment groups of TrkB$^{hu/hu}$ mice did not exhibit any significant differences in fat mass or lean mass, as each group had an average of 4.19-4.75 g of fat mass and 21.32-21.70 g of lean mass (Table 17). Following antibody administration, however, TrkB$^{hu/hu}$ mice dosed with H4H9816P2 lost an average of 48.90% of their total body fat mass over the course of the study (Table 17). Naïve and isotype control antibody-treated TrkB$^{hu/hu}$ mice lost an average of 8.49% and 9.48% of their pre-dose fat mass, respectively, which was significantly less than H4H9816P2-treated subjects (Table 17). Furthermore, H4H9816P2-treated TrkB$^{hu/hu}$ mice lost an average of 7.84% of their lean mass throughout the study, which was significantly greater than the 2.41% and 1.75% of average pre-dose lean mass lost by naïve and isotype control antibody-treated groups, respectively (Table 17). As such, the described body weight loss could be explained by a significant loss of fat mass and a modest loss of lean mass following injection of TrkB agonist antibody H4H9816P2 in TrkB$^{hu/hu}$ mice.

TABLE 17

Body composition of TrkB$^{hu/hu}$ mice after dosing with TrkB agonist antibody H4H9816P2

| Experimental group | Mean pre-dose fat mass (%) (±SD) | Mean fat mass (%) 120 hours post-dose (±SD) | Mean fat mass change (%) 120 hours post-dose (±SD) | Mean pre-dose lean mass (%) (±SD) | Mean lean mass (%) 120 hours post-dose (±SD) | Mean lean mass change (%) 120 hours post-dose (±SD) |
|---|---|---|---|---|---|---|
| Naive (n = 3) | 4.65 (+/−0.32) | 4.27 (+/−0.55) | −8.49 (+/−7.18) | 21.45 (+/−0.79) | 20.94 (+/−0.98) | −2.41 (+/−1.81) |
| Isotype control (n = 4) | 4.75 (+/−2.98) | 4.40 (+/−2.98) | −9.48 (+/−6.00) | 21.70 (+/−0.50) | 21.32 (+/−0.35) | −1.75 (+/−0.98) |
| H4H9816P2 (n = 4) | 4.19 (+/−1.15) | 2.14 (+/−0.64) | −48.90**** (+/−5.06) | 21.32 (+/−1.87) | 19.64 (+/−1.69) | −7.84*** (+/−0.94) |

Note:

Statistical significance determined by Kruskal-Wallis One-way ANOVA with Tukey's multiple comparison post-hoc test is indicated (* = p < 0.05,

** = p < 0.01,

*** = p < 0.001,

**** = p < 0.0001, compared to isotype control group: TrkB$^{hu/hu}$ mice dosed with 50 mg/kg isotype control antibody.

In addition to assessing the effects of TrkB agonist antibody H4H9816P2 injection on body weight and composition in TrkB$^{hu/hu}$ mice, feeding, drinking, and locomotor activity were continuously measured by metabolic cages. Prior to dosing, TrkB$^{hu/hu}$ mice consumed an average of 3.49-3.73 g of chow per day. Within 24 hours of dosing, however, H4H9816P2-treated TrkB$^{hu/hu}$ mice significantly reduced their food intake to 2.20 g of chow per day. The average level of food intake in H4H9816P2-treated TrkB$^{hu/hu}$ mice did not exceed 2.49 g of chow per day throughout the remainder of the study, while naïve and isotype antibody-treated TrkB$^{hu/hu}$ mice consistently consumed an average of 3.62-4.07 g of chow per day (Table 18).

Similarly, there were no significant differences in daily water consumption between treatment groups prior to dosing. TrkB$^{hu/hu}$ mice consumed an average of 4.67-5.55 mL of water per day in each treatment group (Table 19). After dosing, H4H9816P2-treated TrkB$^{hu/hu}$ mice reduced their water intake to 2.05-3.24 mL of water per day. This was significantly lower than naïve and isotype control antibody-treated TrkB$^{hu/hu}$ mice, which consistently consumed 4.50-5.77 mL of water per day throughout the study (Table 19). Thus, injection of the TrkB agonist antibody, H4H9816P2, appeared to result in a significant reduction of both food and water intake in TrkB$^{hu/hu}$ mice relative to both naïve and isotype controls.

TABLE 18

Food consumption of TrkB$^{hu/hu}$ mice after dosing with TrkB agonist antibody H4H9816P2

| Experimental group | Mean total food intake (g) 0-24 hours pre-dose (±SD) | Mean total food intake (g) 0-24 hours post-dose (±SD) | Mean total food intake (g) 24-48 hours post-dose (±SD) | Mean total food intake (g) 48-72 hours post-dose (±SD) | Mean total food intake (g) 72-96 hours post-dose (±SD) |
|---|---|---|---|---|---|
| Naive (n = 3) | 3.51 (+/−0.53) | 3.98 (+/−0.08) | 3.76 (+/−0.19) | 3.62 (+/−0.35) | 3.91 (+/−0.18) |
| Isotype control (n = 4) | 3.73 (+/−0.48) | 4.07 (+/−0.23) | 3.99 (+/−0.17) | 3.89 (+/−0.22) | 3.80 (+/−0.22) |
| H4H9816P2 (n = 4) | 3.49 (+/−1.07) | 2.20**** (+/−0.16) | 2.08**** (+/−0.36) | 2.18**** (+/−0.37) | 2.49*** (+/−0.47) |

Note:
Statistical significance determined by Kruskal-Wallis One-way ANOVA with Tukey's multiple comparison post-hoc test is indicated
(* = p < 0.05,
** = p < 0.01,
*** = p < 0.001,
**** = p < 0.0001, compared to isotype control group: TrkB$^{hu/hu}$ mice dosed with 50 mg/kg isotype control antibody.

TABLE 19

Water consumption of TrkB$^{hu/hu}$ mice after dosing with TrkB agonist antibody H4H9816P2

| Experimental group | Mean total water intake (mL) 0-24 hours pre-dose (±SD) | Mean total water intake (mL) 0-24 hours post-dose (±SD) | Mean total water intake (mL) 24-48 hours post-dose (±SD) | Mean total water intake (mL) 48-72 hours post-dose (±SD) | Mean total water intake (mL) 72-96 hours post-dose (±SD) |
|---|---|---|---|---|---|
| Naive (n = 3) | 4.79 (+/−0.21) | 5.42 (+/−0.94) | 4.96 (+/−0.91) | 4.57 (+/−0.56) | 4.88 (+/−0.32) |
| Isotype control (n = 4) | 5.55 (+/−1.23) | 4.50 (+/−1.08) | 5.08 (+/−1.39) | 5.09 (+/−1.10) | 5.77 (+/−1.62) |
| H4H9816P2 (n = 4) | 4.67 (+/−1.13) | 2.25** (+/−0.55) | 3.24* (+/−1.10) | 2.05*** (+/−0.29) | 2.25**** (+/−0.24) |

Note:
Statistical significance determined by Kruskal-Wallis One-way ANOVA with Tukey's multiple comparison post-hoc test is indicated
(* = p < 0.05,
** = p < 0.01,
*** = p < 0.001,
**** = p < 0.0001, compared to isotype control group: TrkB$^{hu/hu}$ mice dosed with 50 mg/kg isotype control antibody.

To determine the effects of antibody treatment on activity, locomotion was analyzed by OXYMAX®/CLAMS software (Columbus instruments, v5.35), which continuously measured the total number of x-plane ambulations of each mouse. One mouse exhibited hyperactivity prior to dosing and was removed from post-dose statistical analysis. While naïve and isotype antibody-treated subjects consistently registered an average of 11,000-15,000 ambulations per day throughout the study, H4H9816P2-treated TrkB$^{hu/hu}$ registered 28,260 ambulations between 24-48 hours post-dosing, and registered 21,193 and 27,028 ambulations from 48-72 and 72-96 hours post-dosing, respectively (Table 20). H4H9816P2-treated TrkB$^{hu/hu}$ mice registered more total ambulation counts at each time point following antibody administration, suggesting hyperactivity to be an additional effect of H4H9816P2 injection. In combination, these effects suggest that a single subcutaneous injection of the TrkB agonist antibody, H4H9816P2, induced significant changes in body weight, body composition, metabolism, and locomotion in TrkB$^{hu/hu}$ mice.

TABLE 20

Locomotion of TrkB$^{hu/hu}$ mice after dosing with TrkB agonist antibody H4H9816P2

| Experimental group | Mean total ambulations (counts) 0-24 hours pre-dose (±SD) | Mean total ambulations (counts) 0-24 hours post-dose (±SD) | Mean total ambulations (counts) 24-48 hours post-dose (±SD) | Mean total ambulations (counts) 48-72 hours post-dose (±SD) | Mean total ambulations (counts) 72-96 hours post-dose (±SD) |
|---|---|---|---|---|---|
| Naive (n = 3) | 16562 (+/−3380) | 14692 (+/−2792) | 14387 (+/−6126) | 13279 (+/−3607) | 12525 (+/−4121) |
| Isotype Control (REGN1945) (n = 4) | 18105 (+/−4085) | 13380 (+/−2730) | 13049 (+/−3376) | 11371 (+/−2552) | 11468 (+/−2088) |
| H4H9816P2 (n = 4) | 13292 (+/−5294) | 16575 (+/−6836) | 28260 (+/−19874) | 21193 (+/−6668) | 27028* (+/−10969) |

Note:
Statistical significance determined by Kruskal-Wallis One-way ANOVA with Tukey's multiple comparison post-hoc test is indicated
(*= $p < 0.05$,
**= $p < 0.01$,
***= $p < 0.001$,
****= $p < 0.0001$, compared to isotype control group: TrkB$^{hu/hu}$ mice dosed with 50 mg/kg isotype control antibody.

Example 8. Optic Nerve Transection Model to Determine the Effect of Anti-TrkB Antibody on Retinal Ganglion Cell (RGC) Survival All procedures were conducted in accordance with the ARVO Statement for Use of Animals in Ophthalmic and Vision Research and the Regeneron Pharmaceutical Inc. IACUC. Adult female TrkB humanized rats (Velocigene, Regeneron Pharmaceutical Inc.), 8-10 weeks old, each weighing 200-250 g, were used. All surgical procedures on rats were performed under general anesthesia using an intraperitoneal injection of ketamine (63 mg/kg) and xylazine (6.0 mg/kg). Eye ointment containing erythromycin (0.5%, Bausch & Lomb) was applied to protect the cornea.

Intraorbital Optic Nerve Axotomy and Intravitreal Injection

The left optic nerve (ON) was exposed intraorbitally, its dura was opened. ON was transected about 1.5 mm behind the globe. Care was taken to avoid damaging the blood supply to the retina. Intravitreal injections were performed just posterior to the pars plana with a pulled glass pipette connected to a 50 µl Hamilton syringe. Care was taken not to damage the lens. Rats with any significant postoperative complications (e.g., retinal ischemia, cataract) were excluded from further analysis. Animals were allocated to different experimental groups. One control group received intravitreal injections of 3 µl isotype control REGN1945 (46.6 µg/µl); the other group received injection of 3 µl anti-human TrkB antibody H4H9816P2 (45.7 µg/µl) at 3 and 10 days after ON axotomy.

In another experiment, a dose-response of anti-human TrkB antibody H4H9816P2 was tested. 1-9 months old homozygous TrkB humanized rats received intravitreal injection of 3u1 anti-human TrkB antibody H4H9816P2 (0.01, 0.1, 1 or 10 ug/ul) or isotype control REGN1945 (10 µg/µl) at 3 and 10 days after ON axotomy.

Immunohistochemical Staining and Counting of Viable RGCs

Brn3a (brain-specific homeobox/POU domain protein 3A) was used as a marker for surviving retinal ganglion cells (RGCs), because it has been shown to be an efficient and reliable method for selective labelling of viable RGCs in retinal whole mounts after ON injury (Nadal-Nicolas F M, Jiménez-López M, Sobrado-Calvo P, Nieto-López L, Cánovas-Martínez I, Salinas-Navarro M, Vidal-Sanz M, Agudo M., Invest Ophthalmol Vis Sci. 2009 August; 50(8):3860-8). To immunostain for Brn3a, retinas were blocked in 10% normal donkey serum and 0.5% Triton X-100 for 1 hr, then incubated in the same medium with Brn3a antibody (1:400; Cat #: sc-31984, Santa Cruz) 2 hr at room temperature. After further washes retinas were incubated with Alexa594-conjugated donkey anti-goat secondary antibody (1:400; Cat #: A-11058, Invitrogen) overnight at 4° C.

Results Summary and Conclusions:

To assess the effect of TrkB agonist antibody on RGC survival in vivo, we used a complete optic nerve transection model. TrkB agonist antibody (H4H9816P2) or isotype (negative control) antibody was applied at 3 and 10 days after surgery. Animals were euthanized 14 days after axotomy. The RGC density in the uninjured contralateral eye is similar in the three TrkB genotypes, average around 1600 per mm$^2$ as shown in Table 21. The density of surviving RGCs was assessed in retinal whole mounts using Brn3a staining. It was observed that in homozygous TrkB humanized rat, TrkB agonist antibody (H4H9816P2) significantly ($p<0.01$, Mann-Whitney test) increased RGC survival compared with controls (685±106 vs. 255±66 RGCs per mm$^2$). In the heterozygous TrkB humanized rat, there is also significant ($p<0.05$, Mann-Whitney test) survival effect of TrkB agonist antibody (444±90 vs. 208±50 RGCs per mm$^2$). In the wild type TrkB rat, there is slight but not significant increase of RGC number in TrkB agonist antibody compared to isotype control (Table 22). In the dose-response experiment, the RGC density was quantified in retinal whole mounts using Brn3a staining 14 days after axotomy. There are clear dose-response of TrkB agonist antibody. Compared to the antibody control group (168±43 RGCs per mm$^2$), TrkB agonist antibody (H4H9816P2) significantly ($p<0.01$, one-way ANOVA with Tukey post test) increased RGC survival in 3 ug (564+/−124 RGCs per mm$^2$) or 30 ug (543+/−242 RGCs per mm$^2$) per injection group. There is no difference between 3 and 30 ug groups. In groups that received 0.03 ug (202+/−96 RGCs per mm$^2$) or 0.3 ug (337+/−210 RGCs per mm$^2$) per injection group, there is only a trend but not significant increase in RGC survival (Table 23). In conclusion, the TrkB agonist antibody H4H9816P2 showed significantly increased RGC survival in TrkB$^{hu/hu}$ and TrkB$^{hu/+}$ rats.

Conclusion:

TrkB agonist Ab (H4H9816P2) dose dependently significantly increased RGC survival in a humanized TrkB rat.

TABLE 21

RGC quantification (RGCs/mm$^2$) in uninjured control eye TRKB genotypes

| hu/hu | hu/+ | +/+ |
|---|---|---|
| 1637.3 | 1720.4 | 1636.3 |
| 1551.5 | 2064.6 | 1670.2 |
| 1651.4 | 1738.8 | 1873.4 |
| 1628.2 | 2029.8 | 1725.4 |
| 1804.7 | 1929.6 | 1973.4 |
| 1741.3 | 1645.9 | |
| 1739.7 | 1761.5 | |
| 1698.8 | 1787.5 | |
| 1862.5 | 1914.0 | |
| 1779.4 | | |

TABLE 22

RGC quantification (RGCs/mm$^2$) after optic nerve injury

| | H4H9816P2 | | | | | Isotype control Ab | | | | |
|---|---|---|---|---|---|---|---|---|---|---|
| | A:Y1 | A:Y2 | A:Y3 | A:Y4 | A:Y5 | B:Y1 | B:Y2 | B:Y3 | B:Y4 | B:Y5 |
| Hu/Hu | 790.1 | 737.1 | 756.3 | 587.8 | 555.7 | 322.8 | 295.0 | 286.9 | 171.3 | 197.9 |
| Hu/+ | 530.4 | 457.5 | 522.9 | 390.6 | 319.2 | 231.0 | 184.6 | 265.1 | 151.3 | |
| +/+ | 320.9 | 355.5 | 256.9 | 342.7 | | 112.3 | | | | |

TABLE 23

RGC quantification (RGCs/mm²) in dose-response study

| Control Ab | H4H9816P2 | | | |
|---|---|---|---|---|
| 30 ug/ivt | 0.03 ug/ivt | 0.3 ug/ivt | 3 ug/ivt | 30 ug/ivt |
| 222.3 | 162.7 | 341.7 | 637.9 | 493.0 |
| 205.9 | 190.2 | 269.1 | 686.4 | 613.5 |
| 131.7 | 127.7 | 292.2 | 533.2 | 557.6 |
| 136.3 | 174.0 | 252.8 | 574.7 | 227.1 |
| 144.3 | 163.8 | 128.3 | 334.4 | 954.3 |
|  | 392.6 | 740.9 | 620.6 | 411.3 |

Example 9. Effect of Anti-TrkB Antibodies on the Akt and Erk Signaling Pathways All procedures were conducted in accordance with the ARVO Statement for Use of Animals in Ophthalmic and Vision Research and the Regeneron Pharmaceutical Inc. IACUC. Primary mouse cortical neurons were isolated and cultured from humanized TrkB mice (MAID 7139) (Nat Protoc. 2012 September; 7(9):1741-54. doi: 10.1038/nprot.2012.099). A Western Blot (WB) was performed to determine the effects of TrkB agonist Ab on the downstream pathways of Akt and Erk (p-Akt, p-Erk1/2). Primary cortical neuron from postnatal day 1 (P1) humanized TrkB mouse pups were cultured for 4 days (DIV-4) in NeuralQ Basal Medium (Global Stem, cat. #GSM-9420) supplemented with GS21 Neural Supplement (Global Stem, cat. #GSM-3100). Glutamax (Invitrogen, cat. #35050-061) and Penicilin/Streptomycin. Cells were treated with TrkB agonist Abs: H4H9816P-L1 (10 ug/ml), H4H9780P-L1 (10 ug/ml), H4H9814P-L1 (10 ug/ml), IgG4 isotype control REGN1945 (10 ug/ml), control antibody H1M8037C-L1 (10 ug/ml), BDNF (1 ug/ml), for 15 minutes or 2 hours. Western Blot was performed to determine if the agonists have a difference in downstream signaling maintenance and strength. Treated cells were rinsed and scraped in cold PBS containing 1% protease and phosphatase inhibitors (Sigma). Protein concentration was determined by Bradford protein assay (Pierce). Samples (50 μg) were separated by SDS-PAGE in 3-8% Tris-Acetate reduced gels (Novex) and transferred to a nitrocellulose membrane (Bio-Rad).

The membrane was incubated for 1 hour in blocking solution containing 5% milk and 0.1% Tween-20, pH 7.6. This was followed by overnight incubation at 4° C. in the blocking buffer containing 5% BSA, 0.1% Tween-20 and rabbit anti-phosphoTrk (Cell Signaling, cat. #9141, 1:500), rabbit anti-phospho-Akt (Cell Signaling, cat. #9271, 1:1000) or rabbit anti-phospho-ERK1/2 antibody (Sigma, cat. #E7028, 1:5000). Subsequently, the labeled proteins were visualized by incubation with a horseradish peroxidase (HRP) conjugated anti-goat, mouse or rabbit IgG followed by development with a chemiluminescence substrate for HRP (Pierce). To determine the amounts of total TrkB, MAPK or Akt present in each lane, the nitrocellulose membranes were stripped of the antibodies in stripping buffer (Pierce) for 20 min and incubated with rabbit anti-TrkB (Cell Signaling, cat. #4603, 1:1000), rabbit anti-Erk1/2 (Cell Signaling, cat. #06-182, 1:1000) or rabbit anti-Akt antibody (Cell Signaling, cat. #9272, 1:1000) and then visualized as described above. Beta-Actin (Sigma, cat. #A5316, 1:20000 and GAPDH (Sigma, cat. #G9295) were probed as sample loading control.

Figure 2:
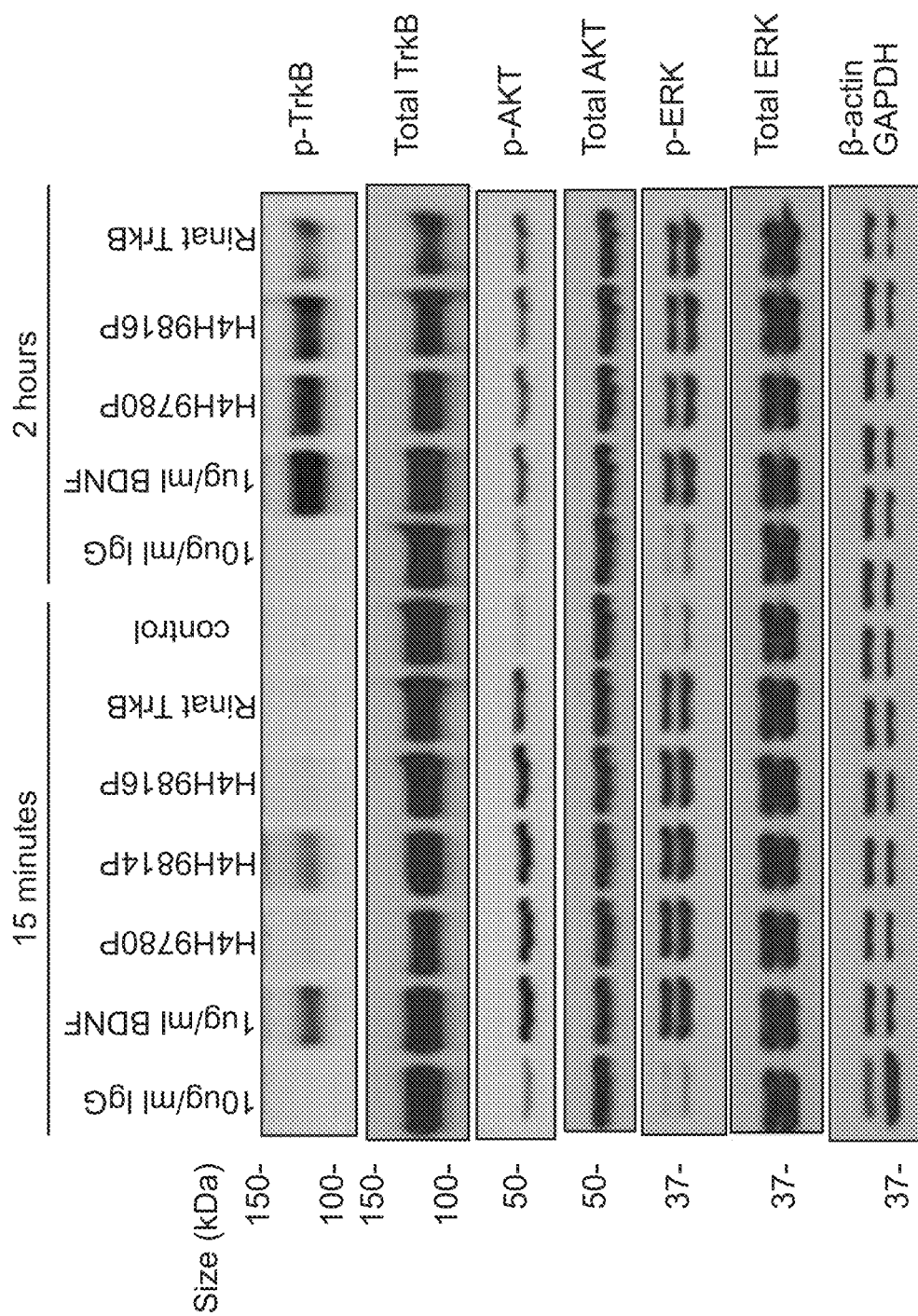
FIG. 2. Shows that the TrkB agonist antibody, H4H9816P2, activated the downstream pathways of MAPK/ERK and PI3K/Akt. The figure shows western blots of phospho-TrkB, total TrkB, phospho-Akt, total AKT, phospho-ERK, and total ERK at 15 minutes and 2 hours after treatment of primary cortical neurons isolated from postnatal day 1 homozygous humanized TRKB mouse pups with various TrkB agonist antibodies or BDNF.

Results Summary and Conclusions:

As shown in FIG. 2, at 15 mins after the incubation, while all the TrkB agonist Ab showed activation of MAPK/ERK and PI3K/Akt pathway, only BDNF and H4H9814P showed TrkB phosphorylation. 2 hrs after incubation all the TrkB agonist Abs showed activation of TrkB.

Figure 3:
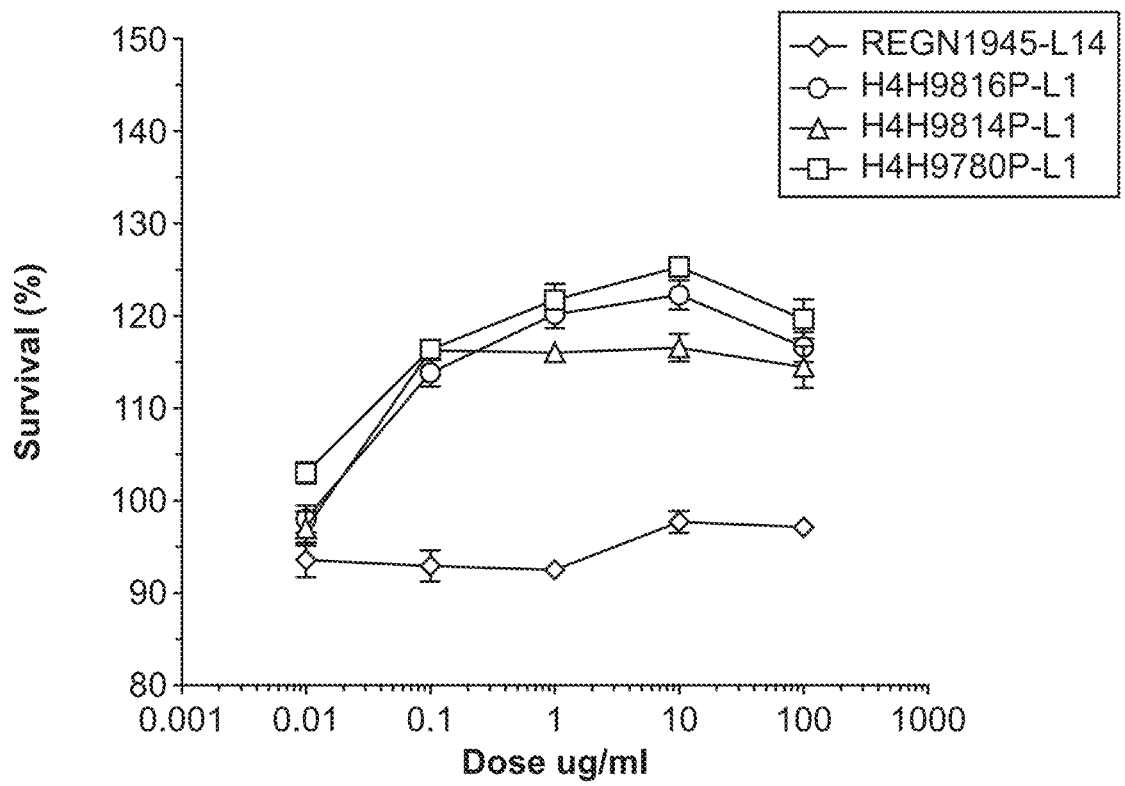
FIG. 3. Shows that three TrkB agonist antibodies dose dependently increased the survival of SH-SY5Y cells in vitro. The isotype control antibody had no effect on cell survival.

Example 10. Effect of Agonist Anti-TrkB Antibodies on Survival of SH-SY5Y Cells Human Neuroblastoma SH-SY5Y Cell Line In Vitro Culture Neuroblastoma cell line SH-SY5Y (Sigma ATCC #94030304, cat. #11C016) cells were plated in growth media containing DMEM:F12 (Invitrogen cat #11330), Pen/Strep (Invitrogen cat. #15140), FBS 10% (Invitrogen cat #10082-147) at 37 C in 5% CO2. At passage 23-27 cells were seeded into 96 well plates in differentiation media containing all-trans 10 uM Retinoic Acid (Alfa Aesar cat. #44540), DMEM:F12 (Invitrogen cat #11330), Pen/Strep (Invitrogen cat #15140), FBS 10% (Invitrogen cat #10082-147). Cells (30K/well) were differentiated for 4 days. Antibodies were screened in survival bioassay in which culture was changed to serum free differentiation media (100 ul/well) containing different doses of antibodies (100-0.01 ug/ml). After 2 days CCK8 (Dojindo, cat. #CK04) reagent was added (10u1/well), plates were incubated for 3-4 hours, OD was measured at 450 nm (Victor or FlexStation III) to determine the percentage of surviving cells. Data was normalized to the serum free media without treatment. Serum free treatment without antibodies=100% survival Results Summary and Conclusions:

As shown in FIG. 3 and Table 23, all of the agonist TrkB antibodies of the invention showed a significant dose-dependent increase in the survival of SH-SY5Y cells as compared to the negative isotype control antibody ($p<0.0001$ by two way ANOVA).

TABLE 24

| | Average % survival | | | |
|---|---|---|---|---|
| Dose ug/ml | H4H9816P-L1 | H4H9780P-L1 | H4H9814P-L1 | REGN1945-L14 (negative isotype control) |
| 100 | 116.7 | 119.7 | 114.5 | 97.1 |
| 10 | 122.3 | 125.3 | 116.6 | 97.7 |
| 1 | 120.2 | 121.7 | 116.0 | 92.5 |
| 0.1 | 113.9 | 116.4 | 116.3 | 92.9 |
| 0.01 | 98.0 | 103.0 | 97.0 | 93.6 |

Example 11. Pharmacokinetic Assessment of an Anti-TrkB Antibody in Humanized TrkB and WT Mice Evaluation of the pharmacokinetics of an anti-TrkB antibody, H4H9816P2 was conducted in humanized TrkB mice (mice homozygous for human TrkB expression, TrkB$^{hu/hu}$) and WildType (WT) mice. Cohorts contained 5 mice per mouse strain. All mice received a single subcutaneous (SC) 10 mg/kg dose. Blood samples were collected at 6 hours and 1, 2, 3, 6, 9, 16, 21 and 30 days post dosing. Blood was processed into serum and frozen at −80° C. until analyzed.

Circulating antibody concentrations were determined by total human IgG4/hIgG1 antibody analysis using the Gyro-Lab xPlore™ (Gyros, Uppsala, Sweden). Briefly, biotinylated mouse anti-human IgG4/IgG1-specific monoclonal antibody (REGN2567) diluted to 100 μg/mL in antibody dilution buffer (0.05% Tween-20+PBS) was captured on a Gyrolab Bioaffy 200 CD, which contained affinity columns preloaded with streptavidin-coated beads (Dynospheres™). The standard used for calibration in this assay was H4H9816P at concentrations ranging from 0.488 to 2000 ng/mL in dilution buffer (0.5% BSA+PBS) containing 0.1% normal mouse serum (NMS). Serum samples were diluted 1:100 in the antibody dilution buffer. Human IgG captured on the anti-REGN2567-coated affinity columns on the CD, run at room temperature, was detected by addition of 0.5 μg/mL Alexa-647-conjugated mouse anti-human kappa monoclonal antibody (REGN654) diluted in detection buffer (Rexxip F buffer); and the resultant fluorescent signal was recorded in response units (RU) by the GyroLab xPlore instrument. Sample concentrations were determined by interpolation from a standard curve that was fit using a 5-parameter logistic curve fit using the Gyrolab Evaluator Software. Average concentrations from 2 replicate experiments were used for subsequent PK analysis.

PK parameters were determined by non-compartmental analysis (NCA) using Phoenix®WinNonlin® software Version 6.3 (Certara, L. P., Princeton, NJ) and an extravascular dosing model. Using the respective mean concentration values for each antibody, all PK parameters including observed maximum concentration in serum ($C_{max}$), estimated half-life observed (t½), and area under the concentration curve versus time up to the last measureable concentration ($AUC_{last}$) were determined using a linear trapezoidal rule with linear interpolation and uniform weighting.

Results Summary and Conclusions:

Following 10 mg/kg s.c. administration of anti-TrkB antibody, H4H9816P2, similar maximum concentrations ($C_{max}$) of antibody were observed by day 1 or 2 in both TrkB$^{hu/hu}$ and WT mice (135 and 131 μg/mL, respectively, see Table 26). By day 9, H4H9816P2 exhibited steeper drug elimination in TrkB$^{hu/hu}$ mice than in WT mice, indicating a target-mediated effect. Day 30 antibody concentrations were about 35-fold less in TrkB$^{hu/hu}$ mice. Antibody exposure ($AUC_{last}$) for H4H9816P2 in WT mice was ~1.7-fold higher than seen in TrkB$^{hu/hu}$ mice (1730 and 1020 d*μg/mL, respectively). WT mice also exhibited about a 3-fold increase in half-life (T½) over TrkB$^{hu/hu}$ mice (8.4 and 2.9 days, respectively).

Figure 4:
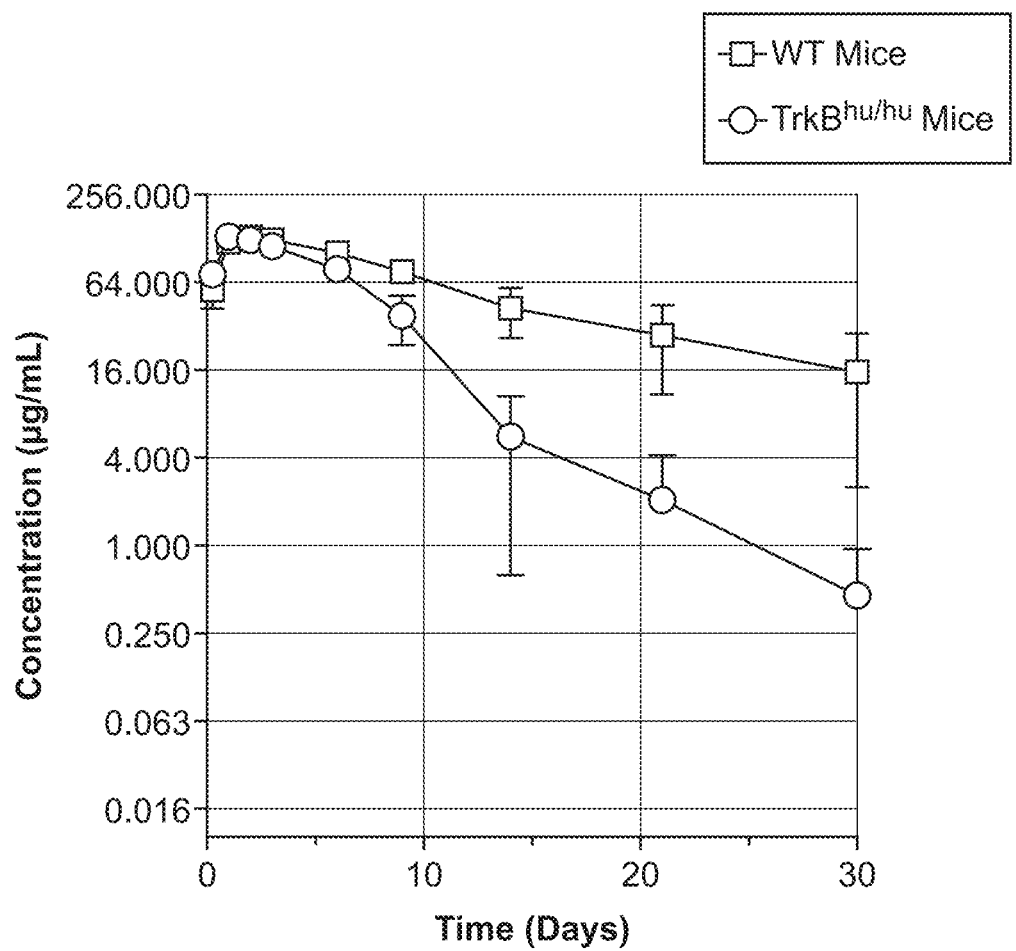
FIG. 4. Shows the pharmacokinetic profiles of the anti-TrkB agonist antibody H4H9816P2 in TrkB$^{hu/hu}$ mice and Wild Type mice. Mice were administered a single 10 mg/kg subcutaneous dose on day 0. Concentrations of total H4H9816P2 in serum were measured using a Gyros immunoassay. Data points on post-dose 6 hours, 1, 2, 3, 6, 9, 16, 21 and 30 days indicate the mean concentration of antibody. Total antibody concentrations of H4H9816P2 are represented as black solid circles for TrkB$^{hu/hu}$ mice and solid black squares for WildType mice. Data are plotted as mean±SD.

A summary of the data for total anti-TrkB antibody concentrations are summarized in Table 25, mean PK parameters are described in Table 26 and mean total antibody concentrations versus time are shown in FIG. 4.

TABLE 25

Mean Concentrations (±SD) of Total IgG in Serum Following a Single 10 mg/kg Sub-Cutaneous Injection of H4H9816P2 in TrkB$^{hu/hu}$ and WildType Mice Over Time

| Antibody | Time (d) | Total mAb Concentration in Mouse Serum 10 mg/kg | |
|---|---|---|---|
| | | Mean (μg/mL) | +/−SD |
| TrkB$^{hu/hu}$ Mice | 0.25 | 72.42 | 4.06 |
| | 1 | 132.0 | 18.0 |
| | 2 | 124.9 | 15.9 |
| | 3 | 113.4 | 11.8 |
| | 6 | 78.72 | 9.98 |
| | 9 | 37.74 | 14.0 |
| | 16 | 5.592 | 4.97 |
| | 21 | 2.060 | 2.11 |
| | 30 | 0.447 | 0.506 |

TABLE 25-continued

Mean Concentrations (±SD) of Total IgG in Serum Following a Single 10 mg/kg Sub-Cutaneous Injection of H4H9816P2 in TrkB$^{hu/hu}$ and WildType Mice Over Time

| Antibody | Time (d) | Total mAb Concentration in Mouse Serum 10 mg/kg | |
|---|---|---|---|
| | | Mean (μg/mL) | +/−SD |
| WildType Mice | 0.25 | 56.73 | 14.5 |
| | 1 | 120.8 | 6.26 |
| | 2 | 131.2 | 7.54 |
| | 3 | 125.7 | 7.46 |
| | 6 | 101.9 | 11.4 |
| | 9 | 75.94 | 7.06 |
| | 16 | 42.61 | 16.1 |
| | 21 | 27.75 | 16.9 |
| | 30 | 15.52 | 13.0 |

Abbreviations: Time = Time in days post single-dose injection; d = Day of study; SD = Standard Deviation.

TABLE 26

Summary of Pharmacokinetic Parameters

| | | H4H9816P2 | |
|---|---|---|---|
| Parameter | Units | TrkB$^{hu/hu}$ Mice | WildType Mice |
| $C_{max}$ | μg/mL | 135 ± 15 | 131 ± 7.5 |
| $T_{max}$ | d | 1.4 ± 0.56 | 2.0 ± 0 |
| $T_{1/2}$ | d | 2.94 ± 1.1 | 8.36 ± 3.9 |
| $AUC_{last}$ | d · μg/mL | 1020 ± 150 | 1730 ± 310 |

PK parameters were derived from mean concentration versus time profiles. $T_{1/2}$ and $AUC_{last}$ are based on concentrations out to day 30.
Abbreviations:
$C_{max}$ = Peak concentration;
AUC = Area under the concentration-time curve;
$AUC_{last}$ = AUC computed from time zero to the time of the last positive concentration;
$T_{1/2}$ = Terminal half-life of elimination;
$T_{max}$ = the time after administration of antibody when the maximum serum concentration is reached Example 12: Ability of Anti-Mouse TrkB Monoclonal Antibodies to Block Interaction Between Mouse or Rat TrkB and its Ligand BDNF (Brain Derived Neurotrophic Factor)

Anti-mouse TrkB monoclonal antibodies (mAbs) were generated by immunizing TrkB humanized mice with mouse TrkB protein. The three lead mAbs identified from this immunization are; M2aM14173N, M2aM14178N and M2aM14179N. Lead mAbs of the invention were characterized for their ability to block interaction of mouse or rat TrkB to plate-bound BDNF in a blocking ELISA.

Experiments were carried out using the following procedure. Human BDNF was coated at a concentration of 0.5 μg/mL (for blocking mouse TrkB.hFc interaction) or 0.3 μg/mL (for blocking rat TrkB.mmh interaction) in PBS on 96-well microtiter plate and incubated overnight at 4° C. Nonspecific binding sites were subsequently blocked using a 5% (w/v) solution of BSA in PBS (assay buffer). In a 96-well dilution plate, 850 pM mouse TrkB.hFc or rat TrkB.mmh was mixed with the three-fold serially diluted anti-mouse TrkB antibodies and control antibody. The final antibody concentrations ranged from 1.69 pM to 100 nM. The protein-antibody mix was incubated at room temperature (RT) for 1 hour. The pre-bound mix was then transferred in duplicates to microtiter plates coated with BDNF. A control containing assay buffer alone was included to calculate the baseline of the assay. The ELISA plates were incubated at RT for 1 hour and then washed with plate washing solution. Plate-bound mouse TrkB.hFc was detected with HRP-conjugated goat anti-human Fcγ fragment specific antibody (Jackson Immunoresearch) and rat TrkB.mmh was detected with HRP-conjugated anti-histidine antibody (Qiagen). The plates were incubated with detection antibody for 1 hour at RT and then washed with plate washing solution. The assay plates were developed with TMB colorimetric substrates according to the manufacturer's recommended procedure.

The absorbance at 450 nm for each well was recorded and plotted as a function of the concentration of antibody. Data was analyzed in GraphPad Prism software using a four-parameter logistic equation over an 11-point dose response curve and $IC_{50}$ values were calculated. The calculated $IC_{50}$ value, defined as the concentration of antibody required to reduce 50% of TrkB binding to BDNF, was used as an indicator of blocking potency. Percent blockade at maximum concentration of the antibody tested was calculated as an indicator of the ability of the antibodies to block the binding of TrkB to BDNF on the plate relative to the baseline of the assay. Binding signal of 850 pM mouse or rat TrkB in absence of the antibody was defined as 100% binding or 0% blocking. The baseline signal of assay buffer alone was defined as 0% binding or 100% blocking.

Results Summary and Conclusions

The ability of anti-mouse TrkB antibodies to block mouse or rat TrkB binding to BDNF was assessed using blocking ELISAs.

Figure 5A:
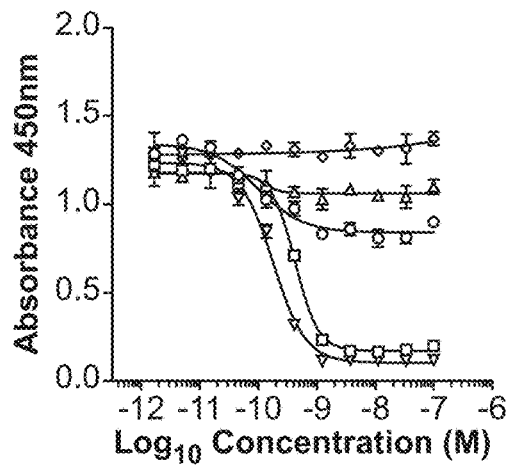
FIG. 5. Consists of FIG. 5A and FIG. 5B which show the ability of anti-mouse TrkB monoclonal antibodies to block interaction between mouse or rat TrkB and its ligand BDNF (Brain Derived Neurotrophic Factor). ELISA-based methods were used to assess the binding of (FIG. 5A with two graphs) mouse TrkB.hFc and (FIG. 5B with two graphs) rat TrkB.mmh to plate coated BDNF in presence of a range of concentrations of Anti-mouse TrkB and isotype control mAbs. The insert in (FIG. 5A with two graphs) shows the dose-response curve of mouse TrkB.hFc (REGN2277) binding to BDNF with an $EC_{50}$ value of 780 pM. The insert in (FIG. 5B with two graphs) shows the dose-response curve of rat TrkB.mmh (REGN1808) binding to BDNF with an $EC_{50}$ value of 2.2 nM. Molarity (M) indicates antibody concentration for mAbs. Error bars represent Standard Deviation.
Figure 5A:
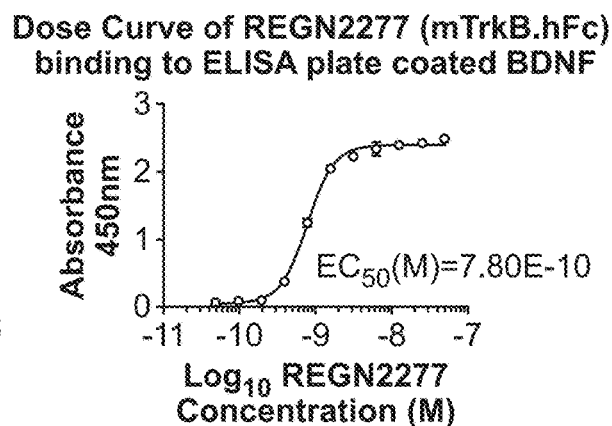
Figure 5B:
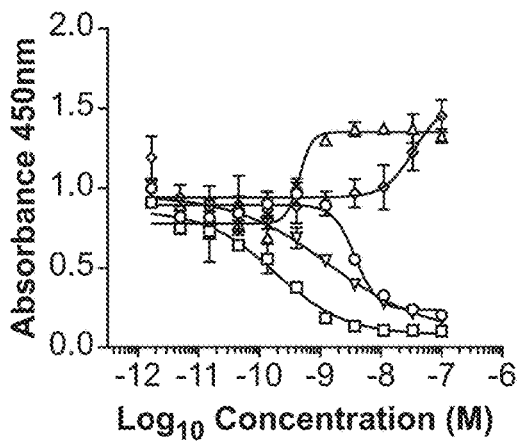
Figure 5B:
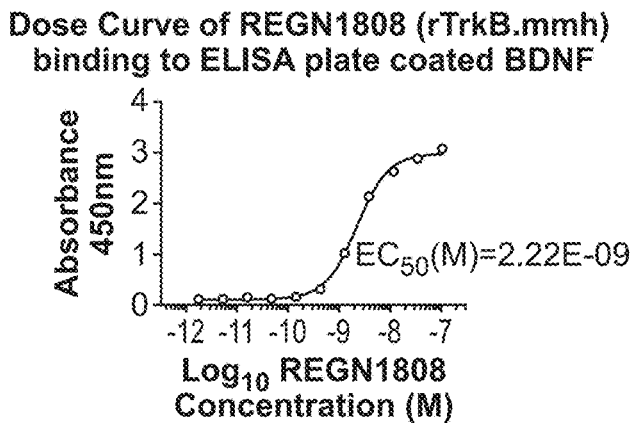

The blocking results are summarized in Table 27 and in FIGS. 5A and B. The % blockade is reported for all antibodies and calculated at the highest antibody concentration (100 nM) tested. ICso values are shown only for antibodies blocking >50% of mouse or rat TrkB binding to BDNF. Out of the three antibodies of this invention, anti-mouse TrkB mAb, M2aM14178N blocked >50% of both mouse and rat TrkB protein binding to BDNF. M2aM14178N blocked binding of 850 pM mouse TrkB.hFc with an $IC_{50}$ of 426 pM and % blockade of 84.4%. M2aM14178N blocked 850 pM rat TrkB.mmh binding to BDNF with an $IC_{50}$ value of 184 pM and % blockade of 89.5%. M2aM14173N showed 29.7% blocking of 850 pM mouse TrkB.hFc binding to BDNF. M2aM14173N showed 80.7% blocking of 850 pM rat TrkB.mmh binding to BDNF with an $IC_{50}$ value of 3.81 nM. M2aM14179N blocked 11.6% of mouse TrkB.hFc binding to BDNF. M2aM14179N showed an increase in rat TrkB.mmh binding to BDNF at concentrations greater than 1 nM.

The comparator anti-mouse TrkB mAb, H1M8037C, blocked 850 pM mouse TrkB.hFc binding to BDNF with an $IC_{50}$ value of 180 pM and % blockade of 91.5%. H1M8037C blocked 850 pM rat TrkB.mmh binding with an $IC_{50}$ value of 1.42 nM and % blockade of 83.3%. The mIgG2a isotype control mAb, REGN1097, did not show any blocking of mouse or rat TrkB, under identical assay conditions. At concentrations greater than 10 nM, REGN1027 showed an increase of rat TrkB binding.

TABLE 27

Summary of $IC_{50}(M)$ values for Anti-mouse TrkB Blockade of mouse or rat TrkB Binding to BDNF

| AbPID | Ab blocking of 780 pM mouse TrkB.hFc binding to plate-coated BDNF | | Ab blocking of 780 pM rat TrkB.mmh binding to plate-coated BDNF | |
|---|---|---|---|---|
| | $IC_{50}$ [M] | % Blockade with 100 nM antibody | $IC_{50}$ [M] | % Blockade with 100 nM antibody |
| M2aM14173N | not calculated | 29.7 | 3.81E−09 | 80.7 |
| M2aM14178N | 4.26E−10 | 84.4 | 1.84E−10 | 89.5 |
| M2aM14179N | not calculated | 11.6 | not calculated | −38.1 |
| H1M8037C (Comparator) | 1.80E−10 | 91.5 | 1.42E−09 | 83.3 |
| Negative Isotype control (REGN1097) | not calculated | No blocking | not calculated | −9.33 |

100% Blockade = OD450 nm value of wells with HRP-conjugated secondary antibody in assay buffer alone (no mouse or rat TrkB protein).
0% Blockade = OD450 nm value of wells with HRP-conjugated secondary antibody in assay buffer in presence of mouse or rat TrkB protein (no TrkB antibody).
Negative Max Blocking % indicate an increase of TrkB binding detected in the presence of antibody.
not calculated = $IC_{50}$ values not quantitative for antibodies blocking <50% at the highest concentration tested.

Example 13. Ability of Anti-Human TrkB Monoclonal Antibodies to Block the Interaction Between Human TrkB and its Natural Ligands Human BDNF and NT4

The ability of anti-human TrkB antibodies, designated as H4H9814P, H4H9816P2 and H4H9780P, to block TrkB protein binding to plate captured BDNF or NT-4 was measured using two competition sandwich ELISAs. In the assays, various concentrations of anti-TrkB antibody were pre-mixed with a constant amount of dimeric TrkB protein and the reduction of the TrkB binding to the plate immobilized BDNF or NT-4, due to the presence of the antibody, was calculated.

The recombinant dimeric TrkB protein used in the experiments was comprised of a portion of the human TrkB extracellular domain (aa Cys32-His430) expressed with the Fc portion of the human IgG1 at the c-terminus (hTrkB-hFc; Accession #NP_006171.2, molecular weight 69,700 daltons). The BDNF and NT-4 proteins were comprised of the extracellular domain of human BDNF (aa His129-Arg247, Accession #P23560, R&D Systems) or NT-4 (aa Gly81-Ala210, Accession #P34130, R&D Systems), respectively. Two isotype antibody controls, an anti-Fel d 1 human IgG4 antibody, and an antibody specific to a-Fel d 1 antibody with mouse IgG1, were included as controls for IgG background detection.

Experiments were carried out using the following procedure. Human BDNF or NT-4 were separately coated at a concentration of 0.5 μg/mL or 2 μg/mL, respectively, in PBS on a 96-well microtiter plate overnight at 4° C. Nonspecific binding sites were subsequently blocked using BSA solution in PBS. Blocking solution and dilution buffer contained 5% (w/v) solution of BSA in PBS for assay with BDNF coat, or 0.5% (w/v) solution of BSA in PBS for assay with NT-4 coat. On separate microtiter plates, a constant amount of 500 pM of hTrkB-hFc protein was added to serial dilutions of antibodies with final concentrations ranging from 1.7 pM to 100 nM, and solutions with no antibody present. (The constant concentration of hTrkB-hFc for antibody inhibition assays was selected from the approximate midway point within the linear portion of individual binding curves of hTrkB-hFc to plate-coated hBDNF or hNT-4). After one hour incubation at room temperature, antibody-protein complexes with 500 pM constant concentration of hTrkB-hFc protein were transferred to microtiter plates coated with hBDNF or hNT-4. After one hour incubation at room temperature, the wells were washed, and plate-bound hTrkB-hFc was detected with anti-human Fcγ fragment specific goat polyclonal antibodies conjugated with horseradish peroxidase (JacksonImmunoResearch). The plate was then developed using TMB substrate solution (BD Biosciences) according to manufacturer's recommendation and absorbance at 450 nm was measured on a Victor plate reader (PerkinElmer™)

Data analysis was performed using a sigmoidal dose-response model within Prism™ software (GraphPad). The calculated $IC_{50}$ value, defined as the concentration of antibody required to reduce 50% of hTrkB-hFc binding to hBDNF or hNT-4, was used as an indicator of blocking potency. Percent blockade at maximum concentration of the antibody tested was calculated as an indicator of the ability of the antibodies to block the binding of 500 pM of hTrkB-hFc to hBDNF or hNT-4 on the plate, relative to the baseline of the assay. In the calculation, binding signal of the sample of 500 pM of hTrkB-hFc without the presence of the antibody was referenced as 100% binding or 0% blocking; and the baseline signal of the sample of buffer without hTrkB-hFc or the antibody was referenced as 0% binding or 100% blocking.

Results Summary and Conclusions:

The ability of anti-TrkB antibodies to block TrkB binding to BDNF or NT-4 was assessed using two competition sandwich ELISAs. Human TrkB-hFc binding to hBDNF or hNT-4 coated on 96-well microtiter plates, in the presence of serially diluted antibodies or no antibody controls, were detected with HRP-conjugated anti-human Fcγ fragment specific goat polyclonal antibodies. $IC_{50}$ values were calculated and used as the potency indicator of antibody blocking hTrkB-hFc binding to hBDNF or hNT-4. In addition, the maximum blockade of 500 pM hTrkB-hFc with each antibody at the highest tested concentration was calculated and compared.

The blocking results are summarized in Table 28. The % blockade is reported for all antibodies and calculated at the highest tested antibody concentration of 100 nM. Negative % blockade indicates an increase of TrkB binding detected in the presence of antibody. $IC_{50}$ values are shown for antibodies blocking>50% of TrkB binding to BDNF or NT-4. $IC_{50}$ values are not quantitative for antibodies blocking <50% and was reported as (–).

At the highest concentration of antibody tested, one (H4H9780P) of the three anti-TrkB antibodies blocked >50% hTrkB binding to BDNF or NT-4 ligands with $IC_{50}$ values of 150 pM and 180 pM, respectively, with percent blockade at 100 nM antibody of 93% for BDNF and 80% for NT-4. At 3.7 nM, this antibody blocked 500 pM hTrkB-hFc binding to NT-4 with 99%. The decrease of % blockade at the highest tested concentrations may be attributed to H4H9780P non-specific binding to the microtiter plate and detection of this binding with HRP-conjugated anti-human Fcγ fragment specific polyclonal antibodies.

Two of the three anti-TrkB antibodies (H4H9814P and H4H9816P2) and irrelevant blocking control antibodies blocked <50% of hTrkB binding to BDNF or NT-4. The comparator blocked 500 pM hTrkB-hFc binding >50% to both BDNF and NT-4.

TABLE 28

| Ab PID | Ab blocking 500 pM hTrkB-hFc binding to plate-coated hBDNF | | Ab blocking 500 pM hTrkB-hFc binding to plate-coated hNT-4 | |
| --- | --- | --- | --- | --- |
| | IC50 (M) | % Blockade with 100 nM antibody | IC50 (M) | % Blockade with 100 nM antibody |
| H4H9814P | — | 6 | — | 38 |
| H4H9816P2 | — | −56 | — | −123 |
| H4H9780P | 1.5E−10 | 93 | 1.8E−10 | 80* |
| CONTROLS | | | | |
| a-TrkB-mIgG1 (H1M8037C comparator) | 1.7E−10 | 97 | 4.5E−11 | 95 |
| hIgG4 negative isotype control | — | −31 | — | −45 |
| mIgG1 negative isotype control | — | −19 | — | −14 |

*Blocked 99% at 3.7 nM H4H9780P antibody concentration.

Example 14. Octet Cross-Competition Between Different Anti-hTrkB Monoclonal Antibodies To assess whether two antibodies compete with one another for binding to their epitopes on hTrkB-mmh, binding competition between anti-hTrkB monoclonal antibodies was determined using a real time, label-free bio-layer interferometry assay on an Octet RED384 biosensor (Pall ForteBio Corp.). Cross competition experiments were performed at 25° C. in 0.01 M HEPES pH7.4, 0.15M NaCl, 3.4 mM EDTA, 0.05% v/v Surfactant Tween-20, 0.1 mg/mL BSA (HBS-EP buffer) with the plate shaking at the speed of 1000 rpm. All anti-hTrkB antibody and hTrkB-mmh solutions tested were prepared in Octet HBS-EP buffer. To assess whether 2 antibodies were able to compete with one another for binding to their respective epitopes on hTrkB-mmh, approximately ~0.14-0.24 nm of hTrkB-mmh was first captured on anti-His coated Octet biosensor tips from wells containing 50 μg/mL of hTrkB-mmh for 5 minutes. The hTrkB-mmh captured Octet biosensor tips were saturated by submerging for 5 minutes into wells containing 50 ug/ml of the first anti-hTrkB monoclonal antibody (hereby referred to as mAb-1), followed by submerging in wells containing the second anti-HTrkB monoclonal antibody (hereby referred to as mAb-2) for an additional 5 minutes. Between steps, the Octet biosensor tips were washed in HBS-EP buffer for 30 seconds.

The real-time binding response was monitored during the course of the experiment and the binding response at the end of every step was recorded. The response of mAb-2 binding to hTrkB.mmh pre-complexed with mAb-1 was compared and competitive/non-competitive behavior of different anti-hTrkB monoclonal antibodies was determined using a 60% inhibition threshold.

Table 29 explicitly defines the relationships of antibodies competing in both directions, independent of the order of binding.

Results:

TABLE 29

Cross-competition of anti-hTrkB antibodies
for binding to human hTrkB.mmh.

| mAb-1 | mAb-2 |
|---|---|
| H4H9814P | H4H9816P2 |
|  | H4H9814P |
| H4H9816P2 | H4H9814P |
|  | H4H9816P2 |
| H4H9780P | H4H9780P |
| H1M8037C (comparator) | H1M8037C (comparator) |

Example 15. Biacore Binding Kinetics of Surrogate
Anti-Mouse TrkB Monoclonal Antibodies Binding
to Different TrkB Reagents Measured at 25° C.

To assess whether two antibodies compete with one another for binding to their epitopes on mTrkB-mmh, binding competition between anti-mTrkB monoclonal antibodies was determined using a real time, label-free bio-layer interferometry assay on an Octet HTX biosensor (Pall ForteBio Corp.). Cross competition experiments were performed at 25° C. in 0.01 M HEPES pH7.4, 0.15M NaCl, 3.4 mM EDTA, 0.05% v/v Surfactant Tween-20, 0.1 mg/mL BSA (HBS-EP buffer) with the plate shaking at the speed of 1000 rpm. All anti-mTrkB antibody and mTrkB-mmh solutions tested were prepared in Octet HBS-EP buffer. To assess whether 2 antibodies were able to compete with one another for binding to their respective epitopes on mTrkB-mmh, approximately ~0.20-0.27 nm of mTrkB-mmh was first captured on anti-His coated Octet biosensor tips from wells containing 20 µg/mL of mTrkB-mmh for 5 minutes. The mTrkB-mmh captured Octet biosensor tips were saturated by submerging for 5 minutes into wells containing 50 ug/ml of the first anti-mTrkB monoclonal antibody (hereby referred to as mAb-1), followed by submerging in wells containing the second anti-mTrkB monoclonal antibody (hereby referred to as mAb-2) for an additional 3 minutes. Between steps, the Octet biosensor tips were washed in HBS-EP buffer for 30 seconds.

The real-time binding response was monitored during the course of the experiment and the binding response at the end of every step was recorded. The response of mAb-2 binding to mTrkB.mmh pre-complexed with mAb-1 was compared and competitive/non-competitive behavior of different anti-mTrkB monoclonal antibodies was determined using a 50% inhibition threshold.

Table 30 explicitly defines the relationships of antibodies competing in both directions, independent of the order of binding.

Results:

TABLE 30

Cross-competition of anti-mTrkB antibodies
for binding to mouse hTrkB.mmh.

| mAb-1 | mAb-2 |
|---|---|
| M2aM14173N | M2aM14178N |
|  | M2aM14173N |
| M2aM14178N | M2aM14173N |
|  | M2aM14178N |
| M2aM14179N | M2aM14179N |
| H1M8037C (comparator) | H1M8037C (comparator) |

Example 16: Octet Blocking: Blocking of
Anti-Human TrkB or Anti-Mouse TrkB Antibodies
from Binding to TrkB by BDNF or NT-4

Experiment 1.

Blocking of anti-human TrkB or anti-mouse TrkB antibodies from binding to TrkB by BDNF or NT-4 was evaluated using a real-time bio-layer interferometry (BLI) based Octet HTX instrument. The entire study was performed in 10 mM HEPES pH 7.4, 300 mM NaCl, 3 mM EDTA, 1mg/mL BSA, 0.02% NaN3 and 0.05% v/v Surfactant Tween-20 (HBS-EBT running buffer) at 25° C. All the samples were dispensed in a 384 tilted well plate and the plate was placed on the orbital shaker with the shake speed of 1000 rpm. hTrkB.mFc was captured on anti-mFc (AMC) Octet sensors while hTrkB.hFc or mTrkB.hFc were captured on anti-hFc (AHC) Octet sensors by dipping in wells containing 10 µg/mL of TrkB reagents for 2 minutes. hTrkB.mFc or hTrkB.hFc captured Octet biosensors were saturated by dipping in wells containing 20 nM of BDNF, hNT-4, or mNT-4 for 2 minutes followed by dipping Octet biosensors in wells containing 300 nM of different TrkB mAbs for 4 minutes. Binding of TrkB mAbs to the complex of TrkB and BDNF, hNT-4, or mNT-4 was determined using Scrubber 2.0c analysis software.

Binding of any anti-human TrkB or anti-mouse TrkB antibodies of this invention was not blocked by both BDNF and NT-4 as reported in Table 31 and Table 32.

TABLE 31

Binding of anti-human TrkB monoclonal antibodies to
the complex of hTrkB-mFc and BDNF or human NT-4.

| | | | Anti-human TrkB antibody Binding (nm) | | |
|---|---|---|---|---|---|
| Capture Surface | Capture Level (nm) | mAb | No Ligand | BDNF Saturation (0.05 ± 0.007) nm | hNT-4 Saturation (0.05 ± 0.006) nm |
| hTrkB.mFc | 0.29 ± 0.01 | REGN1945 (negative isotype control) | 0.01 ± 0.01 | 0.00 ± 0.00 | 0.00 ± 0.00 |
| | | H4H9780P | 0.18 ± 0.01 | 0.20 ± 0.014 | 0.2 ± 0.007 |
| | | H4H9814P | 0.18 ± 0.01 | 0.22 ± 0.006 | 0.23 ± 0.00 |
| | | H4H9816P2 | 0.19 ± 0.00 | 0.26 ± 0.007 | 0.24 ± 0.007 |

TABLE 31-continued

Binding of anti-human TrkB monoclonal antibodies to
the complex of hTrkB-mFc and BDNF or human NT-4.

| | | | Anti-human TrkB antibody Binding (nm) | | |
|---|---|---|---|---|---|
| Capture Surface | Capture Level (nm) | mAb | No Ligand | BDNF Saturation (0.05 ± 0.007) nm | hNT-4 Saturation (0.05 ± 0.006) nm |
| hTrkB.hFc | 0.47 ± 0.01 | H1M8037C (Comparator) | 0.38 ± 0.01 | 0.07 ± 0.00 | 0.10 ± 0.006 |

The values of anti-human TrkB antibodies binding to the complex of hTrkB.mFc or hTrkB.hFc with BDNF or hNT-4 represent an average of binding response measured using 3 independent Octet biosensors along with the standard deviation. Binding of BDNF or hNT-4 to hGFRa3.mFc did not inhibit the binding of any anti-human TrkB antibodies.

TABLE 32

Binding of anti-mouse TrkB monoclonal antibodies to
the complex of mTrkB-hFc and BDNF or mouse NT-4.

| | | | Anti-mouse TrkB antibody Binding (nm) | | |
|---|---|---|---|---|---|
| Capture Surface | Capture Level (nm) | mAb | No Ligand | BDNF Saturation (0.07 ± 0.006) nm | mNT-4 Saturation (0.07 ± 0.005) nm |
| mTrkB.hFc | 0.47 ± 0.01 | REGN1318 (negative isotype control) | 0.01 ± 0.00 | 0.00 ± 0.00 | 0.00 ± 0.006 |
| | | M2aM14173N | 0.42 ± 0.006 | 0.38 ± 0.006 | 0.4 ± 0.00 |
| | | M2aM14178N | 0.47 ± 0.00 | 0.35 ± 0.007 | 0.41 ± 0.006 |
| | | M2aM14179N | 0.42 ± 0.006 | 0.44 ± 0.006 | 0.43 ± 0.006 |
| | | H1M8037C (Comparator) | 0.42 ± 0.006 | 0.06 ± 0.006 | 0.11 ± 0.00 |

The values of anti-mouse TrkB antibodies binding to the complex of mTrkB.mFc with BDNF or mNT-4 represent an average of binding response measured using 3 independent Octet biosensors along with the standard deviation. Binding of BDNF or mNT-4 to mGFRa3.hFc did not inhibit the binding of any anti-mouse TrkB antibodies.

Experiment 2.

Blocking of BDNF or NT-4 from binding to TrkB by anti-human TrkB or anti-mouse TrkB antibodies was evaluated using a real-time bio-layer interferometry (BLI) based Octet HTX instrument. The entire study was performed in 10 mM HEPES pH 7.4, 300 mM NaCl, 3 mM EDTA, 1mg/mL BSA, 0.02% NaN3 and 0.05% v/v Surfactant Tween-20 (HBS-EBT running buffer) at 25° C. All the samples were dispensed in a 384 tilted well plate and the plate was placed on the orbital shaker with the shake speed of 1000 rpm. hTrkB.mFc was captured on anti-mFc (AMC) Octet sensors while hTrkB.hFc or mTrkB.hFc were captured on anti-hFc (AHC) Octet sensors by dipping in wells containing 10 µg/mL of TrkB reagents for 2 minutes. hTrkB.mFc or hTrkB.hFc captured Octet biosensors were saturated by dipping in wells containing 300 nM of different TrkB mAbs for 4 minutes followed by dipping Octet biosensors in wells containing 20 nM of BDNF, hNT-4, or mNT-4 for 2 minutes. Binding of BDNF, hNT-4, or mNT-4 to the complex of TrkB and different TrkB mAbs was determined using Scrubber 2.0c analysis software.

Binding of 1 out of 3 anti-human TrkB antibodies of this invention blocked the binding of BDNF and hNT-4 as reported in Table 33. Binding of 1 out of 3 anti-mouse TrkB antibodies of this invention partially blocked the binding of BDNF and mNT-4 as reported in Table 34.

TABLE 33

Binding of BDNF or human NT-4 to the complex of hTrkB-mFc and anti-human TrkB monoclonal antibodies.

| | | | BDNF Binding | | hNT-4 Binding | |
|---|---|---|---|---|---|---|
| Capture Surface | Capture Level (nm) | mAb | mAb Binding (nm) | BDNF | mAb Binding (nm) | hNT-4 |
| hTrkB.mFc | 0.28 ± 0.01 | No mAb | N/A | 0.05 ± 0.007 | N/A | 0.04 ± 0.005 |
| | | REGN1945(negative isotype control) | 0.01 ± 0.01 | 0.04 ± 0.01 | 0.01 ± 0.01 | 0.033 ± 0.006 |
| | | H4H9780P | 0.18 ± 0.01 | 0.01 ± 0.00 | 0.18 ± 0.01 | 0.007 ± 0.006 |
| | | H4H9814P | 0.18 ± 0.01 | 0.05 ± 0.00 | 0.18 ± 0.01 | 0.04 ± 0.00 |
| | | H4H9816P2 | 0.19 ± 0.00 | 0.057 ± 0.006 | 0.18 ± 0.01 | 0.043 ± 0.006 |
| hTrkB.hFc | 0.48 ± 0.01 | H1M8037C (Comparator) | 0.38 ± 0.01 | −0.017 ± 0.006 | 0.39 ± 0.01 | −0.013 ± 0.006 |

The values of BDNF or hNT-4 binding to the complex of hTrkB.mFc or hTrkB.hFc with anti-human TrkB antibodies represent an average of binding response measured using 3 independent Octet biosensors along with the standard deviation. Binding of H4H9780P to hGFRa3.mFc blocked the binding of BDNF and hNT-4.

TABLE 34

Binding of BDNF or mouse NT-4 to the complex of mTrkB-hFc and anti-mouse TrkB monoclonal antibodies.

| Capture Surface | Capture Level (nm) | mAb | BDNF Binding | | hNT-4 Binding | |
| --- | --- | --- | --- | --- | --- | --- |
| | | | mAb Binding (nm) | BDNF | mAb Binding (nm) | hNT-4 |
| mTrkB.hFc | 0.48 ± 0.01 | No mAb | N/A | 0.07 ± 0.01 | N/A | 0.07 ± 0.005 |
| | | REGN1318 (negative isotype control) | 0.01 ± 0.00 | 0.06 ± 0.00 | 0.01±0.00 | 0.06 ± 0.00 |
| | | M2aM14173N | 0.42 ± 0.006 | 0.07 ± 0.00 | 0.413 ± 0.006 | 0.06 ± 0.00 |
| | | M2aM14178N | 0.47 ± 0.00 | 0.05 ± 0.00 | 0.47 ± 0.01 | 0.033 ± 0.006 |
| | | M2aM14179N | 0.42 ± 0.006 | 0.07 ± 0.00 | 0.41±0.00 | 0.06 ± 0.00 |
| | | H1M8037C (Comparator) | 0.42 ± 0.006 | −0.017 ± 0.006 | 0.40 ± 0.00 | −0.02 ± 0.00 |

The values of BDNF or mNT-4 binding to the complex of mTrkB.hFc and anti-mouse TrkB antibodies represent an average of binding response measured using 3 independent Octet biosensors along with the standard deviation. Binding of M2aM14178N to mTrkB.hFc partially blocked the binding of BDNF and mNT-4.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

We claim:

1. A method of treating a disease or disorder associated with TrkB activity or expression, or for ameliorating at least one symptom associated with the disease or disorder associated with TrkB activity or expression which is characterized by nerve cell injury or nerve cell degeneration in a subject in need thereof, comprising administering a therapeutically effective amount of an isolated antibody or antigen-binding fragment thereof that binds specifically to tropomyosin receptor kinase B (TrkB), wherein the antibody or antigen-binding fragment thereof comprises a set of six complementarity determining regions (HCDR1-HCDR2-HCDR3-LCDR1-LCDR2-LCDR3) comprising an HCDR1 comprising the amino acid sequence of SEQ ID NO:4, an HCDR2 comprising the amino acid sequence of SEQ ID NO:6, an HCDR3 comprising the amino acid sequence of SEQ ID NO:8, an LCDR1 comprising the amino acid sequence of SEQ ID NO:12, an LCDR2 comprising the amino acid sequence of SEQ ID NO:14, and an LCDR3 comprising the amino acid sequence of SEQ ID NO:16 to the subject.

2. The method of claim 1, wherein the disease or disorder is a disease or disorder of the eye selected from the group consisting of: glaucoma, diabetic retinopathy, age-related macular degeneration, ischemic optic neuropathy, optic neuritis, retinal ischemia, photoreceptor degeneration, retinitis pigmentosa, Leber Congenital Amaurosis, Leber's hereditary optic neuropathy, Stargardt disease, and retinal artery or vein occlusions.

3. The method of claim 2, wherein the disease or disorder is glaucoma.

4. The method of claim 3, wherein the isolated antibody or antigen-binding fragment thereof comprises a heavy chain variable region comprising the amino acid sequence of SEQ ID NO:2 and a light chain variable region comprising the amino acid sequence of SEQ ID NO:10.

5. The method of claim 4, wherein the antibody or antigen-binding fragment thereof is administered to the subject by intravitreal injection.

6. The method of claim 3, wherein the antibody or antigen-binding fragment thereof is administered to the subject by intravitreal injection.

7. The method of claim 2, wherein the isolated antibody or antigen-binding fragment thereof comprises a heavy chain variable region comprising the amino acid sequence of SEQ ID NO:2 and a light chain variable region comprising the amino acid sequence of SEQ ID NO:10.

8. The method of claim 7, wherein the antibody or antigen-binding fragment thereof is administered to the subject by intravitreal injection.

9. The method of claim 2, wherein the antibody or antigen-binding fragment thereof is administered to the subject by intravitreal injection.

10. The method of claim 1, wherein the isolated antibody or antigen-binding fragment thereof comprises a heavy chain variable region comprising the amino acid sequence of SEQ ID NO:2 and a light chain variable region comprising the amino acid sequence of SEQ ID NO:10.

11. The method of claim 10, wherein the antibody or antigen-binding fragment thereof is administered to the subject by intravitreal injection.

12. The method of claim 1, wherein the antibody or antigen-binding fragment thereof is administered to the subject by intravitreal injection.

* * * * *